United States Patent
Gray et al.

(10) Patent No.: US 9,284,285 B2
(45) Date of Patent: *Mar. 15, 2016

(54) HUMAN PROTEIN TYROSINE PHOSPHATASE INHIBITORS AND METHODS OF USE

(71) Applicant: Aerpio Therapeutics Inc., Cincinnati, OH (US)

(72) Inventors: Jeffrey Lyle Gray, Loveland, OH (US); Kande K. D. Amarasinghe, Ellicott City, MD (US); Cynthia Monesa Clark, Concord, MA (US); Ryan Matthew Nichols, Cincinnati, OH (US); Matthew B. Maier, Springboro, OH (US)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/252,140

(22) Filed: Apr. 14, 2014

(65) Prior Publication Data

US 2014/0221666 A1    Aug. 7, 2014

Related U.S. Application Data

(60) Continuation of application No. 13/691,757, filed on Dec. 1, 2012, now Pat. No. 8,946,232, which is a continuation of application No. 12/558,169, filed on Sep. 11, 2009, now abandoned, which is a division of application No. 11/823,086, filed on Jun. 26, 2007, now Pat. No. 7,622,593.

(60) Provisional application No. 60/816,730, filed on Jun. 27, 2006.

(51) Int. Cl.

| C07D 239/42 | (2006.01) |
| C07D 401/04 | (2006.01) |
| C07D 277/28 | (2006.01) |
| C07D 277/64 | (2006.01) |
| C07D 417/04 | (2006.01) |
| A61K 31/426 | (2006.01) |
| A61K 31/427 | (2006.01) |
| A61K 31/428 | (2006.01) |
| A61K 31/497 | (2006.01) |
| C07D 277/60 | (2006.01) |
| C07D 277/30 | (2006.01) |

(52) U.S. Cl.
CPC ............ *C07D 277/28* (2013.01); *A61K 31/426* (2013.01); *A61K 31/427* (2013.01); *A61K 31/428* (2013.01); *A61K 31/497* (2013.01); *C07D 277/30* (2013.01); *C07D 277/60* (2013.01); *C07D 277/64* (2013.01); *C07D 417/04* (2013.01)

(58) Field of Classification Search
None
See application file for complete search history.

(56) References Cited

U.S. PATENT DOCUMENTS

| 4,673,641 | A  | 6/1987  | George et al. |
| 5,424,398 | A  | 6/1995  | Middeldorp et al. |
| 5,585,089 | A  | 12/1996 | Queen et al. |
| 5,688,781 | A  | 11/1997 | Siegall et al. |
| 5,807,819 | A  | 9/1998  | Cheng et al. |
| 5,866,570 | A  | 2/1999  | Liang et al. |
| 5,994,128 | A  | 11/1999 | Fallaux et al. |
| 6,033,908 | A  | 3/2000  | Bout et al. |
| 6,342,219 | B1 | 1/2002  | Thorpe et al. |
| 6,455,035 | B1 | 9/2002  | Suri et al. |
| 6,589,758 | B1 | 7/2003  | Zhu |
| 6,596,772 | B1 | 7/2003  | Huang et al. |
| 6,930,117 | B2 | 8/2005  | Warshakoon et al. |
| 6,946,479 | B2 | 9/2005  | Warshakoon et al. |
| 7,226,755 | B1 | 6/2007  | Peters et al. |
| 7,247,632 | B2 | 7/2007  | Warshokoon et al. |
| 7,247,648 | B2 | 7/2007  | Warshokoon et al. |
| 7,507,568 | B2 | 3/2009  | Evdokimov |
| 7,588,924 | B2 | 9/2009  | Evdokimov et al. |
| 7,589,212 | B2 | 9/2009  | Gray et al. |
| 7,622,593 | B2 | 11/2009 | Gray et al. |
| 7,632,862 | B2 | 12/2009 | Peters et al. |
| 7,769,575 | B2 | 8/2010  | Evdokimov et al. |
| 7,790,748 | B2 | 9/2010  | Warshakoon et al. |
| 7,795,444 | B2 | 9/2010  | Gray et al. |
| 7,973,142 | B2 | 7/2011  | Rotello et al. |
| 8,106,078 | B2 | 1/2012  | Gray et al. |
| 8,133,894 | B2 | 3/2012  | Warshakoon et al. |
| 8,188,125 | B2 | 5/2012  | Gray et al. |
| 8,258,311 | B2 | 9/2012  | Gray et al. |
| 8,309,537 | B2 | 11/2012 | Gardner et al. |

(Continued)

FOREIGN PATENT DOCUMENTS

| EP | 0701817 A2 | 3/1996 |
| JP | 2002504490 A | 2/2002 |

(Continued)

OTHER PUBLICATIONS

U.S. Appl. No. 14/569,106, filed Dec. 12, 2014, Gray et al.

(Continued)

*Primary Examiner* — Craig Ricci

(74) *Attorney, Agent, or Firm* — Wilson Sonsini Goodrich & Rosati

(57) ABSTRACT

The present disclosure relates to compounds effective as human protein tyrosine phosphatase beta (HPTP-β) inhibitors thereby regulating angiogenesis. The present disclosure further relates to compositions comprising said human protein tyrosine phosphatase beta (HPTP-β) inhibitors, and to methods for regulating angiogenesis.

10 Claims, No Drawings

(56) References Cited

U.S. PATENT DOCUMENTS

| | | |
|---|---|---|
| 8,329,916 B2 | 12/2012 | Amarasinghe et al. |
| 8,338,615 B2 | 12/2012 | Gray et al. |
| 8,524,235 B2 | 9/2013 | Rotello et al. |
| 8,536,181 B2 | 9/2013 | Gardner et al. |
| 8,569,348 B2 | 10/2013 | Shalwitz et al. |
| 8,778,412 B2 | 7/2014 | Shalwitz et al. |
| 8,846,685 B2 | 9/2014 | Gray et al. |
| 8,883,774 B2 | 11/2014 | Shalwitz et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,999,325 B2 | 4/2015 | Peters et al. |
| 8,999,971 B2 | 4/2015 | Shalwitz et al. |
| 9,045,495 B2 | 6/2015 | Gardner et al. |
| 2004/0077065 A1 | 4/2004 | Evdokimov et al. |
| 2004/0097559 A1 | 5/2004 | Warshakoon et al. |
| 2004/0097560 A1 | 5/2004 | Warshakoon et al. |
| 2004/0167183 A1 | 8/2004 | Klopfenstein et al. |
| 2004/0204863 A1 | 10/2004 | Kim et al. |
| 2004/0242676 A1 | 12/2004 | Alessi et al. |
| 2005/0234045 A1 | 10/2005 | Warshakoon et al. |
| 2005/0256126 A1 | 11/2005 | Warshakoon et al. |
| 2005/0282814 A1 | 12/2005 | Wrasidlo et al. |
| 2007/0154482 A1 | 7/2007 | Sukhatme et al. |
| 2007/0238722 A1 | 10/2007 | Warshakoon et al. |
| 2007/0270407 A1 | 11/2007 | Warshakoon et al. |
| 2007/0299116 A1 | 12/2007 | Gray |
| 2008/0004267 A1 | 1/2008 | Gray |
| 2008/0076764 A1 | 3/2008 | Peters et al. |
| 2008/0108631 A1 | 5/2008 | Gray et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0305097 A1 | 12/2010 | Warshakoon et al. |
| 2011/0110961 A1 | 5/2011 | Gardner et al. |
| 2011/0111058 A1 | 5/2011 | Shalwitz et al. |
| 2011/0112055 A1 | 5/2011 | Gardner et al. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2012/0077853 A1 | 3/2012 | Gray et al. |
| 2012/0077975 A1 | 3/2012 | Gray et al. |
| 2012/0115876 A1 | 5/2012 | Warshakoon et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0158010 A1 | 6/2013 | Shalwitz et al. |
| 2013/0158045 A1 | 6/2013 | Gardner et al. |
| 2013/0324558 A1 | 12/2013 | Gray et al. |
| 2013/0331386 A1 | 12/2013 | Shalwitz et al. |
| 2014/0044707 A1 | 2/2014 | Rotello et al. |
| 2014/0066458 A1 | 3/2014 | Shalwitz et al. |
| 2014/0179717 A1 | 6/2014 | Bergmann et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2014/0364419 A1 | 12/2014 | Shalwitz et al. |
| 2015/0050277 A1 | 2/2015 | Peters et al. |
| 2015/0157617 A1 | 6/2015 | Shalwitz et al. |

FOREIGN PATENT DOCUMENTS

| | | |
|---|---|---|
| JP | 5261383 B2 | 8/2013 |
| WO | WO 00/57901 | 10/2000 |
| WO | WO 00/65085 | 11/2000 |
| WO | WO 00/65088 A1 | 11/2000 |
| WO | WO 02/26774 A1 | 4/2002 |
| WO | WO 2004/043927 A1 | 5/2004 |
| WO | WO 2004/043928 A2 | 5/2004 |
| WO | WO 2007/116360 A2 | 10/2007 |
| WO | WO 2008/002569 A2 | 1/2008 |
| WO | WO 2008/002570 A2 | 1/2008 |
| WO | WO 2008/002571 A2 | 1/2008 |
| WO | WO 2010/081172 A1 | 7/2010 |
| WO | WO 2011/005330 A1 | 1/2011 |
| WO | WO 2011/057112 A1 | 5/2011 |
| WO | WO 2011/057115 A1 | 5/2011 |
| WO | WO 2011/057121 A1 | 5/2011 |
| WO | WO 2012/047966 A2 | 4/2012 |
| WO | WO 2013/056233 A1 | 4/2013 |
| WO | WO 2013/056240 A1 | 4/2013 |
| WO | WO 2014/145068 A1 | 9/2014 |

OTHER PUBLICATIONS

U.S. Appl. No. 14/627,463, filed Feb. 20, 2015, Peters et al.
U.S. Appl. No. 14/657,276, filed Mar. 13, 2015, Janusz et al.
Collaborative Computational Project, No. 4. The CCP4 suite: programs for protein crystallography. Acta Crystallogr D Biol Crystallogr. Sep. 1, 1994;50(Pt 5):760-3.
European search report and opinion dated Apr. 25, 2013 for EP Application No. 12196174.2.
European search report and opinion dated Apr. 25, 2013 for EP Application No. 12196179.1.
European search report and opinion dated Oct. 22, 2014 for EP Application No. 14166121.5.
International search report and written opinion dated Dec. 10, 2007 for PCT/US2007/014823.
International search report and written opinion dated Dec. 11, 2007 for PCT/US2007/014822.
International search report and written opinion dated Dec. 11, 2007 for PCT/US2007/014824.
Kubinyi. 3D QSAR in Drug Design: Ligand-Protein Interactions and Molecular Similarity, vol. 2-3, Springer, 1998; pp. 243-244.
Notice of allowance dated Mar. 12, 2012 for U.S. Appl. No. 12/467,430.
Notice of allowance dated May 21, 2014 for U.S. Appl. No. 13/626,614.
Notice of allowance dated Jun. 14, 2012 for U.S. Appl. No. 12/624,072.
Notice of allowance dated Jul. 21, 2014 for U.S. Appl. No. 13/936,450.
Notice of allowance dated Jul. 26, 2010 for U.S. Appl. No. 11/821,846.
Notice of allowance dated Jul. 28, 2009 for U.S. Appl. No. 11/821,868.
Notice of allowance dated Sep. 15, 2014 for U.S. Appl. No. 13/691,757.
Notice of allowance dated Sep. 22, 2009 for U.S. Appl. No. 11/823,086.
Notice of allowance dated Oct. 19, 2012 for U.S. Appl. No. 13/309,452.
Notice of allowance dated Oct. 23, 2012 for U.S. Appl. No. 13/309,445.
Notice of allowance dated Nov. 15, 2011 for U.S. Appl. No. 12/850,026.
Office action dated Jan. 9, 2009 for U.S. Appl. No. 11/821,868.
Office action dated Jan. 16, 2014 for U.S. Appl. No. 13/626,590.
Office action dated Feb. 3, 2014 for U.S. Appl. No. 13/626,614.
Office action dated Feb. 16, 2012 for U.S. Appl. No. 12/558,169.
Office action dated Feb. 24, 2012 for U.S. Appl. No. 12/624,072.
Office action dated Mar. 4, 2009 for U.S. Appl. No. 11/823,086.
Office action dated Apr. 23, 2010 for U.S. Appl. No. 11/821,846.
Office action dated May 8, 2014 for U.S. Appl. No. 13/626,614.
Office action dated May 8, 2014 for U.S. Appl. No. 13/691,757.
Office action dated May 8, 2014 for U.S. Appl. No. 13/936,450.
Office action dated May 18, 2012 for U.S. Appl. No. 12/624,072.
Office action dated May 30, 2014 for U.S. Appl. No. 13/626,590.
Office action dated Aug. 8, 2011 for U.S. Appl. No. 12/850,026.
Office action dated Aug. 16, 2012 for U.S. Appl. No. 13/309,445.

(56) References Cited

OTHER PUBLICATIONS

Office action dated Aug. 30, 2012 for U.S. Appl. No. 13/309,452.
Office action dated Sep. 2, 2009 for U.S. Appl. No. 11/823,086.
Office action dated Oct. 2, 2008 for U.S. Appl. No. 11/821,868.
Office action dated Oct. 17, 2011 for U.S. Appl. No. 12/467,430.
Office action dated Oct. 26, 2012 for U.S. Appl. No. 12/558,169.
Office action dated Oct. 24, 2011 for U.S. Appl. No. 12/850,026.
Office action dated Nov. 14, 2013 for U.S. Appl. No. 13/626,590.
Office action dated Dec. 6, 2011 for U.S. Appl. No. 12/467,430.
Park, et al. Toxicogenetics in drug development. Toxicology Letters. 2001; 120:281-291.
Sledge, et al. Angiogenesis and antiangiogenic therapy. Curr Probl Cancer. 2002, 26:1-60.
Terfloth, et al. Electronic screening: Lead finding from database mining Wermuth, The Practice of Medicinal Chemsitry, 2d ed. (2003), Ch. 8-9, 131-157.
Yancopoulos, et al. Vascular-specific growth factors and blood vessel formation. Nature. Sep. 14, 2000;407(6801):242-8.
Altschul et al., "Gapped BLAST and PSI-BLAST: A New Generation of Protein Database Search Programs," Nucleic Acids Res., 25(27):3389-3402 (1997).
Annex et al., "Growth Factor-Induced Therapeutic Angiogenesis in the Heart: Protein Therapy," Cardiovascular Research, 65(3):649-655 (2005).
Ardelt et al., "Estradiol Regulates Angiopoietin-1 mRNA Expression Through Estrogen Receptor-α in a Rodent Experimental Stroke Model," Stroke, 36:337-341 (2005).
Auerbach et al., "Angiogenesis Assays: A Critical Overview," Clinical Chemistry, 49:32-40 (2003).
Barany et al., "Solid-phase Peptide Synthesis: A Silver Anniversary Report," Int J. Peptide Protein Res., 30(6):705-739 (1987).
Bartlett et al., "Molecular Recognition in Chemical and Biological Problems; Cavet: A Program to Facilitate the Structure-Derived Design of Biologically Active Molecules," Special Pub., Royal Chem. Soc., 78:182-196 (1989).
Bohm, "The Computer Program LUDI: A New Method for the De Novo Design of Enzyme Inhibitors," J. Computer-Aided. Molec. Design, 6(1):61-78 (1992).
Bussolino, et al., "Molecular mechanisms of blood vessel formation," Trends Biochem Sci. 22(7):251-256 (1997).
Carano et al., "Angiogenesis and Bone Repair," Drug Discovery Today, 8(21):980-989 (2003).
Carvalho et al., "The Role of Angiogenesis in a Murine Tibial Model of Distraction Osteogenesis," Bone, 34:849-861 (2004).
Chanteau et al., "Synthesis of Anthropomorphic Molecules: The NanoPutians," J. Org. Chem., 68:8750-8766 (2003).
Cohen et al., "Molecular Modeling Software and Methods for Medicinal Chemistry," J. Med. Chem., 33(3):883-894 (1990).
Daar, "Perspective: Emerging Resistance Profiles of Newly Approved Antiretroviral Drugs," Topics in HIV Medicine, 16(4):110-116 (2008).
Dean, "Recent Advances in Drug Design Methods: Where Will They Lead?" BioEssays, 16(9):683-687 (1994).
Fachinger et al., "Functional Interaction of Vascular Endothelial-Protein-Tyrosine Phosphatase with the Angiopoietin Receptor Tie-2," Oncogene, 18:5948-5953 (1999).
Flower, "Modelling G-Protein-Coupled Receptors for Drug Design," Biochimica et Biophysica Acta, 1422:207-¬234 (1999).
Folkman, J., "Tumor angiogenesis," The Molecular Basis of Cancer (eds. Mendelsohn, J., Howley, P. M., Israel, M. A. & Liotta, L. A.) 206-232 (1995).
Gaits et al., "Increase in Receptor-like Protein Tyrosine Phosphatase Activity and Express Level on Density-Dependent Growth Arrest of Endothelial Cells," Biochem J., 311:97-103 (1995).
Gallagher et al., "Angiopoietin 2 is a Potential Mediator of High-Dose Interleutkin 2-Induced Vascular Leak," Clin Cancer REs (2007);13:2115-2120.
Goodford, "A Computational Procedure for Determining Energetically Favorable Binding Sites on Biologically Important Macromolecules," J. Med. Chem., 28(7):849-57 (1985).

Goodsell et al., "Automated Docking of Substrates to Proteins by Simulated Annealing," Proteins Struct. Funct. Genet. 8:195-202 (1990).
Harder et al., "Characterization and Kinetic Analysis of the Intracellular Domain of Human Protein Tyrosine Phosphatase β (HPTPβ) Using Synthetic Phosphopeptides," Biochem. J., 296:395-401 (1994).
Henikoff et al., "Amino Acid Substitution Matrices from Protein Blocks," Proc. Natl. Acad. Sci. USA 89:10915-10919 (1992).
Hopkins et al., "Inhibitors of Kinesin Activity from Structure-Based Computer Screening," Biochemistry, 39:2805-2814 (2000).
Huang et al., "HCPTPA, a Protein Tyrosine Phosphatase that Regulates Vascular Endothelial Growth Factor Receptor-Mediated Signal Transduction and Biological Activity," J. Biol. Chem., 53:38183-38188 (1999).
Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," Journal of Biological Chemistry, 267(17):12356-12363 (1992).
Jones et al., "Development and Validation of a Genetic Algorithm for Flexible Docking," J. Mol. Biol., 267:727-748 (1997).
Jones et al., "Molecular Recognition of Receptor Sites Using a Genetic Algorithm with a Description of Desolvation," J. Mol. Biol., 245:43-53 (1995).
Keen, "Radioligand Binding Methods for Membrane Preparations and Intact cells," Methods in Molecular Biology, 83: Receptor Signal Transduction Protocols, edited Humana Press Inc., Totoway N. J. (1997).
Köhler et al., "Continuous Cultures of Fused Cells Secreting Antibody of Predefined Specificity," Biotechnology, 24:524-526 (1992).
Krueger et al., "Structural Diversity and evolution of Human Receptor-Like Protein Tyrosine Phosphatases," The EMBO Journal, 9(10):3241-3252 (1990).
Kugathasan et al., "Role of Angiopoietin-1 in Experimental and Human Pulmonary Arterial Hpertension," Chest, 128:633-642 (2005).
Kumpers et al., "Ecxess circulating angiopoietin-2 is a strong predictor of mortality in critically ill medical patients," Clinical Care (2008), vol. 12, No. 6.
Kumpers et al., "The Tie2 receptor antagonist angiopoietin 2 facilitates vascular inflammation in systemic lupus erythematosus," Ann. Rheum Dis 2009;68:1638-1643.
Kuntz et al., "A Geometric Approach to Macromolecule—Ligand Interactions," J. Mol. Biol. 161:269-288 (1982).
Lin et al., "Inhibition of Tumor Angiogenesis Using a Soluble Receptor Establishes a Role for Tie2 in Pathologic Vascular Growth," J. Clinical Invest.,100(8):2072-2078 (1997).
Ma et al., "RNase Protection Assay," Methods, 10(3):273-8 (1996).
Martin, "3D Database Searching in Drug Design," J. of Medicinal Chemistry, 35(12):2145-2154 (1992).
Meadows, "Keeping Up with Drug Safety Information," 2006: FDA Consumer Magazine: http://www.fda.gov/fdac/features/2006/306_drugsafety.html, accessed Mar. 17, 2008.
Merrifield, "Solid Phase Peptide Synthesism. I. The Synthesis of a Tetrapeptide," J. Am. Chem. Soc., 85:2149-2154 (1963).
Milner et al., "Roles of the receptor tyrosine kinases Tie1 and Tie2 in mediating the effects of angiopoietin-1 on endothelial permeability and apoptosis," Microvascular Research; 77(2009) pp. 187-191.
Miranker et al., "Functionality Maps of Binding Sites: A Multiple Copy Simultaneous Search Method," Proteins: Struc. Func. and Genectics, 11(1):29-34 (1991).
Navaza, "AMoRe: An Automated Package for Molecular Replacement," J. Acta Cryst. A50:157-163 (1994).
Nguyen et al., "Cellular Interactions in Vascular Growth and Differentiation," Int. Rev. Cytol., 204:1-48 (2001).
Nishibata et al., "Automatic Creation of Drug Candidate Structures Based on Receptor Structure. Starting Point for Artificial Lead Generation," Tetrahedron, 47(43):8985-8990 (1991).
O'Reilly, "Angiostatin: a novel angiogenesis inhibitor that mediates the suppression of metastases by a Lewis lung carcinoma," Cell, 79(2):315-28 (1994).

(56) References Cited

OTHER PUBLICATIONS

O'Reilly, "Endostatin: an endogenous inhibitor of angiogenesis and tumor growth," Cell, 88(2):277-85 (1997).
Rarey et al., "A Fast Flexible Docking Method Using an Incremental Construction Algorithm," J. Mol. Biol., 261:470-489 (1996).
Riechmann et al., "Reshaping Human Antibodies for Therapy," Nature, 332:323-327 (1988).
Roviezzo et al., "Angiopoietin-2 Causes Inflammation in Vivo by promoting Vascular Leakage," J. Pharmacology and Experimental Therapeutics; vol. 314, No. 2, (2005).
Indian Patent Application No. 515/DELNP/2009, Human Protein Tyrosine Phosphatase Inhibitors and Methods of Use, National Stage Entry of PCT/US2007/014822, claiming priority to U.S. Appl. No. 60/816,730, filed Jun. 27, 2006.
Indian Patent Application No. 513/DELNP/2009, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006.
Indian Patent Application No. 512/DELNP/2009, Human Protein Tyrosine Phosphatase Inhibitors and Methods of Use, National Stage Entry of PCT/US2007/014824, claiming priority to U.S. Appl. No. 60/816,825, filed Jun. 27, 2006.
Japanese Patent Application No. 2009-518226, Human Protein Tyrosine Phosphatase Inhibitors and Methods of Use, National Stage Entry of PCT/US2007/014822, claiming priority to U.S. Appl. No. 60/816,730, filed Jun. 27, 2006, now JP 5232778.
Japanese Patent Application No. 2013-62411, which is a Divisional Application of Japanese Patent Application No. 2009-518226, Human Protein Tyrosine Phosphatase Inhibitors and Methods of Use, National Stage Entry of PCT/US2007/014822, claiming priority to U.S. Appl. No. 60/816,730, filed Jun. 27, 2006.
Japanese Patent Application No. 2009-518227, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now JP 5261383.
Japanese Patent Application No. 2013-29649, which is a Divisional Application of Japanese Patent Application No. 2009-518227, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006.
Japanese Patent Application No. 2009-518228, Human Protein Tyrosine Phosphatase Inhibitors and Methods of Use, National Stage Entry of PCT/US2007/014824, claiming priority to U.S. Appl. No. 60/816,825, filed Jun. 27, 2006, now JP 5201740.
Korean Patent Application No. 2009-7001678, Human Protein Tyrosine Phosphatase Inhibitors and Methods of Use, National Stage Entry of PCT/US2007/014822, claiming priority to U.S. Appl. No. 60/816,730, filed Jun. 27, 2006, now KR 1155365.
Korean Patent Application No. 2009-7001694, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now KR 1179087.
Korean Patent Application No. 2009-7001692, Human Protein Tyrosine Phosphatase Inhibitors and Methods of Use, National Stage Entry of PCT/US2007/014824, claiming priority to U.S. Appl. No. 60/816,825, filed Jun. 27, 2006, now KR 1157844.
Mexican Patent Application No. MX/A/2009/000288, Human Protein Tyrosine Phosphatase Inhibitors and Methods of Use, National Stage Entry of PCT/US2007/014822, claiming priority to U.S. Appl. No. 60/816,730, filed Jun. 27, 2006.
Mexican Patent Application No. MX/A/2009/000289, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, Now MX 303155.
Mexican Patent Application No. MX/A/2009/000290, Human Protein Tyrosine Phosphatase Inhibitors and Methods of Use, National Stage Entry of PCT/US2007/014824, claiming priority to U.S. Appl. No. 60/816,825, filed Jun. 27, 2006, now MX 279959.
New Zealand Patent Application No. 574407, Human Protein Tyrosine Phosphatase Inhibitors and Methods of Use, National Stage Entry of PCT/US2007/014822, claiming priority to U.S. Appl. No. 60/816,730, filed Jun. 27, 2006, now NZ 57407.
New Zealand Patent Application No. 574406, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, Now NZ 574406.
New Zealand Patent Application No. 574405, Human Protein Tyrosine Phosphatase Inhibitors and Methods of Use, National Stage Entry of PCT/US2007/014824, claiming priority to U.S. Appl. No. 60/816,825, filed Jun. 27, 2006, now NZ 574405.
Philippine Application No. 12009500031, Human Protein Tyrosine Phosphatase Inhibitors and Methods of Use, National Stage Entry of PCT/US2007/014822, claiming priority to U.S. Appl. No. 60/816,730, filed Jun. 27, 2006, now PH 1-2009-500031.
Philippine Patent Application No. 1-2009500032, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now PH 1-2009-500032.
Philippine Patent Application No. 12009500033, Human Protein Tyrosine Phosphatase Inhibitors and Methods of Use, National Stage Entry of PCT/US2007/014824, claiming priority to U.S. Appl. No. 60/816,825, filed Jun. 27, 2006, now PH 1-2009-500033.
Russian Patent Application No. 2009102516, Human Protein Tyrosine Phosphatase Inhibitors and Methods of Use, National Stage Entry of PCT/US2007/014822, claiming priority to U.S. Appl. No. 60/816,730, filed Jun. 27, 2006, now RU 2447065.
Russian Patent Application No. 2009102538, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now RU 2435763.
Russian Patent Application No. 2009102537, Human Protein Tyrosine Phosphatase Inhibitors and Methods of Use, National Stage Entry of PCT/US2007/014824, claiming priority to U.S. Appl. No. 60/816,825, filed Jun. 27, 2006, now RU 2430101.
Singapore Patent Application No. 200809619-0, Human Protein Tyrosine Phosphatase Inhibitors and Methods of Use, National Stage Entry of PCT/US2007/014822, claiming priority to U.S. Appl. No. 60/816,730, filed Jun. 27, 2006.
Singapore Patent Application No. 200809621-6, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now SG 148804.
Singapore Patent Application No. 200809622, Human Protein Tyrosine Phosphatase Inhibitors and Methods of Use, National Stage Entry of PCT/US2007/014824, claiming priority to U.S. Appl. No. 60/816,825, filed Jun. 27, 2006.
South African Patent Application No. 2009/00559, Human Protein Tyrosine Phosphatase Inhibitors and Methods of Use, National Stage Entry of PCT/US2007/014824, claiming priority to U.S. Appl. No. 60/816,730, filed Jun. 27, 2006; now ZA 2009/00559.
South African Patent Application No. 2009/00492, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006; now ZA 2009/00492.

(56) References Cited

OTHER PUBLICATIONS

South African Patent Application No. 2009/00558, Human Protein Tyrosine Phosphatase Inhibitors and Methods of Use, National Stage Entry of PCT/US2007/014824, claiming priority to U.S. Appl. No. 60/816,825, filed Jun. 27, 2006; now ZA 2009/00558.
Saliba, "Heparin in the Treatment of Burns: A Review," May 2001; Burn 27(4):349-358; full text edition, pp. 1-16.
Schöneberg et al., "Structural basis of G protein-coupled receptor function," Molecular and Cellular Endocrinology, 151:181-193 (1999).
Sexton, "Recent advances in our understanding of peptide hormone receptors and RAMPS," Current Opinion in Drug Discovery and Development, 2(5):440-448 (1999).
Shiojima et al., "Disruption of Coordinated Cardiac Hypertrophy and Angiogenesis Contributes to the Transition to Heart Failure," Journal of Clinical Invest., 115(8):2108-2118 (2005).
Shoichet et al., "Lead Discovery Using Molecular Docking," Chem. Biology, 6:439-446 (2002).
Siddiqui et al., "Combination of angiopoietin-1 and vascular endothelial growth factor gene therapy enhances arteriogenesis in the ischemic myocardium," Biochem. Biophys. Res. Comm., 310:1002-1009 (2003).
Simons, "Angiogenesis: Where Do We Stand Now?," Circulation, 111:1556-1566 (2005).
Simons et al., "Clinical Trials in Coronary Angiogenesis," Circulation, 102:73-86 (2000).
Stal et al., "Detailed Analysis of Scoring Functions for Virtual Screening," J. Med. Chem., 44:1035-1042 (2001).
Stetler-Stevenson, "The Role of Matrix Metalloproteinases in Tumor Invasion, Metastasis, and Angiogenesis," Surg. Oncol. Clin. N. Am., 10(2):383-392 (2001).
Suggitt et al., "50 Years of Preclinical Anticancer Drug Screening: Empirical to Target-Drive Approaches," Clinical Cancer Research, 11:971-981 (2005).
Suri et al., "Increased Vascularization in Mice Overexpressing Angiopoietin-1," Science, 282:468-471 (1998).
Takahashi et al.,"Adenoviral-Delivered Angiopoietin-1 Reduces the Infarction and Attenuates the Progression of Cardiace Dysfunction in the Rate Model of Acute Myocardial Infarction," Molecular Therapy, 8(4):584-592 (2003).
Teischer, "Potentiation of cytotoxic cancer therapies by TNP-470 alone and with other anti-angiogenic agents," Int. J. Cancer, 57(6)920-925 (1994).
Thurston, "Complimentary Actions of VEGF and Angiopoietin-1 on Blood Vessel Growth and Leakage," J. Anat., 200:575-580 (2002).
Thurston et al., "Angiopoietin-1 Protects the Adult Vasculature Against Plasma Leakage," Nature Medicine, 6 (4):460-463 (2000).
Vailhe et al., "In Vitro Models of Vasculogenesis and Angiogenesis," Laboratory Investigation, 81:439-452 (2001).
Wang et al., "Expressions and Characterization of Wild Type, Truncated, and Mutant Forms of the Intracellular Region of the Receptor-Like Protein Tyrosine Phosphatase HPTPβ," J. of Bio. Chem., 267(23):16696-16702 (1992).
Weidner, "Tumor Angiogenesis and Metastasis Correlation in Invasive Breast Carcinoma," New Eng. J. Med., 324(1):108 (1991).
Whitaker et al., "Vascular Endothelial Growth Factor Receptor-2 and Neuropilin-1 Form a Receptor Complex That Is Responsible for the Differential Signaling Potency of VEGF165 and VEGF121," Journal of Biological Chemistry, 276(27):25520-25531 (2001).
Wright et al., "Protein-Tyrosine Phosphatases in the Vessel Wall Differential Expression After Actue Arterial Injury," Arterioscler Thromb. Vasc., 1189-1198 (2000).
Yacyshyn et al., "Tyrosine phosphatase beta regulates angiopoietin-Tie2 signaling in human endothelial cells," Angiogenesis (2009) 12:25-33.
Zhang et al., "Vascular Endothelial Growth Factor and Angiopoietins in Focal Cerebral Ischemia," Trends Cardiovascular Med., 12(2):62-66 (2002).
Australian Patent Application No. 2007265453, Human Protein Tyrosine Phosphatase Inhibitors and Methods of Use, National Stage Entry of PCT/US2007/014822, claiming priority to U.S. Appl. No. 60/816,730, filed Jun. 27, 2006; now AU2007265453.
Australian Patent Application No. 2007265454, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006; now AU2007265454.
Australian Patent Application No. 2007265455, Human Protein Tyrosine Phosphatase Inhibitors and Methods of Use, National Stage Entry of PCT/US2007/014824, claiming priority to U.S. Appl. No. 60/816,825, filed Jun. 27, 2006; now AU2007265455.
Australian Patent Application No. 2012200253, which is a Divisional Application of Australian Patent Application No. 2007265455, Human Protein Tyrosine Phosphatase Inhibitors and Methods of Use, National Stage Entry of PCT/US2007/014824, claiming priority to U.S. Appl. No. 60/816,825, filed Jun. 27, 2006; now AU2012200253.
Brazilian Patent Application No. PI 071.3570-0, Human Protein Tyrosine Phosphatase Inhibitors and Methods of Use, National Stage Entry of PCT/US2007/014822, claiming priority to U.S. Appl. No. 60/816,730, filed Jun. 27, 2006.
Brazilian Patent Application No. PI 071.3357-0, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006.
Brazilian Patent Application No. PI 071.3349-9, Human Protein Tyrosine Phosphatase Inhibitors and Methods of Use, National Stage Entry of PCT/US2007/014824, claiming priority to U.S. Appl. No. 60/816,825, filed Jun. 27, 2006.
Canadian Patent Application No. 2,657,096, Human Protein Tyrosine Phosphatase Inhibitors and Methods of Use, National Stage Entry of PCT/US2007/014822, claiming priority to U.S. Appl. No. 60/816,730, filed Jun. 27, 2006; now CA 2,657,096.
Canadian Patent Application No. 2,657,107, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now CA 2,657,107.
Canadian Patent Application No. 2,656,915, Human Protein Tyrosine Phosphatase Inhibitors and Methods of Use, National Stage Entry of PCT/US2007/014824, claiming priority to U.S. Appl. No. 60/816,825, filed Jun. 27, 2006; now CA 2,656,915.
Chinese Patent Application No. 200780030939.0, Human Protein Tyrosine Phosphatase Inhibitors and Methods of Use, National Stage Entry of PCT/US2007/014824, claiming priority to U.S. Appl. No. 60/816,730, filed Jun. 27, 2006; now CN 200780030939.0.
Chinese Patent Application No. 200780030984.6, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now CN 200780030984.6.
Chinese Patent Application No. 200780031040.0, Human Protein Tyrosine Phosphatase Inhibitors and Methods of Use, National Stage Entry of PCT/US2007/014824, claiming priority to U.S. Appl. No. 60/816,825, filed Jun. 27, 2006; now CN 200780031040.0.
Colombian Patent Application No. 09007333, Human Protein Tyrosine Phosphatase Inhibitors and Methods of Use, National Stage Entry of PCT/US2007/014824, claiming priority to U.S. Appl. No. 60/816,730, filed Jun. 27, 2006, now CO 6150144.
Colombian Patent Application No. 09007333, Human Protein Tyrosine Phosphatase Inhibitors and Methods of Use, National Stage Entry of PCT/US2007/014824, claiming priority to U.S. Appl. No. 60/816,730, filed Jun. 27, 2006.
Colombian Patent Application No. 09007337, Human Protein Tyrosine Phosphatase Inhibitors and Methods of Use, National Stage Entry of PCT/US2007/014824, claiming priority to U.S. Appl. No. 60/816,825, filed Jun. 27, 2006.

(56) References Cited

OTHER PUBLICATIONS

European Patent Application No. 07 809 907.4, Human Protein Tyrosine Phosphatase Inhibitors and Methods of Use, National Stage Entry of PCT/US2007/014822, claiming priority to U.S. Appl. No. 60/816,730, filed Jun. 27, 2006.
European Patent Application No. 12 196 174.2, which is a Divisional Application of European Patent Application No. 07 809 907.4, Human Protein Tyrosine Phosphatase Inhibitors and Methods of Use, National Stage Entry of PCT/US2007/014822, claiming priority to U.S. Appl. No. 60/816,730, filed Jun. 27, 2006.
European Patent Application No. 07809 908.2, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006.
European Patent Application No. 07 809 909.0, Human Protein Tyrosine Phosphatase Inhibitors and Methods of Use, National Stage Entry of PCT/US2007/014824, claiming priority to U.S. Appl. No. 60/816,825, filed Jun. 27, 2006.
European Patent Application No. 14 166 121.5, which is a Divisional Application of European Patent Application No. 07 809 909.0, Human Protein Tyrosine Phosphatase Inhibitors and Methods of Use, National Stage Entry of PCT/US2007/014824, claiming priority to U.S. Appl. No. 60/816,825, filed Jun. 27, 2006.
Indonesian Patent Application No. W-00200804213, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006.
Indonesian Patent Application No. W-00200804212, Human Protein Tyrosine Phosphatase Inhibitors and Methods of Use, National Stage Entry of PCT/US2007/014824, claiming priority to U.S. Appl. No. 60/816,825, filed Jun. 27, 2006.
Indonesian Patent Application No. W-00200804210, Human Protein Tyrosine Phosphatase Inhibitors and Methods of Use, National Stage Entry of PCT/US2007/014822, claiming priority to U.S. Appl. No. 60/816,730, filed Jun. 27, 2006.
Israeli Patent Application No. 196128, Human Protein Tyrosine Phosphatase Inhibitors and Methods of Use, National Stage Entry of PCT/US2007/014822, claiming priority to U.S. Appl. No. 60/816,730, filed Jun. 27, 2006, now IL 196128.
Israeli Patent Application No. 196129, Human Protein Tyrosine Phosphatase Inhibitors and Methods of Use, National Stage Entry of PCT/US2007/014823, claiming priority to U.S. Appl. No. 60/816,730, filed Jun. 27, 2006; U.S. Appl. No. 60/815,731, filed Jun. 27, 2006; and U.S. Appl. No. 60/816,825, filed Jun. 27, 2006, now IL 196,129.
Israeli Patent Application No. 196130, Human Protein Tyrosine Phosphatase Inhibitors and Methods of Use, National Stage Entry of PCT/US2007/014824, claiming priority to U.S. Appl. No. 60/816,825, filed Jun. 27, 2006, now IL 196130.
U.S. Appl. No. 14/624,625, filed Feb. 18, 2015, Alberico.
U.S. Appl. No. 14/688,216, filed Apr. 16, 2015, Gardner et al.
U.S. Appl. No. 14/819,871, filed Aug. 6, 2015, Peters.
Notice of allowance dated May 26, 2015 for U.S. Appl. No. 14/569,106.

HUMAN PROTEIN TYROSINE PHOSPHATASE INHIBITORS AND METHODS OF USE

PRIORITY

This application is a Continuation of application Ser. No. 13/691,757, filed Dec. 1, 2012, which is a Continuation of application Ser. No. 12/558,169, filed Sep. 11, 2009, which is a Divisional of application Ser. No. 11/823,086, now U.S. Pat. No. 7,622,593, which claims the benefit of Provisional Application Ser. No. 60/816,730 filed on Jun. 27, 2006, the entire disclosure of which Applications are incorporated herein by reference in their entirety.

FIELD OF THE DISCLOSURE

The present disclosure relates to compounds effective as human protein tyrosine phosphatase beta (HPTP-β) inhibitors thereby regulating angiogenesis. The present disclosure further relates to compositions comprising said human protein tyrosine phosphatase beta (HPTP-β) inhibitors, and to methods for regulating angiogenesis.

BACKGROUND OF THE DISCLOSURE

Angiogenesis, the sprouting of new blood vessels from the pre-existing vasculature, plays a crucial role in a wide range of physiological and pathological processes (Nguyen, L. L. et al., *Int. Rev. Cytol.*, 204, 1-48, (2001)). Angiogenesis is a complex process, mediated by communication between the endothelial cells that line blood vessels and their surrounding environment. In the early stages of angiogenesis, tissue or tumor cells produce and secrete pro-angiogenic growth factors in response to environmental stimuli such as hypoxia. These factors diffuse to nearby endothelial cells and stimulate receptors that lead to the production and secretion of proteases that degrade the surrounding extracellular matrix. The activated endothelial cells begin to migrate and proliferate into the surrounding tissue toward the source of these growth factors (Bussolino, F., *Trends Biochem. Sci.*, 22, 251-256, (1997)). Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

Angiogenesis is regulated by a balance of naturally occurring pro- and anti-angiogenic factors. Vascular endothelial growth factor, fibroblast growth factor, and angiopoeitin represent a few of the many potential pro-angiogenic growth factors. These ligands bind to their respective receptor tyrosine kinases on the endothelial cell surface and transduce signals that promote cell migration and proliferation. Whereas many regulatory factors have been identified, the molecular mechanisms of this process are still not fully understood.

There are many disease states driven by persistent unregulated or improperly regulated angiogenesis. In such disease states, unregulated or improperly regulated angiogenesis may either cause a particular disease or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness. Both the growth and metastasis of solid tumors are also angiogenesis-dependent (Folkman et al., "Tumor Angiogenesis," Chapter 10, 206-32, in The Molecular Basis of Cancer, Mendelsohn et al., eds., W. B. Saunders, (1995)). It has been shown that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.*, 324, 1, 1-8 (1991)). When used as drugs in tumor-bearing animals, natural inhibitors of angiogenesis may prevent the growth of small tumors (O'Reilly et al., *Cell*, 79, 315-28 (1994)). In some protocols, the application of such inhibitors leads to tumor regression and dormancy even after cessation of treatment (O'Reilly et al., *Cell*, 88, 277-85 (1997)). Moreover, supplying inhibitors of angiogenesis to certain tumors may potentiate their response to other therapeutic regimens (Teischer et al., *Int. J. Cancer*, 57, 920-25 (1994)).

Although many disease states are driven by persistent unregulated or improperly regulated angiogenesis, some disease states could be treated by increased angiogenesis. Tissue growth and repair are biologic events wherein cellular proliferation and angiogenesis occur. Thus an important aspect of wound repair is the revascularization of damaged tissue by angiogenesis.

Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Atherosclerotic lesions in large vessels may cause tissue ischemia that could be ameliorated by modulating blood vessel growth to the affected tissue. For example, atherosclerotic lesions in the coronary arteries may cause angina and myocardial infarction that could be prevented if one could restore blood flow by stimulating the growth of collateral arteries. Similarly, atherosclerotic lesions in the large arteries that supply the legs may cause ischemia in the skeletal muscle that limits mobility and in some cases necessitates amputation, which may also be prevented by improving blood flow with angiogenic therapy.

Other diseases such as diabetes and hypertension are characterized by a decrease in the number and density of small blood vessels such as arterioles and capillaries. These small blood vessels are important for the delivery of oxygen and nutrients. A decrease in the number and density of these vessels contributes to the adverse consequences of hypertension and diabetes including claudication, ischemic ulcers, accelerated hypertension, and renal failure. These common disorders and many other less common ailments, such as Burgers disease, could be ameliorated by increasing the number and density of small blood vessels using angiogenic therapy.

It has been suggested that one means for regulating angiogenesis is to treat patients with a human protein tyrosine phosphatase beta (HPTP-3) inhibitor (Kruegar et al., *EMBO J.*, 9, (1990)) and, therefore, to satisfy this need the compounds of the present disclosure have been prepared.

SUMMARY OF THE DISCLOSURE

The compounds of the present disclosure are a new class of compounds that can regulate angiogenesis in humans.

The present disclosure further relates to pharmaceutical compositions and their pharmaceutically acceptable salts, and/or pharmaceutical compositions thereof comprising
 a) an effective amount of one or more compounds according to the present disclosure; and
 b) an excipient . . . .

The present disclosures also relate to methods for controlling angiogenesis, and thereby providing a treatment for diseases affected by angiogenesis, said methods comprising administering to a human an effective amount of a compound according to the present disclosure.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (o C) unless otherwise specified. All documents cited are in relevant part, incorporated herein by reference; the citation of any document is not to be construed as an admission that it is prior art with respect to the present disclosure.

DETAILED DESCRIPTION OF THE DISCLOSURE

In this specification and in the claims that follow, reference will be made to a number of terms, which shall be defined to have the following meanings:

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "organic unit" as described herein refers to groups or moieties that comprise one or more carbon atoms and which form a portion of one of the compounds or pharmaceutically acceptable salts thereof. For example, many of the substituent units referred to elsewhere herein are organic units. In order to effectively function in the context of their presence in the compounds and/or salts disclosed herein, the organic units should often have variable ranges of restricted size and/or molecular weight, so as to provide desired binding to the target enzymes, solubility, bioabsorption characteristics. For example, organic unit can have, for example, 1-26 carbon atoms, 1-18 carbon atoms, 1-12 carbon atoms, 1-8 carbon atoms, or 1-4 carbon atoms. Organic units often have hydrogen bound to at least some of the carbon atoms of the organic units, and can optionally contain the common heteroatoms found in substituted organic compounds, such as oxygen, nitrogen, sulfur, and the like, or inorganic atoms such as halogens, phosphorus, and the like. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl (C$_2$), 1,2-difluoroethyl (C$_2$), 2,2,2-trifluoroethyl (C$_3$), 3-carboxypropyl (C$_3$), 2,3-dihydroxycyclobutyl (C$_4$), and the like.

Substituted and unsubstituted linear, branched, or cyclic alkenyl include, ethenyl (C$_2$), 3-propenyl (C$_3$), 1-propenyl (also 2-methylethenyl)(C$_3$), isopropenyl (also 2-methylethen-2-yl) (C$_3$), buten-4-yl (C$_4$), and the like; substituted linear or branched alkenyl, non-limiting examples of which include, 2-chloroethenyl (also 2-chlorovinyl) (C$_2$), 4-hydroxybuten-1-yl (C$_4$), 7-hydroxy-7-methyloct-4-en-2-yl (C$_9$), 7-hydroxy-7-methyloct-3,5-dien-2-yl (C$_9$), and the like.

Substituted and unsubstituted linear or branched alkynyl include, ethynyl (C$_2$), prop-2-ynyl (also propargyl) (C$_3$), propyn-1-yl (C$_3$), and 2-methyl-hex-4-yn-1-yl (C$_7$); substituted linear or branched alkynyl, non-limiting examples of which include, 5-hydroxy-5-methylhex-3-ynyl (C$_7$), 6-hydroxy-6-methylhept-3-yn-2-yl (C$_8$), 5-hydroxy-5-ethylhept-3-ynyl (C$_9$), and the like.

Substituted and unsubstituted "alkoxy" are used herein denotes a unit having the general formula —OR$^{100}$ wherein R$^{100}$ is an alkyl, alkylenyl, or alkynyl unit as defined herein above, for example, methoxy, methoxymethyl, methoxymethyl.

Substituted and unsubstituted "haloalkyl" are used herein denotes an alkyl unit having a hydrogen atom substituted by one or more halogen atoms, for example, trifluoromethyl, 1,2-dichloroethyl, and 3,3,3-trifluoropropyl.

The term "aryl" as used herein denotes cyclic organic units that comprise at least one benzene ring having a conjugated and aromatic six-membered ring, non-limiting examples of which include phenyl (C$_6$), naphthylen-1-yl (C$_{10}$), naphthylen-2-yl (C$_{10}$). Aryl rings can have one or more hydrogen atoms substituted by another organic or inorganic radical. Non-limiting examples of substituted aryl rings include: 4-fluorophenyl (C$_6$), 2-hydroxyphenyl (C$_6$), 3-methylphenyl (C$_6$), 2-amino-4-fluorophenyl (C$_6$), 2-(N,N-diethylamino) phenyl (C$_6$), 2-cyanophenyl (C$_6$), 2,6-di-tert-butylphenyl (C$_6$), 3-methoxyphenyl (C$_6$), 8-hydroxynaphthylen-2-yl (C$_{10}$), 4,5-dimethoxynaphthylen-1-yl (C$_{10}$), and 6-cyanonaphthylen-1-yl (C$_{10}$).

The term "heteroaryl" denotes an organic unit comprising a five or six member conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A "heteroaryl" can also be a fused multicyclic and heteroaromatic ring system having wherein at least one of the rings is an aromatic ring and at least one atom of the aromatic ring is a heteroatom including nitrogen, oxygen, or sulfur The following are non-limiting examples of heteroaryl rings according to the present disclosure:

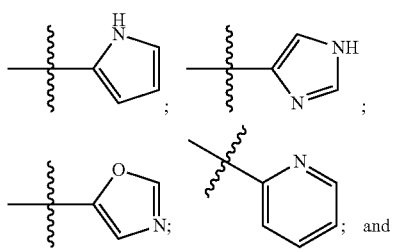

-continued

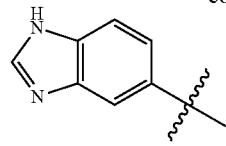

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

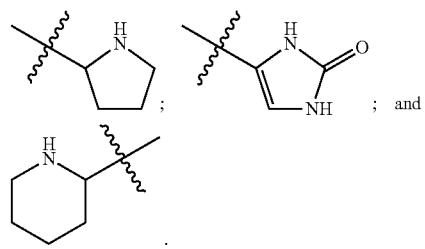

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

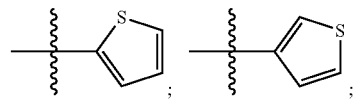 [SMILES: *c1cccs1 ; *c1ccsc1]

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

The term "substituted" is used throughout the specification. The term "substituted" is defined herein as "a hydrocarbyl moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. A three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent.

When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit," 3-guanidinopropyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_1$-$C_9$ heterocyclic rings; as described herein;

iv) substituted or unsubstituted $C_1$-$C_9$ heteroaryl rings; as described herein below;

v) —$(CR^{13a}R^{13b})_zOR^{12}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vi) —$(CR^{13a}R^{13b})_zC(O)R^{12}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;

vii) —$(CR^{13a}R^{13b})_zC(O)OR^{12}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

viii) —$(CR^{13a}R^{13b})_zC(O)N(R^{12})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

ix) —$(CR^{13a}R^{13b})_zN(R^{12})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

x) halogen; —F, —Cl, —Br, and —I;

xi) —$(CR^{13a}R^{13b})_zCN$;

xii) —$(CR^{13a}R^{13b})_zNO_2$;

xiii) —$CH_jX_k$; wherein X is halogen, j is from 0 to 2, j+k=3; for example, —$CH_2F$, —$CHF_2$, —$CF_3$, —$CCl_3$, or —$CBr_3$;

xiv) —$(CR^{13a}R^{13b})_zSR^{12}$; —SH, —$CH_2SH$, —$SCH_3$, —$CH_2SCH_3$, —$SC_6H_5$, and —$CH_2SC_6H_5$;

xv) —$(CR^{13a}R^{13b})_zSO_2R^{12}$; —$SO_2H$, —$CH_2SO_2H$, —$SO_2CH_3$, —$CH_2SO_2CH_3$, —$SO_2C_6H_5$, and —$CH_2SO_2C_6H_5$; and xiii) —$(CR^{13a}R^{13b})_zSO_3R^{12}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{12}$ is independently hydrogen, substituted or unsubstituted $C_1$-$C_4$ linear, branched, or cyclic alkyl, phenyl, benzyl; or two $R^{12}$ units can be taken together to form a ring comprising 3-7 atoms; $R^{13a}$ and $R^{13b}$ are each independently hydrogen or $C_1$-$C_4$ linear or branched alkyl; the index p is from 0 to 4.

For the purposes of the present disclosure the terms "compound," "analog," and "composition of matter" stand equally well for the disclosed chemical entities described herein, including all enantiomeric forms, diastereomeric forms, salts, and the like, and the terms "compound," "analog," and "composition of matter" are used interchangeably throughout the present specification.

The present disclosure addresses several unmet medical needs, inter alia;

1) Providing compositions effective as human protein tyrosine phosphatase beta (HPTP-β) inhibitors; and thereby providing a method for regulating angiogenesis in a disorder, disease, malady, or condition wherein angiogenesis is elevated;

2) Providing compositions effective as human protein tyrosine phosphatase beta (HPTP-β) inhibitors; and thereby providing a method for regulating angiogenesis in a disorder, disease, malady, or condition; and 3) Providing compositions effective as human protein tyrosine phosphatase beta (HPTP-β) inhibitors; and thereby providing a method for regulating angiogenesis in a disorder, disease, malady, or condition wherein angiogenesis is decreased.

These and other unmet medical needs are resolved by the human protein tyrosine phosphatase beta (HPTP-β) inhibitors of the present disclosure, that are capable of regulating angiogenesis and thereby serving as a method for treating elevated or diminished angiogenesis in humans or in treating diseases that are caused by insufficient regulation of human protein tyrosine phosphatase beta (HPTP-β).

The compounds disclosed herein include all pharmaceutically acceptable salt forms, for example, salts of both basic groups, inter alia, amines, as well as salts of acidic groups, inter alia, sulfamic acids, and carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

The compounds of the present disclosure have Formula (I):

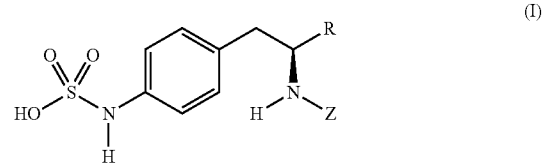

wherein the carbon atom having the amino unit has the (S) stereochemistry as indicated in the formula.

R is a substituted or unsubstituted thiazolyl unit having the formula:

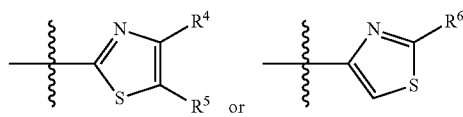

$R^4$, $R^5$, and $R^6$ are substituent groups that can be independently chosen from a wide variety of inorganic (hydrogen, hydroxyl, amino, halogen or the like) or organic substituent units, such as alkyls, cycloalkyls, heterocyclic, heteroaryls, and the like, wherein such substituent units can optionally have from 1 to 12 carbon atoms, or 1 to 10 carbon atoms, or 1 to six carbon atoms.

One example of compounds of Formula (I), R units relates to thiazol-2-yl units having the formula:

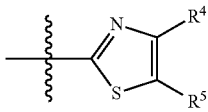

wherein $R^4$ and $R^5$ are each independently chosen from:
  i) hydrogen;
  ii) substituted or unsubstituted $C_1$-$C_6$ linear, branched, or cyclic alkyl;
  iii) substituted or unsubstituted phenyl;
  iv) substituted or unsubstituted heteroaryl; or
$R^4$ and $R^5$ can be taken together to form a saturated or unsaturated ring having from 5 to 7 atoms.

One example of compounds of Formula (I) includes R units having the formula:

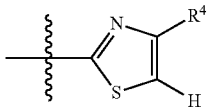

wherein $R^5$ is hydrogen and $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_5$), n-hexyl ($C_6$), 4-methylpentyl ($C_6$), and cyclohexyl ($C_6$).

Another example of compounds of Formula (I), R units include to units wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^5$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

A further example of compounds of Formula (I), R units include units wherein $R^5$ is hydrogen and $R^4$ is a substituted alkyl unit, said substitutions chosen from:
  i) halogen: —F, —Cl, —Br, and —I;
  ii) —N($R^{11}$)$_2$; and
  iii) —O$R^{11}$;
wherein each $R^{11}$ is independently hydrogen or $C_1$-$C_4$ linear or branched alkyl.

Non-limiting examples of units that can be a substitute for hydrogen on R units include —$CH_2F$, —$CHF_2$, —$CF_3$, —$CH_2CF_3$, —$CH_2CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

Other non-limiting examples of units that comprise R units include 2,2-difluorocyclopropyl, 2-methoxycyclohexyl, and 4-chlorocyclohexyl.

A yet further example of compounds of Formula (I), R units include units wherein $R^5$ is hydrogen and $R^4$ is phenyl or substituted phenyl, wherein non-limiting examples of $R^4$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)phenyl, 4-(trifluoro-methoxy)phenyl, 3-chloropheny, 4-chlorophenyl, and 3,4-dichlorophenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chloropheny, 4-chlorophenylthiazol-2-yl, and 3,4-dichlorophenylthiazol-2-yl.

A still further example of compounds of Formula (I) includes R units wherein $R^4$ is chosen from hydrogen, methyl, ethyl, n-propyl, and iso-propyl and $R^5$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

Another further example of compounds of Formula (I) includes R units wherein $R^5$ is hydrogen and $R^4$ is a substituted or unsubstituted heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^4$ is substituted or unsubstituted thiophene-2-yl, for example thiophene-2-yl, 5-chlorothiophene-2-yl, and 5-methylthiophene-2-yl.

A still further example of compounds of Formula (I) includes R units wherein $R^4$ is substituted or unsubstituted thiophene-3-yl, for example thiophene-3-yl, 5-chlorothiophene-3-yl, and 5-methylthiophene-3-yl.

Another example of compounds of Formula (I) includes R units wherein $R^4$ and $R^5$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl units having the formula:

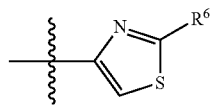

wherein $R^6$ is a unit chosen from:
  i) hydrogen;
  ii) substituted or unsubstituted $C_1$-$C_6$ linear, branched, or cyclic alkyl;
  iii) substituted or unsubstituted phenyl rings having from 5 to 10 ring atoms; or
  iv) substituted or unsubstituted heteroaryl having from 5 to 10 ring atoms.

An example of compounds of Formula (I) includes R units wherein $R^6$ is hydrogen.

A further example of compounds of Formula (I) includes R units wherein $R^6$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

A still further example of compounds of Formula (I) includes R units wherein $R^6$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

Yet further example of compounds of Formula (I) includes R units wherein $R^6$ is substituted or unsubstituted heteroaryl, non-limiting examples of which include thiophene-2-yl, thiophene-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

A further example of compounds of Formula (I) includes R units wherein $R^6$ is a unit having the formula:

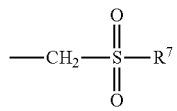

wherein $R^7$ is $C_1$-$C_4$ substituted or unsubstituted alkyl and substituted or unsubstituted phenyl, non-limiting examples of $R^6$ include 4-chlorobenzenesulfonylmethyl and tert-butylsulfonylmethyl.

A further example of compounds of Formula (I) includes R units wherein $R^6$ is a unit chosen from substituted or unsubstituted pyridinyl, pyrazinyl, and pyrimidinyl, non-limiting examples of which include pyrazin-2-yl and (2-methyl)pyridin-5-yl.

$R^1$ Units

One example of $R^1$ units includes compounds wherein $R^1$ is hydrogen. The compounds of the present disclosure wherein $R^1$ is equal to hydrogen have the formula:

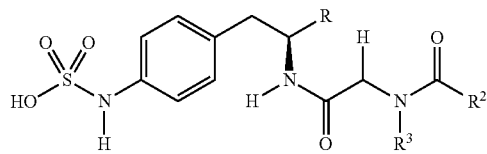

and the compounds of this category therefore do not comprise a second chiral center.

Another example of compounds of Formula (I) includes $R^1$ units having a second chiral center and, for example, having the formulae:

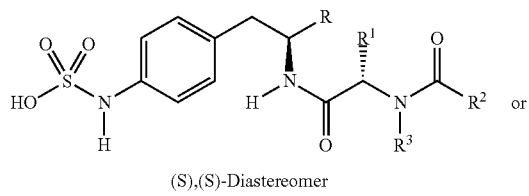

(S),(S)-Diastereomer or

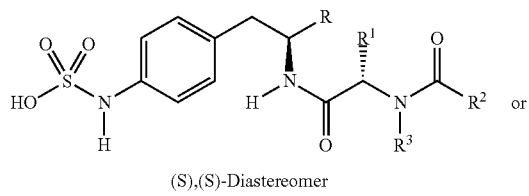

(S),(R)-Diastereomer and the indicated stereochemistry. The disclosed compounds can be single diastereomers or mixtures thereof and can be obtained by the formulator in any of the following ways:
  i) as a mixture of the (S),(S) and (S),(R) diastereomers and used as a mixture for regulation of angiogenesis;
  ii) as a mixture of the (S),(S) and (S),(R) diastereomers that are then subsequently separated into the single diastereomers before being used for regulation of angiogenesis; or
  iii) directly prepared as the individual (S),(S) or (S),(R) diastereomer, the method further described herein below.

One example of compounds according to Formula (I) includes $R^1$ units that are benzyl, non-limiting examples of which include 4-{(S)-2-[(S)-2-(tert-butoxycarbonyl)-3-phenylpropanamido]-2-(4-ethylthiazol-2-yl)ethyl}phenylsulfamic acid, 4-{(S)-2-(S)-2-(tert-butoxycarbonyl)-3-phenylpropanamido-2-(2-phenylthiazole-4-yl)}phenylsulfamic acid, 4-{(S)-2-(4-ethylthiazol-2-yl)-2-[(S)-2-(methoxycarbonyl)-3-phenylpropanamido]-ethyl}phenylsulfamic acid, and 4-{(S)-2-[(S)-2-(methoxycarbonyl)-3-phenylpropan-amido]-2-(2-ethylthiazol-4-yl)ethyl}phenylsulfamic acid, as well as other compounds described herein below.

Another example of compounds according to Formula (I) includes $R^1$ units that are substituted benzyl, non-limiting examples of which include 4-{(S)-2-[(S)-2-(tert-butoxycarbonyl)-3-(4-hydroxyphenyl)propanamido]-2-(4-ethylthiazol-2-yl)ethyl}phenylsulfamic acid; 4-{(S)-2-(S)-2-(tert-butoxycarbonyl)-3-(4-chlorophenyl)propaneamido-2-(2-phenylthiazole-4-yl)}phenylsulfamic acid, and 4-{(S)-2-(4-ethylthiazol-2-yl)-2-[(S)-2-(methoxycarbonyl)-3-(4-methylphenyl)propanamido]-ethyl}phenylsulfamic acid.

A further example of compounds according to Formula (I) includes $R^1$ units that are phenyl, non-limiting examples of which include 4-{(S)-2-[(S)-2-(tert-butoxycarbonyl)-2-phenylethanamido]-2-(4-ethylthiazol-2-yl)ethyl}phenylsulfamic acid, 4-{(S)-2-(S)-2-(tert-butoxycarbonyl)-2-phenylethaneamido-2-(2-phenylthiazole-4-yl)}phenylsulfamic acid, and 4-{(S)-2-(4-ethylthiazol-2-yl)-2-[(S)-2-(methoxycarbonyl)-2-phenylethaneamido]-ethyl}phenylsulfamic acid.

A yet further example of compounds according to Formula (I) includes $R^1$ units that are $C_1$-$C_4$ linear or branched alkyl non-limiting examples of which include 4-{(S)-2-(4-ethylthiazol-2-yl)-2-[(S)-2-(methoxycarbonyl)-3-methylbutanamido]-ethyl}phenylsulfamic acid, 4-{(S)-2-[(S)-2-(tert-butoxycarbonyl)-4-methylpentanamido]-2-(4-ethylthiazol-2-yl)ethyl}phenylsulfamic acid, and 4-{(S)-2-(4-Ethylthiazol-2-yl)-2-[(S)-2-(methoxycarbonyl)-4-methylpentan-amido]ethyl}phenylsulfamic acid, as well as other compounds described herein below.

$R^2$ is a unit chosen from:
  i) $C_1$-$C_6$ linear or branched alkyl; or
  ii) $C_1$-$C_6$ linear or branched alkoxy.

One example of R² includes $C_1$-$C_6$ linear or branched alkoxy units having the formula:

—OR⁸ wherein R⁸ is a $C_1$-$C_6$ linear or branched alkyl unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), or n-hexyl ($C_6$).

Another example of compounds according to Formula (I) includes R² units that are $C_1$-$C_6$ linear or branched alkyl chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), or n-hexyl ($C_6$).

R³ is hydrogen or $C_1$-$C_4$ linear or branched alkyl.

One example of R³ includes compounds wherein R³ is hydrogen.

Another example of R³ includes compounds wherein R³ is methyl.

A further example of R³ includes compounds wherein R³ is chosen from ethyl ($C_2$), n-propyl ($C_3$), iso-propyl ($C_3$), n-butyl ($C_4$), sec-butyl ($C_4$), iso-butyl ($C_4$), and tert-butyl ($C_4$).

The compounds of Formula (I) can be organized into several categories for the strictly non-limiting purpose of describing alternatives for synthetic strategies for the preparation of subgenera of compounds within the scope of Formula (I) that are not expressly exemplified herein. This mental organization into categories does not imply anything with respect to increased or decreased biological efficacy with respect to any of the compounds or compositions of matter described herein.

The first aspect of Category I of the present disclosure relates to compounds having the formula:

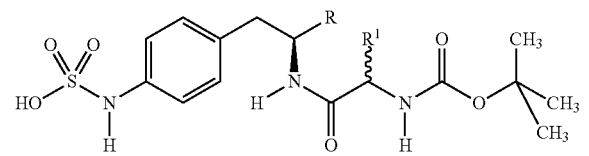

wherein R is a substituted or unsubstituted thiazol-2-yl unit and non-limiting examples of R and R¹ and the stereochemistry at R¹ are further described in Table I.

TABLE I

| No. | R | R¹ |
|---|---|---|
| 1 | thiazol-2-yl | (S)-benzyl |
| 2 | 4-methylthiazol-2-yl | (S)-benzyl |
| 3 | 4-ethylthiazol-2-yl | (S)-benzyl |
| 4 | 4-propylthiazol-2-yl | (S)-benzyl |
| 5 | 4-iso-propylthiazol-2-yl | (S)-benzyl |
| 6 | 4-cyclopropylthiazol-2-yl | (S)-benzyl |
| 7 | 4-butylthiazol-2-yl | (S)-benzyl |
| 8 | 4-tert-butylthiazol-2-yl | (S)-benzyl |
| 9 | 4-cyclohexylthiazol-2-yl | (S)-benzyl |
| 10 | 4-(2,2,2-trifluoroethyl)thiazol-2-yl | (S)-benzyl |
| 11 | 4-(3,3,3-trifluoropropyl)thiazol-2-yl | (S)-benzyl |
| 12 | 4-(2,2-difluorocyclopropyl)thiazol-2-yl | (S)-benzyl |
| 13 | 4-(methoxymethyl)thiazol-2-yl | (S)-benzyl |
| 14 | 4-(carboxylic acid ethyl ester)thiazol-2-yl | (S)-benzyl |
| 15 | 4,5-dimethylthiazol-2-yl | (S)-benzyl |
| 16 | 4-methyl-5-ethylthiazol-2-yl | (S)-benzyl |
| 17 | 4-phenylthiazol-2-yl | (S)-benzyl |
| 18 | 4-(4-chlorophenyl)thiazol-2-yl | (S)-benzyl |
| 19 | 4-(3,4-dimethylphenyl)thiazol-2-yl | (S)-benzyl |
| 20 | 4-methyl-5-phenylthiazol-2-yl | (S)-benzyl |
| 21 | 4-(thiophene-2-yl)thiazol-2-yl | (S)-benzyl |
| 22 | 4-(thiophene-3-yl)thiazol-2-yl | (S)-benzyl |
| 23 | 4-(5-chlorothiophene-2-yl)thiazol-2-yl | (S)-benzyl |
| 24 | 5,6-dihydro-4H-cyclopenta[d]thiazol-2-yl | (S)-benzyl |
| 25 | 4,5,6,7-tetrahydrobenzo[d]thiazol-2-yl | (S)-benzyl |

The compounds encompassed within the first aspect of Category I of the present disclosure can be prepared by the procedure outlined in Scheme I and described in Example 1 herein below.

Scheme I

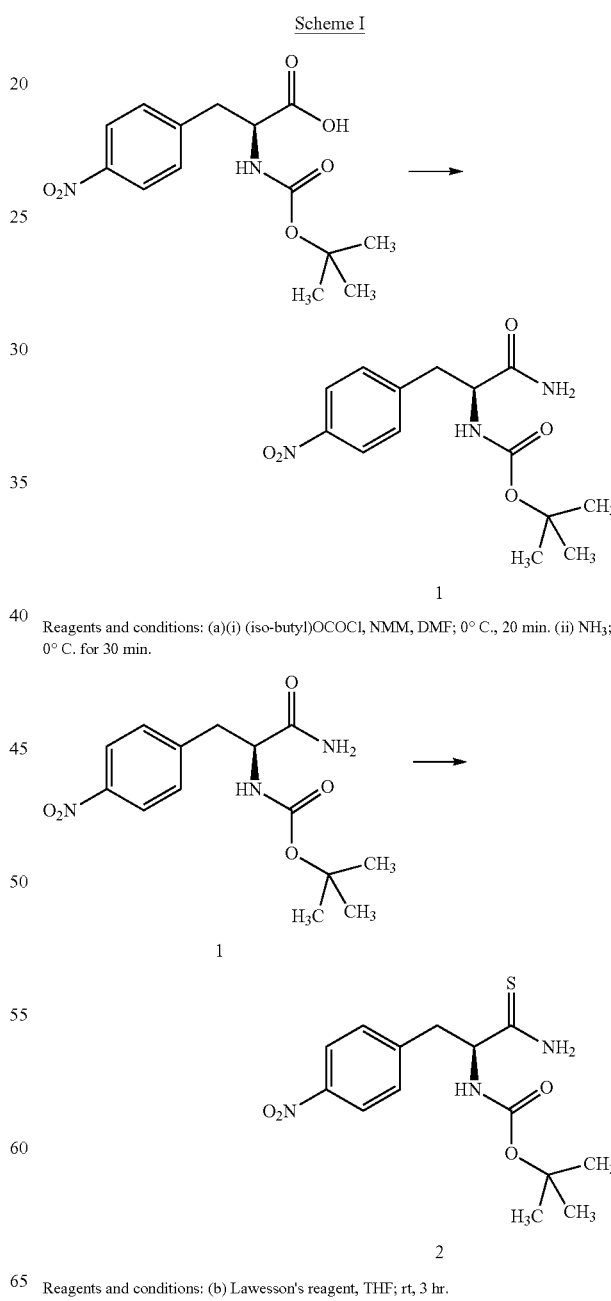

Reagents and conditions: (a)(i) (iso-butyl)OCOCl, NMM, DMF; 0° C., 20 min. (ii) NH₃; 0° C. for 30 min.

Reagents and conditions: (b) Lawesson's reagent, THF; rt, 3 hr.

-continued

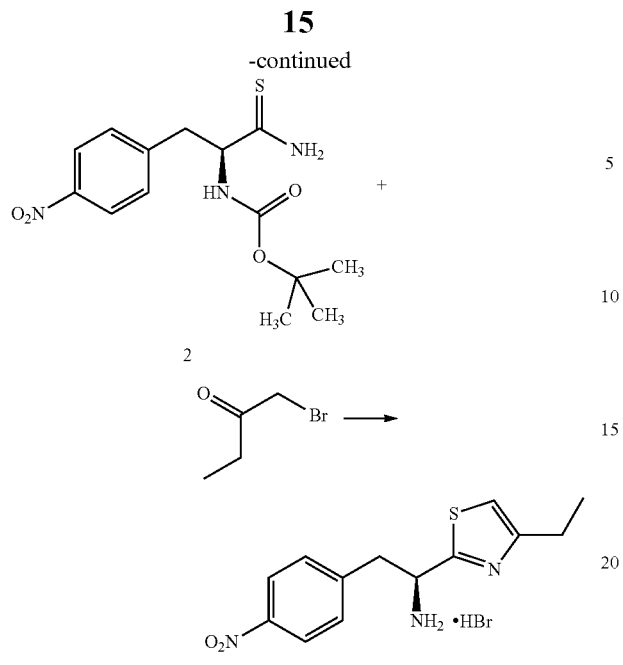

Reagents and conditions: (c) CH₃CN; reflux, 3 hr.

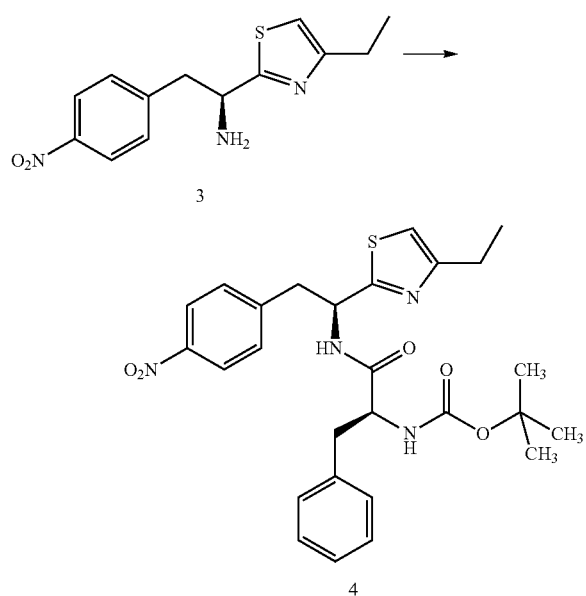

Reagents and conditions: (d) Boc-Phe, EDCI, HOBt, DIPEA, DMF; rt, 18 hr.

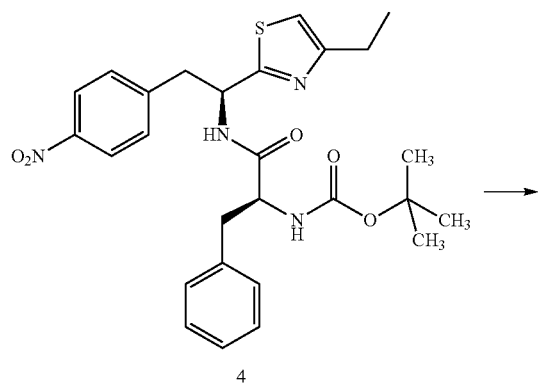

-continued

Reagents and conditions: (e) (i) H₂:Pd/C, MeOH; (ii) SC₃-pyridine, NH₄OH; rt, 2 hr.

Example 1

4-{(S)-2-[(S)-2-(tert-Butoxycarbonylamino)-3-phenylpropanamido]-2-(4-ethylthiazol-2-yl)ethyl}phenylsulfamic acid (5)

Preparation of [1-(S)-carbamoyl-2-(4-nitrophenyl)ethyl-carbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes after which NH₃ (g) is passed through the reaction mixture for 30 minutes at 0° C. The reaction mixture is concentrated and the residue dissolved in EtOAc, washed successively with 5% citric acid, water, 5% NaHCO₃, water and brine, dried (Na₂SO₄), filtered and concentrated in vacuo to a residue that is triturated with a mixture of EtOAc/petroleum ether to provide 2.2 g (74%) of the desired product as a white solid.

Preparation of [2-(4-nitrophenyl)-1-(S)-thiocarbamoyl-ethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue which is purified over silica to provide 0.350 g (83%) of the desired product. ¹H NMR (300 MHz, CDCl₃) δ 8.29 (s, 1H), 8.10 (d, J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine (3): A mixture of [2-(4-nitrophenyl)-1-(S)-thiocarbamoylethyl]-carbamic acid tert-butyl ester, 2, (0.245 g, 0.753 mmol), 1-bromo-2-butanone (0.125 g, 0.828 mmol) in CH₃CN (5 mL) is refluxed 3 hours. The reaction mixture is cooled to room temperature and diethyl ether is added to the solution and the precipitate which forms is removed by filtration. The solid is dried under vacuum to afford 0.242 g (90% yield) of the desired product. ESI+MS 278 (M+1).

Preparation of {1-[1-(4-ethylthiazol-2-yl)-2-(4-nitrophenyl)ethylcarbamoyl]-2-phenylethyl}carbamic acid tert-butyl ester (4): To a solution of 1-(S)-(4-ethylthiazol-2-yl)-2-(4-nitrophenyl)ethyl amine hydrobromide, 3, (0.393 g, 1.1 mmol), (S)-(2-tert-butoxycarbonylamino)-3-phenylpropionic acid (0.220 g, 0.828 mmol) and 1-hydroxybenzotriazole (HOBt) (0.127 g, 0.828 mmol) in DMF (10 mL) at 0° C., is added 1-(3-dimethylaminopropyl)-3-ethylcarbodiimide (EDCI) (0.159 g, 0.828 mmol) followed by diisopropylamine (0.204 g, 1.58 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.345 g of the desired product which is used without further purification. LC/MS ESI+525 (M+1).

Preparation of 4-{(S)-2-[(S)-2-(tert-butoxycarbonylamino)-3-phenylpropan-amido]-2-(4-ethylthiazol-2-yl)ethyl}phenylsulfamic acid (5): {1-[1-(4-ethylthiazol-2-yl)-2-(4-nitrophenyl)ethylcarbamoyl]-2-phenylethyl}carbamic acid tert-butyl ester, 4, (0.345 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO$_3$-pyridine (0.314 g). The reaction is stirred at room temperature for 5 minutes after which a 7% solution of NH$_4$OH (50 mL) is added. The mixture is then concentrated and the resulting residue is purified by reverse phase chromatography to afford 0.222 g of the desired product as the ammonium salt. $^1$H(CD$_3$OD): δ 7.50-6.72 (m, 10H), 5.44-5.42 (d, 1H, J=6.0 Hz), 4.34 (s, 1H), 3.34-2.79 (m, 4H), 2.83-2.76 (q, 2H, J=7.2 Hz), 1.40 (s, 9H), 1.31 (t, 3H, J=7.5 Hz).

The final compounds of the present disclosure can also be isolated as the free acid. A non-limiting example of this procedure is described herein below in Example 4.

The following are non-limiting examples of compounds encompassed within the first aspect of Category I of the present disclosure.

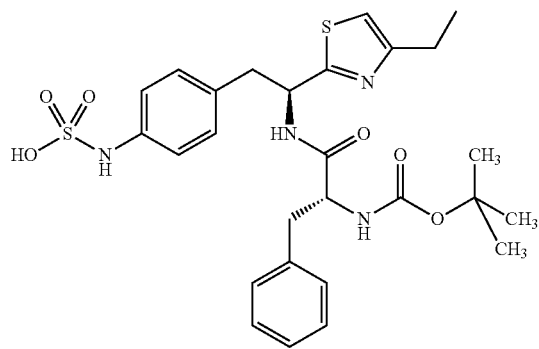 [SMILES: CCc1csc([C@H](Cc2ccc(NS(=O)(=O)O)cc2)NC(=O)[C@@H](Cc2ccccc2)NC(=O)OC(C)(C)C)n1]

4-{(S)-2-[(R)-2-(tert-butoxycarbonylamino)-3-phenylpropanamido]-2-(4-ethylthiazol-2-yl)ethyl}phenylsulfamic acid: $^1$H(CD$_3$OD): δ 7.22-7.02 (m, 10H), 5.39 (s, 1H), 4.34 (s, 1H), 3.24-2.68 (m, 6H), 1.37 (s, 9H), 1.30 (t, 3H, J=7.5 Hz).

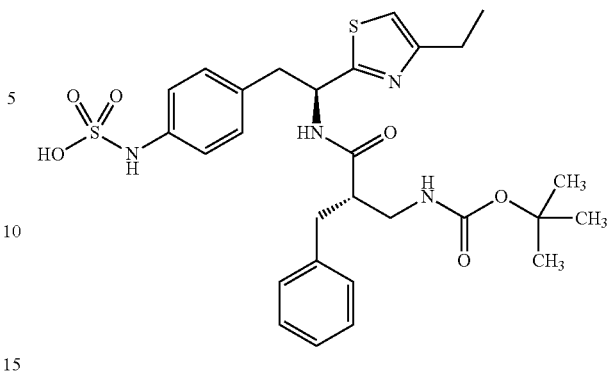

{1-[1-(5-Ethylthiazol-2-yl)-(S)-2-(4-sulfoaminophenyl)ethylcarbamoyl]-(S)-2-phenylethyl}methyl carbamic acid tert-butyl ester: $^1$H NMR (300 MHz, MeOH-d$_4$) δ 8.36 (d, J=8.1 Hz, 1H), 7.04-7.22 (m, 9H), 5.45 (s, 1H), 3.01-3.26 (m, 2H), 2.60-2.88 (m, 4H), 2.33 (s, 3H), 1.30 (s, 9H).

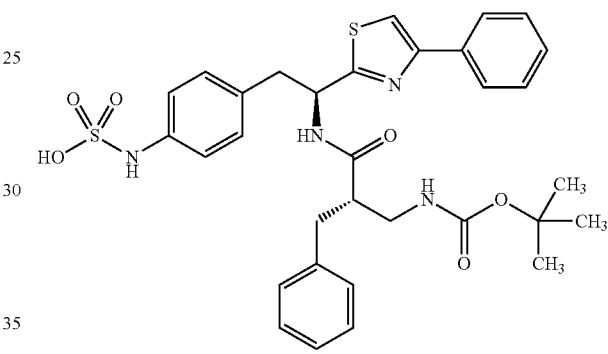

{1-[1-(5-Phenylthiazol-2-yl)-(S)-2-(4-sulfoaminophenyl)ethylcarbamoyl]-(S)-2-phenylethyl}methyl carbamic acid tert-butyl ester: $^1$H NMR (300 MHz, MeOH-d$_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The second aspect of Category I of the present disclosure relates to compounds having the formula:

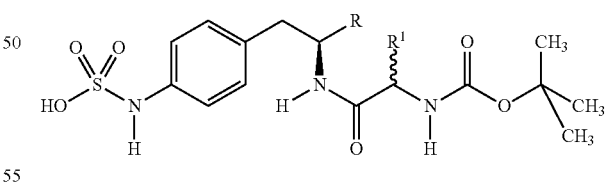

wherein R is a substituted or unsubstituted thiazol-4-yl unit and non-limiting examples of R and R$^1$ and the stereochemistry at R$^1$ are further described in Table II.

TABLE II

| No. | R | R$^1$ |
|---|---|---|
| 26 | thiazol-4-yl | (S)-benzyl |
| 27 | 2-methylthiazol-4-yl | (S)-benzyl |
| 28 | 2-ethylthiazol-4-yl | (S)-benzyl |
| 29 | 2-propylthiazol-4-yl | (S)-benzyl |

TABLE II-continued

| No. | R | R¹ |
|---|---|---|
| 30 | 2-iso-propylthiazol-4-yl | (S)-benzyl |
| 31 | 2-cyclopropylthiazol-4-yl | (S)-benzyl |
| 32 | 2-butylthiazol-4-yl | (S)-benzyl |
| 33 | 2-tert-butylthiazol-4-yl | (S)-benzyl |
| 34 | 2-cyclohexylthiazol-4-yl | (S)-benzyl |
| 35 | 2-(2,2,2-trifluoroethyl)thiazol-4-yl | (S)-benzyl |
| 36 | 2-(3,3,3-trifluoropropyl)thiazol-4-yl | (S)-benzyl |
| 37 | 2-(2,2-difluorocyclopropyl)thiazol-4-yl | (S)-benzyl |
| 38 | 2-phenylthiazol-4-yl | (S)-benzyl |
| 39 | 2-(4-chlorophenyl)thiazol-4-yl | (S)-benzyl |
| 40 | 2-(3,4-dimethylphenyl)thiazol-4-yl | (S)-benzyl |
| 41 | 2-(thiophene-2-yl)thiazol-4-yl | (S)-benzyl |
| 42 | 2-(thiophene-3-yl)thiazol-4-yl | (S)-benzyl |
| 43 | 2-(3-chlorothiophene-2-yl)thiazol-4-yl | (S)-benzyl |
| 44 | 2-(3-methylthiophene-2-yl)thiazol-4-yl | (S)-benzyl |
| 45 | 2-(2-methylthiazol-4-yl)thiazol-4-yl | (S)-benzyl |
| 46 | 2-(furan-2-yl)thiazol-4-yl | (S)-benzyl |
| 47 | 2-(pyrazin-2-yl)thiazol-4-yl | (S)-benzyl |
| 48 | 2-[(2-methyl)pyridin-5-yl]thiazol-4-yl | (S)-benzyl |
| 49 | 2-(4-chlorobenzenesulfonylmethyl)thiazol-4-yl | (S)-benzyl |
| 50 | 2-(tert-butylsulfonylmethyl)thiazol-4-yl | (S)-benzyl |

The compounds encompassed within the second aspect of Category I of the present disclosure can be prepared by the procedure outlined in Scheme II and described in Example 2 herein below.

Scheme II

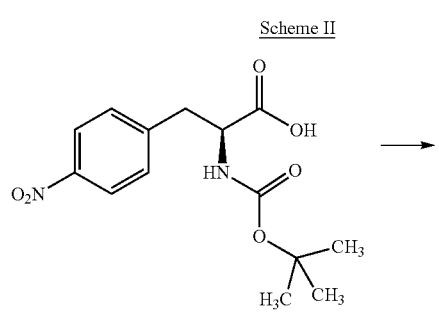

6

Reagents and conditions: (a)(i) (iso-butyl)OCOCl, Et₃N, THF; 0° C., 20 min. (ii) CH₂N₂; room temp for 3 hours.

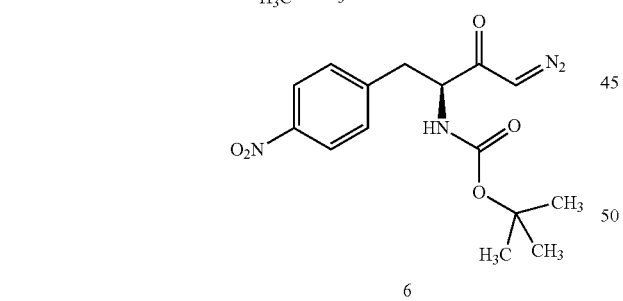

6

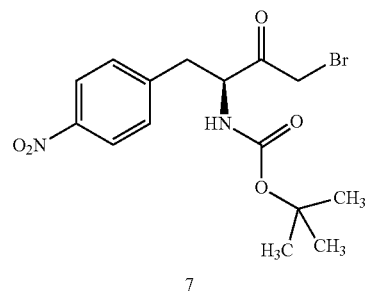

7

Reagents and conditions: (b) 48% HBr, THF; 0° C., 1.5 hr.

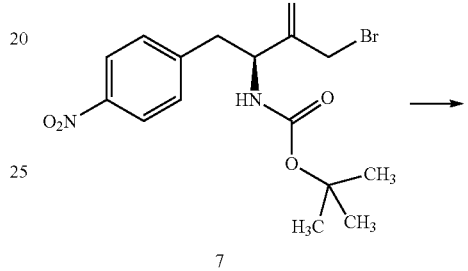

7

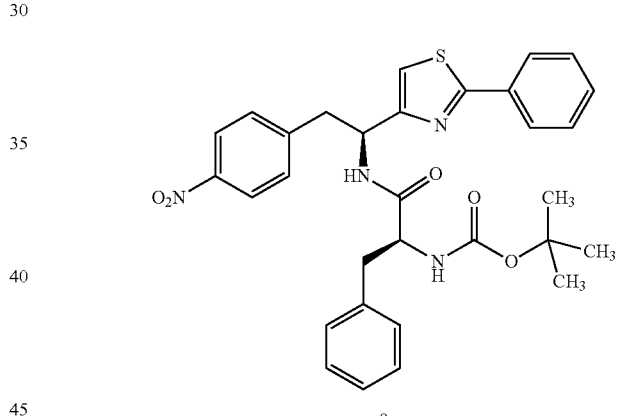

8

Reagents and conditions: (c)(i) thiobenzamide, CH₃CN; reflux, 2 hr.
(ii) Boc-Phe, HOBt, DIPEA, DMF; rt, 18 hr.

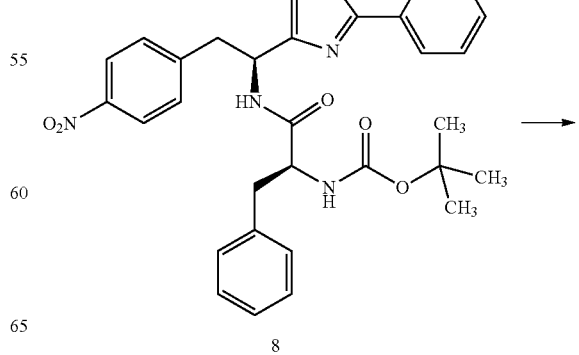

8

-continued

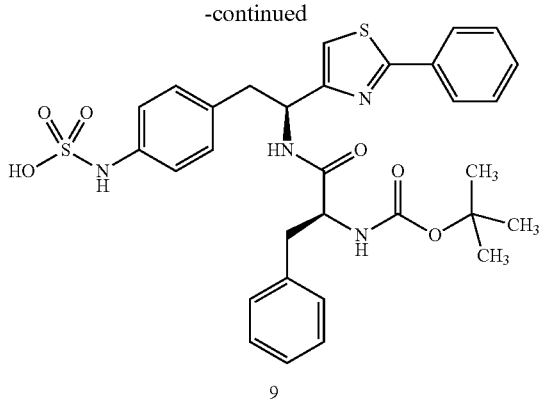

9

Reagents and conditions: (d) (i) H₂:Pd/C, MeOH; (ii) SO₃-pyridine, NH₄OH; rt, 12 hr.

Example 2

4-{(S)-2-(S)-2-(tert-Butoxycarbonylamino)-3-phenylpropanamido-2-(2-phenylthiazol-4-yl)ethyl}phenylsulfamic acid (9)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by isobutyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried (Na₂SO₄), filtered and concentrated. The residue is purified over silica (hexane/EtOAc 2:1) to afford 1.1 g (82% yield) of the desired product as a slightly yellow solid. $^1$H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. Na₂CO₃. The mixture is extracted with EtOAc (3×25 mL) and the combined organic extracts are washed with brine, dried (Na₂SO₄), filtered and concentrated to obtain 0.400 g of the product which is used in the next step without further purification. $^1$H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of tert-butyl (S)-1-(S)-2-(4-nitrophenyl)-1-(2-phenylthiazole-4-yl)ethylamino-1-oxo-3-phenylpropan-2-ylcarbamate (8): A mixture of thiobenzamide (0.117 g, 0.85 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed 2 hours. The reaction mixture is cooled to room temperature and diethyl ether is added to precipitate the intermediate 2-(nitrophenyl)-(S)-1-(4-phenylthiazol-2-yl)ethylamine which is isolated by filtration as the hydrobromide salt. The hydrobromide salt is dissolved in DMF (3 mL) together with diisoproylethylamine (0.42 mL, 2.31 mmol), 1-hydroxybenzotriazole (0.118 g, 0.79 mmol) and (S)-(2-tert-butoxycarbonylamino)-3-phenylpropionic acid (0.212 g, 0.80 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.395 g (90% yield) of the desired product which is used without further purification. LC/MS ESI+573 (M+1).

Preparation of 4-{(S)-2-(S)-2-(tert-butoxycarbonylamino)-3-phenylpropane-amido-2-(2-phenylthiazole-4-yl)}phenylsulfamic acid (9): tert-butyl (S)-1-(S)-2-(4-nitrophenyl)-1-(2-phenylthiazole-4-yl)ethylamino-1-oxo-3-phenylpropan-2-ylcarbamate, 8, (0.360 g) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.296 g). The reaction is stirred at room temperature for 5 minutes after which a 7% solution of NH₄OH (10 mL) is added. The mixture is then concentrated and the resulting residue is purified by reverse phase chromatography to afford 0.050 g of the desired product as the ammonium salt. $^1$H NMR (300 MHz, MeOH-d₄) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The first aspect of Category II of the present disclosure relates to compounds having the formula:

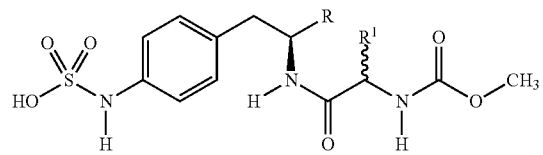

wherein R is a substituted or unsubstituted thiazol-2-yl unit and non-limiting examples of R and R¹ and the stereochemistry at R¹ are further described in Table III.

TABLE III

| No. | R | R¹ |
| --- | --- | --- |
| 51 | thiazol-2-yl | (S)-benzyl |
| 52 | 4-methylthiazol-2-yl | (S)-benzyl |
| 53 | 4-ethylthiazol-2-yl | (S)-benzyl |
| 54 | 4-propylthiazol-2-yl | (S)-benzyl |
| 55 | 4-iso-propylthiazol-2-yl | (S)-benzyl |
| 56 | 4-cyclopropylthiazol-2-yl | (S)-benzyl |
| 57 | 4-butylthiazol-2-yl | (S)-benzyl |
| 58 | 4-tert-butylthiazol-2-yl | (S)-benzyl |
| 59 | 4-cyclohexylthiazol-2-yl | (S)-benzyl |
| 60 | 4-(2,2,2-trifluoroethyl)thiazol-2-yl | (S)-benzyl |
| 61 | 4-(3,3,3-trifluoropropyl)thiazol-2-yl | (S)-benzyl |
| 62 | 4-(2,2-difluorocyclopropyl)thiazol-2-yl | (S)-benzyl |
| 63 | 4-(methoxymethyl)thiazol-2-yl | (S)-benzyl |
| 64 | 4-(carboxylic acid ethyl ester)thiazol-2-yl | (S)-benzyl |
| 65 | 4,5-dimethylthiazol-2-yl | (S)-benzyl |
| 66 | 4-methyl-5-ethylthiazol-2-yl | (S)-benzyl |
| 67 | 4-phenylthiazol-2-yl | (S)-benzyl |
| 68 | 4-(4-chlorophenyl)thiazol-2-yl | (S)-benzyl |
| 69 | 4-(3,4-dimethylphenyl)thiazol-2-yl | (S)-benzyl |
| 70 | 4-methyl-5-phenylthiazol-2-yl | (S)-benzyl |

TABLE III-continued

| No. | R | R¹ |
|-----|---|-----|
| 71 | 4-(thiophene-2-yl)thiazol-2-yl | (S)-benzyl |
| 72 | 4-(thiophene-3-yl)thiazol-2-yl | (S)-benzyl |
| 73 | 4-(5-chlorothiophene-2-yl)thiazol-2-yl | (S)-benzyl |
| 74 | 5,6-dihydro-4H-cyclopenta[d]thiazol-2-yl | (S)-benzyl |
| 75 | 4,5,6,7-tetrahydrobenzo[d]thiazol-2-yl | (S)-benzyl |

The compounds encompassed within the first aspect of Category II of the present disclosure can be prepared by the procedure outlined in Scheme III and described in Example 3 herein below.

Scheme III

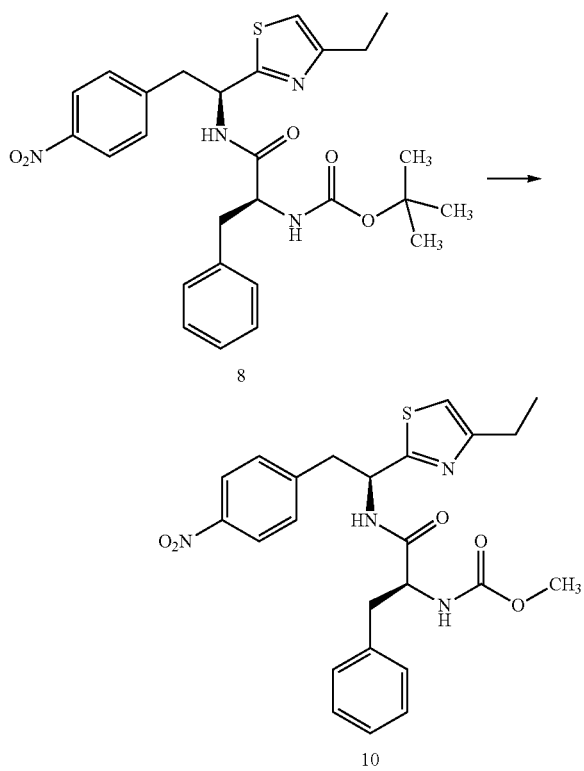

Reagents and conditions: (a)(i) 4M HCl, dioxane; rt, 1 hr;
(ii) methyl chloroformate, pyridine, CHCl₃, 0° C. to rt, 48 hr.

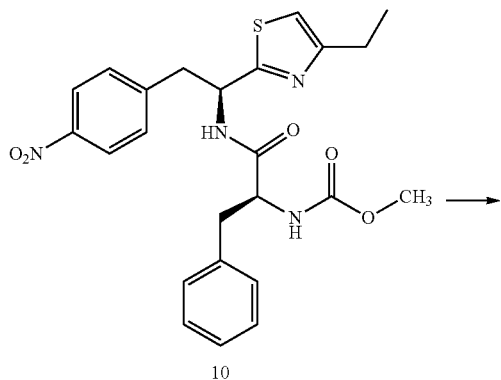

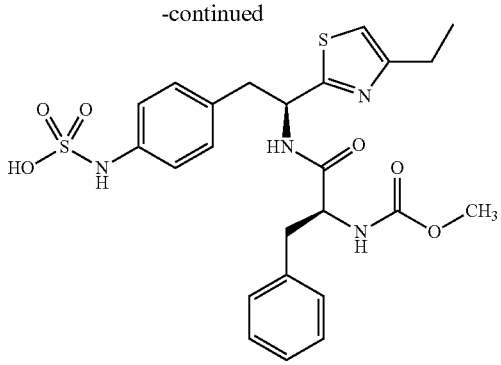

Reagents and conditions: (b) (i) H₂:Pd/C, MeOH; (ii) SO₃-pyridine, NH₄OH; rt, 4 hr.

Example 3

4-{(S)-2-(4-Ethylthiazol-2-yl)-2-[(S)-2-(methoxycarbonylamino)-3-phenylpropanamido]ethyl}phenylsulfamic acid (11)

Preparation of methyl-(S)-1-[(S)-1-(4-ethylthiazol-2-yl)-2-(4-nitrophenyl)ethyl-amino]-1-oxo-3-phenylpropan-2-yl-carbamate (10): tert-butyl (S)-1-[(S)-1-(4-ethylthiazol-2-yl)-2-(4-nitrophenyl)ethylamino]-1-oxo-3-phenylpropan-2-ylcarbamate, 8, (0.460 mg, 0.881 mmol) is dissolved in a solution of 4M hydrogen chloride in 1,4-dioxane (4 mL). The reaction mixture is stirred 1 hour, and the solvent is removed under reduced pressure. The resulting crude amine is dissolved in CHCl₃ (8 mL) and pyridine (1 mL) is added. The temperature is cooled to 0° C. and methyl chloroformate (0.083 g, 0.881 mmol) is added dropwise. The reaction mixture is allowed to warm to room temperature and stirred for 2 days. Water is added, the solution stirred for 15 minutes and then extracted several times with CHCl₃. The combined organic layers are washed with 1N HCl, 5% NaHCO₃, and brine, dried over Na₂SO₄, and filtered. The solvent is removed in vacuo to afford 0.297 g of the desired product.

Preparation of 4-{(S)-2-(4-ethylthiazol-2-yl)-2-[(S)-2-(methoxycarbonylamino)-3-phenylpropanamido]ethyl}phenylsulfamic acid (11): Methyl-(S)-1-[(S)-1-(4-ethyl-thiazol-2-yl)-2-(4-nitrophenyl)ethyl-amino]-1-oxo-3-phenylpropan-2-ylcarbamate, 10, (0.297 g) is dissolved in MeOH (4 mL). A catalytic amount of Pd/C (10% w/w) is added and the mixture is stirred under a hydrogen atmosphere 4 hours. The reaction mixture is filtered through a bed of CELITE™ and the solvent is removed under reduced pressure. The crude product is dissolved in pyridine (12 mL) and treated with SO₃-pyridine (0.196 g). The reaction is stirred at room temperature for 5 minutes after which a 7% solution of NH₄OH (25 mL) is added. The mixture is then concentrated and the resulting residue is purified by reverse phase chromatography silica to afford 0.172 g of the desired product as the ammonium salt. $^1$H(CD₃OD): δ 7.26-7.00 (m, 10H), 5.39 (t, 1H, J=5.7 Hz), 4.38 (t, 1H, J=5.7 Hz), 3.62 (s, 3H), 3.34-2.75 (m, 6H), 1.30 (t, 3H, J=7.5 Hz).

The following are non-limiting examples of the first aspect of Category II of the present disclosure.

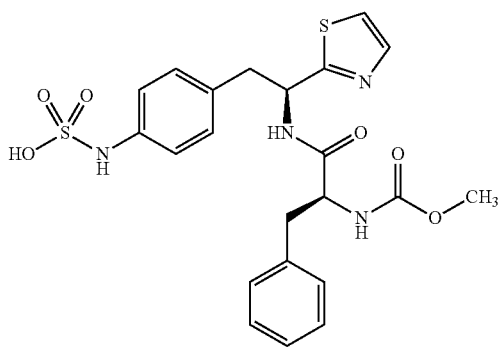 [SMILES: COC(=O)N[C@@H](Cc1ccccc1)C(=O)N[C@@H](Cc1ccc(NS(=O)(=O)O)cc1)c1nccs1]

4-{(S)-2-[(S)-2-(Methoxycarbonylamino)-3-phenylpropanamido]-2-(thiazol-2-yl)ethyl}phenylsulfamic acid: ¹H(CD₃OD): δ 7.78-7.75 (m, 1H), 7.51-7.47 (m, 1H), 7.30-7.02 (m, 9H), 5.49-5.43 (m, 1H), 4.39 (t, 1H, J=8.1 Hz), 356 (s, 3H), 3.51-2.71 (m, 4H).

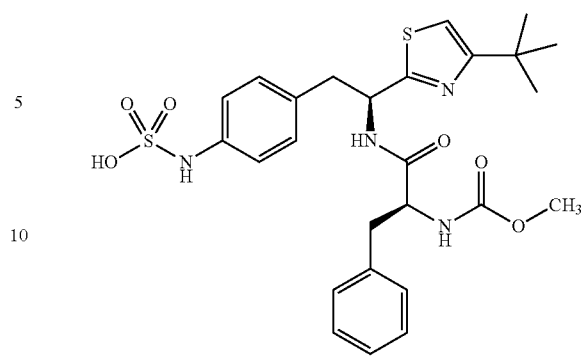

4-{(S)-2-(4-tert-Butylthiazol-2-yl)-2-[(S)-2-(methoxycarbonylamino)-3-phenylpropanamido]ethyl}phenylsulfamic acid: ¹H NMR (300 MHz, CD₃OD): δ 7.23-7.19 (m, 5H), 7.10-6.98 (m, 5H), 5.42-5.38 (m, 1H), 4.37 (dd, J=8.4, 5.4 Hz, 1H), 3.61 (s, 2H), 3.48 (bs, 1H), 3.32-3.25 (m, 1H), 3.13-3.07 (m, 2H), 2.77 (dd, J=13.5, 9.3 Hz, 1H), 1.36 (s, 9H).

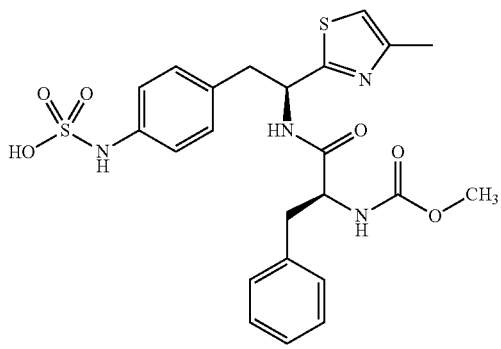 [SMILES: COC(=O)N[C@@H](Cc1ccccc1)C(=O)N[C@@H](Cc1ccc(NS(=O)(=O)O)cc1)c1nc(C)cs1]

4-{(S)-2-[(S)-2-(Methoxycarbonylamino)-3-phenylpropanamido]-2-(4-methylthiazol-2-yl)ethyl}phenylsulfamic acid: ¹H NMR (300 MHz, CD₃OD): δ 8.52-8.49 (m, 1H), 7.20-6.99 (m, 10H), 5.37 (bs, 1H), 4.36 (bs, 1H), 3.62-3.48 (m, 3H), 3.32-3.22 (m, 1H), 3.11-3.01 (m, 2H), 2.80-2.72 (m, 1H), 2.42 (s, 3H).

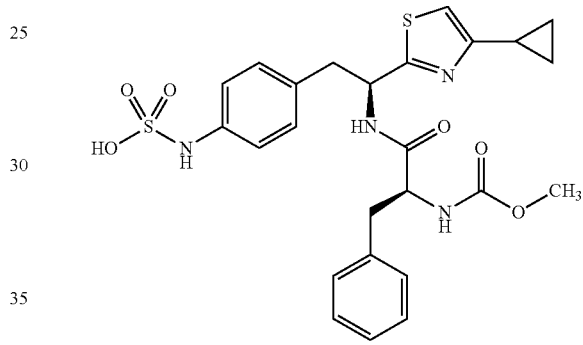

4-{(S)-2-(4-Cyclopropylthiazol-2-yl)-2-[(S)-2-(methoxycarbonylamino)-3-phenylpropanamido]ethyl}phenylsulfamic acid: ¹H(CD₃OD): δ 7.13-6.91 (m, 10H), 6.81 (s, 1H), 5.23 (t, 1H, J=7.8 Hz), 4.24 (t, 1H, J=8.4 Hz), 3.50 (s, 3H), 3.12-2.66 (m, 4H), 1.94 (t, 1H, J=5.1 Hz), 0.84-0.73 (m, 4H).

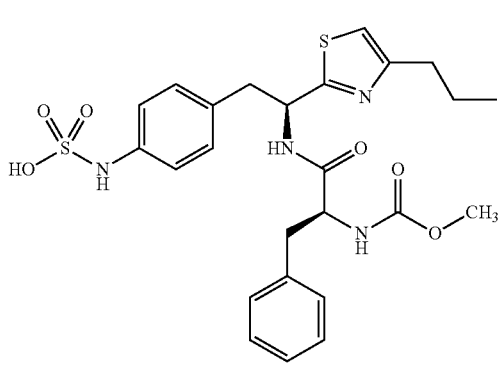 [SMILES: CCCc1csc([C@H](Cc2ccc(NS(=O)(=O)O)cc2)NC(=O)[C@H](Cc2ccccc2)NC(=O)OC)n1]

4-{(S)-2-[(S)-2-(methoxycarbonylamino)-3-phenylpropanamido]-2-(4-propylthiazol-2-yl)ethyl}phenylsulfamic acid: ¹H NMR (300 MHz, CD₃OD): δ 8.51-8.49 (m, 1H), 7.22-6.99 (m, 10H), 5.39 (t, J=6.0 Hz, 1H), 4.38 (dd, J=14.4, 9.0 Hz, 1H), 3.62 (s, 2H), 3.59-3.48 (m, 1H), 3.27 (dd, J=13.5, 6.3 Hz, 1H), 3.12-3.02 (m, 2H), 2.81-2.71 (m, 3H), 1.81-1.68 (m, 2H), 0.985 (t, J=7.5 Hz, 3H).

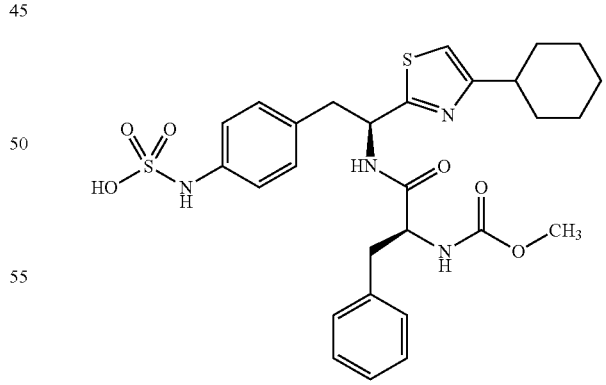

4-{(S)-2-(4-Cyclohexylthiazol-2-yl)-2-[(S)-2-(methoxycarbonylamino)-3-phenyl-propanamido]ethyl}phenylsulfamic acid: ¹H NMR (300 MHz, CD₃OD): δ 7.21-6.97 (m, 10H), 5.45-5.25 (m, 1H), 5.42-5.36 (m, 1H), 5.10-5.02 (m, 1H), 4.03-4.35 (m, 1H), 3.63 (m, 2H), 3.60-3.49 (m, 1H), 3.12-3.06 (m, 1H), 2.95 (dd, J=14.1, 9.9 Hz, 1H), 2.82-2.72 (m, 2H), 2.07-1.77 (m, 3H), 1.56-1.31 (m, 10H).

7.40 (d, J=11.1 Hz, 1H), 7.30-7.15 (m, 5H), 7.12-7.00 (m, 5H), 5.41 (dd, J=8.4, 5.1 Hz, 1H), 4.42-4.36 (m, 1H), 3.77-3.52 (m, 5H), 3.33-3.23 (m, 1H), 3.15-3.02 (m, 2H), 2.97-2.91 (m, 1H), 2.82-2.70 (m, 1H).

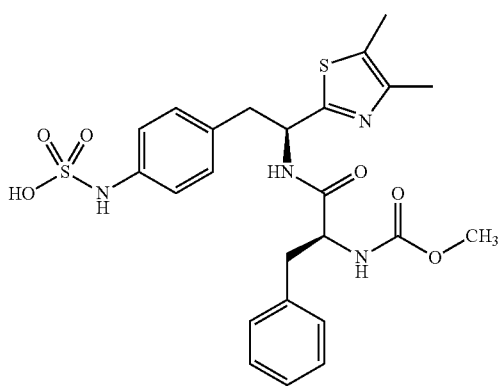 [SMILES: COC(=O)N[C@@H](Cc1ccccc1)C(=O)N[C@@H](Cc1ccc(NS(=O)(=O)O)cc1)c1nc(C)c(C)s1]

4-{(S)-2-(4,5-Dimethylthiazol-2-yl)-2-[(S)-2-(methoxycarbonylamino)-3-phenyl-propanamido]ethyl}phenylsulfamic acid: $^1$H NMR (300 MHz, CD$_3$OD): δ 8.45 (d, J=7.8 Hz, 1H), 7.22-7.03 (m, 9H), 5.28 (t, J=7.2 Hz, 1H), 4.36 (t, J=7.8 Hz, 1H), 3.62 (s, 2H), 3.52-3.46 (m, 1H), 3.22 (dd, J=14.1, 6.3 Hz, 1H), 3.07-2.99 (m, 2H), 2.77 (dd, J=13.5, 8.4 Hz, 1H), 2.32 (s, 3H), 2.30 (s, 3H).

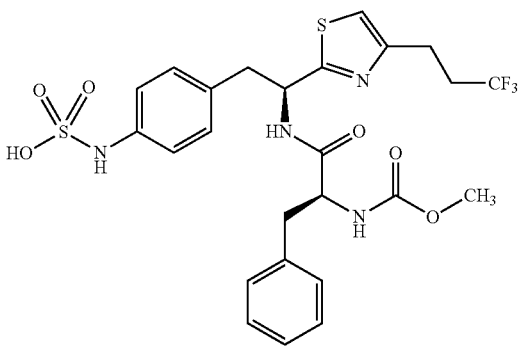

4-{(S)-2-[(S)-2-(Methoxycarbonylamino)-3-phenylpropanamido)-2-[4-(3,3,3-trifluoropropyl)thiazol-2-yl]ethyl}phenylsulfamic acid: $^1$H NMR (300 MHz, CD$_3$OD): δ 7.23-7.03 (m, 10H), 5.46-5.34 (m, 1H), 4.54-4.44 (m, 1H), 3.63 (s, 2H), 3.62-3.35 (m, 1H), 3.34-3.24 (m, 1H), 3.17-2.99 (m, 4H), 2.82-2.74 (m, 1H), 2.69-2.56 (m, 2H).

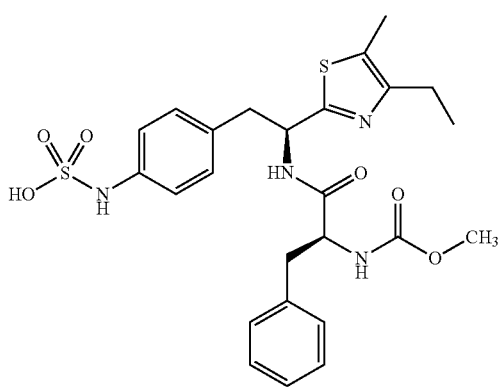 [SMILES: CCc1nc([C@H](Cc2ccc(NS(=O)(=O)O)cc2)NC(=O)[C@H](Cc2ccccc2)NC(=O)OC)sc1C]

4-{(S)-2-(4-Ethyl-5-methylthiazol-2-yl)-2-[(S)-2-(methoxycarbonylamino)-3-phenyl-propanamido]ethyl}phenylsulfamic acid: $^1$H NMR (300 MHz, CD$_3$OD): δ 8.45 (d, J=8.1 Hz, 1H), 7.36-7.00 (m, 9H), 5.31 (bs, 1H), 4.37 (bs, 1H), 3.62-3.46 (m, 3H), 3.28-2.64 (m, 6H), 2.34 (d, J=5.4 Hz, 3H), 1.37-1.20 (m, 3H).

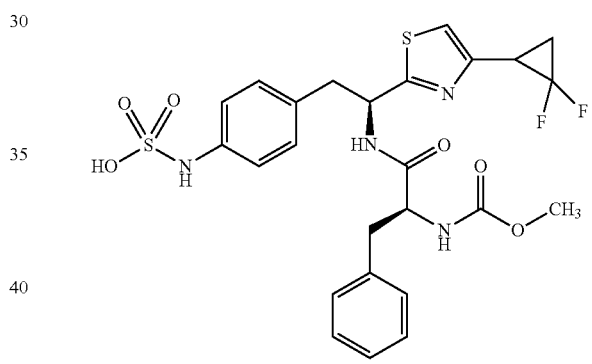

4-{(S)-2-[4-(2,2-Difluorocyclopropyl)thiazol-ylmethoxycarbonyl-amino)-3-phenylpropanamido]ethyl}phenylsulfamic acid: $^1$H NMR (300 MHz, CD$_3$OD): δ 7.28-7.00 (m, 10H), 5.42-5.37 (m, 1H), 4.41-4.38 (m, 1H), 3.60 (s, 2H), 3.61-3.52 (m, 1H), 3.35-3.23 (m, 1H), 3.04-2.91 (m, 2H), 2.78-2.68 (m, 1H), 1.99-1.90 (m, 2H).

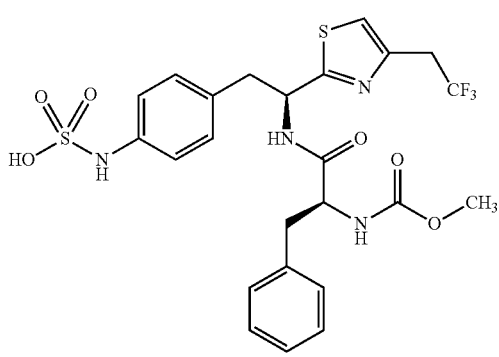 [SMILES: COC(=O)N[C@@H](Cc1ccccc1)C(=O)N[C@@H](Cc1ccc(NS(=O)(=O)O)cc1)c1nc(CC(F)(F)F)cs1]

4-{(S)-2-[(S)-2-(Methoxycarbonylamino)-3-phenylpropanamido]-2-[4-(2,2,2-trifluoroethyl)thiazol-2-yl]ethyl}phenylsulfamic acid: $^1$H NMR (300 MHz, CD$_3$OD): δ

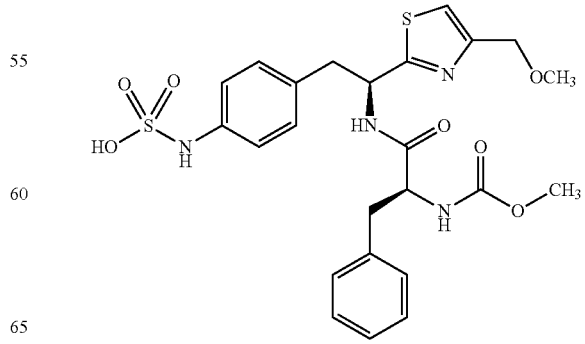

4-{(S)-2-[(S)-2-(Methoxycarbonylamino)-3-phenylpropanamido]-2-[4-(methoxy-methyl)thiazol-2-yl]ethyl}phenylsulfamic acid: $^1$H NMR (300 MHz, CD$_3$OD): δ 8.55 (d, J=6.6 Hz, 1H), 7.31 (s, 1H), 7.21-7.05 (m, 9H), 5.41 (bs, 1H), 4.53 (s, 2H), 4.37 (bs, 1H), 3.62 (s, 2H), 3.59-3.46 (m, 1H), 3.41 (s, 3H), 3.28-3.22 (m, 1H), 3.13-3.00 (m, 3H), 2.80-2.72 (m, 1H).

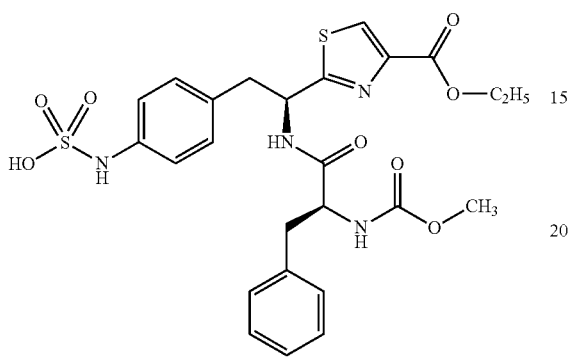

4-{(S)-2-(4-(Ethoxycarbonyl)thiazol-2-yl)-2-[(S)-2-(methoxycarbonylamino)-3-phenylpropanamido]ethyl}phenylsulfamic acid: $^1$H NMR (300 MHz, CD$_3$OD): δ 8.25 (s, 1H), 7.20-7.07 (m, 10H), 5.40 (dd, J=7.5 Hz, 1H), 4.45-4.36 (m, 3H), 3.63 (s, 2H), 3.60-3.51 (m, 1H), 3.34-3.27 (m, 1H), 3.17-3.00 (m, 2H), 2.79 (dd, J=13.5, 8.4 Hz, 1H), 1.42 (t, J=7.5 Hz, 3H).

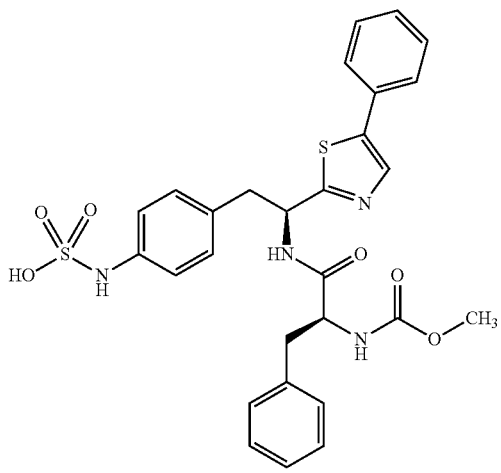 [SMILES: COC(=O)N[C@@H](Cc1ccccc1)C(=O)N[C@@H](Cc1ccc(NS(=O)(=O)O)cc1)c1ncc(-c2ccccc2)s1]

4-{(S)-2-[(S)-2-(Methoxycarbonylamino)-3-phenylpropanamido]-2-(5-phenylthiazol-2-yl))ethyl}phenylsulfamic acid: $^1$H NMR (300 MHz, CD$_3$OD): δ 8.63 (d, J=8.1 Hz, 1H), 7.96 (s, 1H), 7.59 (d, J=7.8 Hz, 2H), 7.47-7.36 (m, 3H), 7.19-7.10 (m, 10H), 5.42-5.40 (m, 1H), 4.41 (t, J=7.2 Hz, 1H), 3.65-3.50 (m, 3H), 3.16-2.77 (m, 4H).

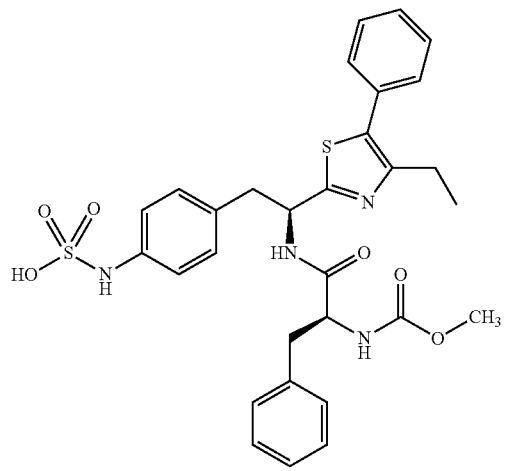 [SMILES: CCc1nc([C@H](Cc2ccc(NS(=O)(=O)O)cc2)NC(=O)[C@H](Cc2ccccc2)NC(=O)OC)sc1-c1ccccc1]

4-{(S)-2-(4-Ethyl-5-phenylthiazol-2-yl)-2-[(S)-2-(methoxycarbonylamino)-3-phenyl-propanamido]ethyl}phenylsulfamic acid: $^1$H NMR (300 MHz, CD$_3$OD): δ 7.50-7.38 (m, 4H), 7.21-7.11 (m, 10H), 5.45-5.35 (m, 1H), 5.42-4.37 (m, 1H), 3.63-3.50 (m, 3H), 3.34-3.29 (m, 3H), 3.15-3.03 (m, 2H), 2.84-2.74 (m, 3H), 1.31-1.21 (m, 3H).

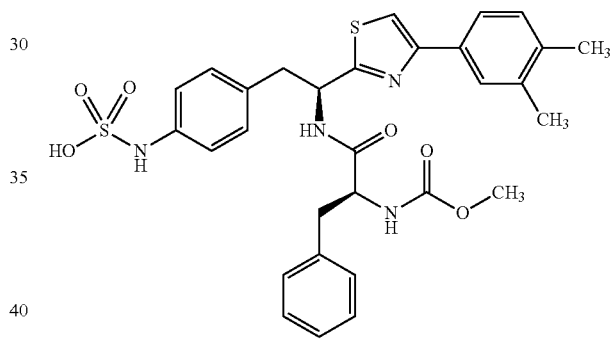

4-{(S)-2-[4-(3,4-dimethylphenyl)thiazol-2-yl]-2-[(S)-2-(methoxycarbonylamino)-3-phenylpropanamido]ethyl}phenylsulfamic acid: $^1$H NMR (300 MHz, CD$_3$OD): δ 8.60 (d, J=8.1 Hz, 1H), 7.73 (s, 1H), 7.65 (d, J=8.1 Hz, 1H), 7.57 (s, 1H), 7.21-7.11 (m, 10H), 5.47 (d, J=7.2 Hz, 1H), 4.44-4.38 (m, 1H), 3.63 (s, 2H), 3.62-3.51 (m, 1H), 3.40-3.32 (m, 1H), 3.20-3.05 (m, 2H), 2.84-2.77 (m, 1H), 2.35 (s, 3H), 2.32 (s, 3H).

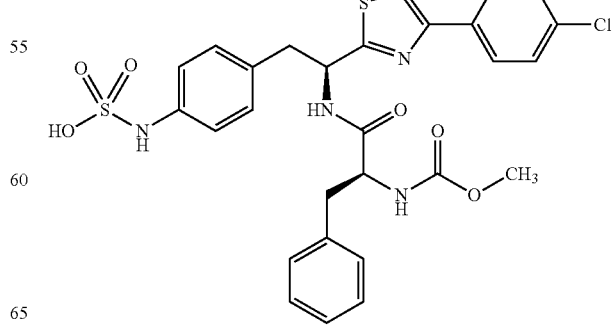

4-{(S)-2-[4-(4-Chlorophenyl)thiazol-2-yl]-2-[(S)-2-(methoxycarbonylamino)-3-phenylpropanamido]ethyl}phenylsulfamic acid: $^1$H NMR (300 MHz, CD$_3$OD): δ 8.65 (d, J=8.4 Hz, 1H), 7.95-7.91 (m, 2H), 7.70 (s, 1H), 7.46-7.41 (m, 2H), 7.19-7.10 (m, 9H), 5.50-5.45 (m, 1H), 4.41 (t, J=6.6 Hz, 1H), 3.63 (s, 2H), 3.62-3.51 (m, 1H), 3.41-3.33 (m, 1H), 3.20-3.04 (m, 2H), 2.81 (dd, J=13.8, 9.0 Hz, 1H).

4-{(S)-2-[(S)-2-(Methoxycarbonylamino)-3-phenylpropanamido]-2-[4-(thiophen-3-yl)thiazol-2-yl]ethyl}phenylsulfamic acid: $^1$H NMR (300 MHz, CD$_3$OD): δ 8.60 (d, J=7.8 Hz, 1H), 7.83 (d, J=1.5 Hz, 1H), 7.56-7.46 (m, 3H), 7.14 (d, J=25.2 Hz, 10H), 5.46-5.43 (m, 1H), 4.40-4.38 (m, 1H), 3.62 (s, 3H), 3.55-3.45 (m, 1H), 3.19-3.04 (m, 4H), 2.84-2.75 (m, 1H).

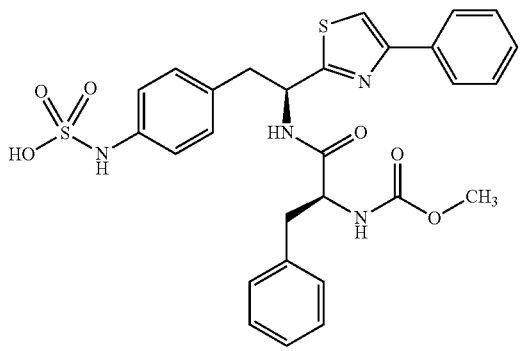 [SMILES: COC(=O)N[C@@H](Cc1ccccc1)C(=O)N[C@@H](Cc1ccc(NS(=O)(=O)O)cc1)c1nc(-c2ccccc2)cs1]

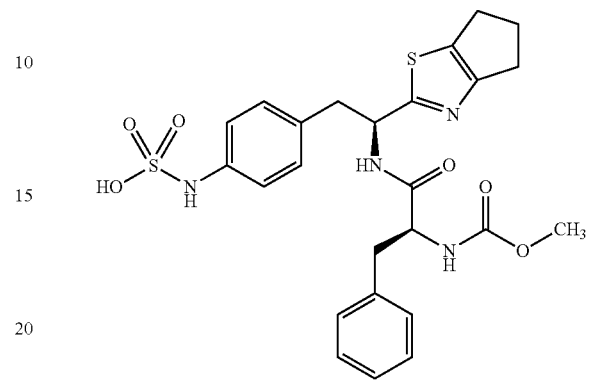

4-{(S)-2-[(S)-2-(Methoxycarbonylamino)-3-phenylpropanamido]-2-(4-phenylthiazol-2-yl)ethyl}phenylsulfamic acid: $^1$H(CD$_3$OD): δ 7.94-7.92 (d, 2H, J=7.3 Hz), 7.65 (s, 1H), 7.45-7.31 (m, 3H), 7.22-7.10 (m, 9H), 5.46 (t, 1H, J=6.8 Hz), 4.39 (m, 1H), 3.62 (s, 3H), 3.36-2.79 (m, 6H).

4-{(S)-2-(5,6-Dihydro-4H-cyclopenta[d]thiazol-2-yl)-2-[(S)-2-(methoxycarbonyl-amino)-3-phenylpropanamido]ethyl}phenylsulfamic acid: $^1$H NMR (300 MHz, CD$_3$OD): δ 8.46 (bs, 1H), 7.16-7.05 (m, 9H), 5.31 (bs, 1H), 4.35 (bs, 1H), 3.61 (s, 2H), 3.52-3.43 (m, 1H), 3.28-3.18 (m, 1H), 3.10-2.98 (m, 2H), 2.92-2.74 (m, 4H), 2.58-2.44 (m, 2H).

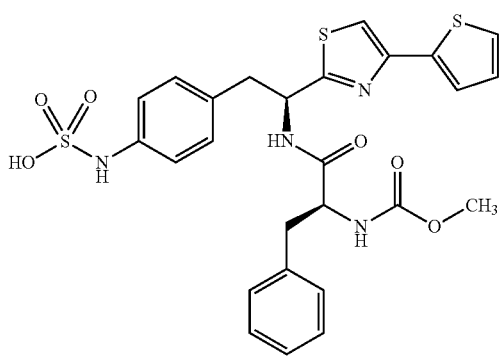 [SMILES: COC(=O)N[C@@H](Cc1ccccc1)C(=O)N[C@@H](Cc1ccc(NS(=O)(=O)O)cc1)c1nc(-c2cccs2)cs1]

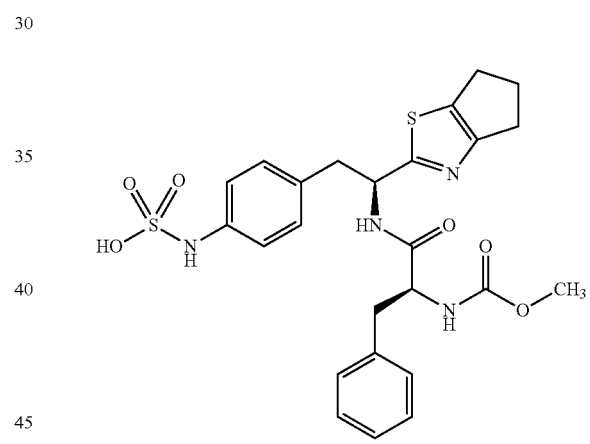

4-{(S)-2-[(S)-2-(Methoxycarbonylamino)-3-phenylpropanamido]-2-[4-(thiophen-2-yl)thiazol-2-yl]ethyl}phenylsulfamic acid: $^1$H NMR (300 MHz, CD$_3$OD): δ 8.63 (d, J=8.1 Hz, 1H), 7.52-7.51 (m, 2H), 7.39 (dd, J=5.1, 1.2 Hz, 1H), 7.20-7.08 (m, 10H), 5.50-5.40 (m, 1H), 4.39 (t, J=8.1 Hz, 1H), 3.63 (s, 2H), 3.50 (bs, 1H), 3.39-3.32 (m, 1H), 3.18-3.04 (m, 2H), 2.80 (dd, J=13.5, 8.7 Hz, 1H).

4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid: $^1$H NMR (300 MHz, CD$_3$OD): δ 7.21-7.08 (m, 9H), 5.45-5.25 (m, 1H), 4.45-4.30 (m, 1H), 3.63 (s, 2H), 3.64-3.34 (m, 1H), 3.33-3.20 (m, 1H), 3.09-3.02 (m, 2H), 2.75 (bs, 5H), 1.90 (bs, 4H).

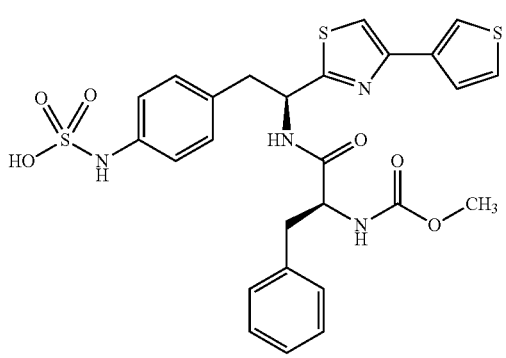 [SMILES: COC(=O)N[C@@H](Cc1ccccc1)C(=O)N[C@@H](Cc1ccc(NS(=O)(=O)O)cc1)c1nc(-c2ccsc2)cs1]

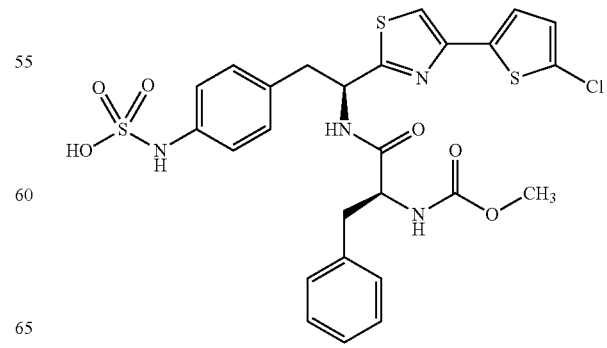

4-{(S)-2-[4-(5-Chlorothiophen-2-yl)thiazol-2-yl]-2-[(S)-2-(methoxycarbonyl-amino)-3-phenylpropanamido]ethyl}phenylsulfamic acid: $^1$H NMR (300 MHz, CD$_3$OD): δ 8.63 (d, J=8.7 Hz, 1H), 7.55 (s, 1H), 7.39-7.31 (m, 1H), 7.23-7.10 (m, 9H), 7.00-6.97 (m, 1H), 5.43-5.40 (m, 1H), 5.39 (t, J=14.7 Hz, 1H), 3.63 (s, 2H), 3.60-3.51 (m, 1H), 3.34-3.27 (m, 1H), 3.17-3.03 (m, 2H), 2.80 (dd, J=14.1, 8.4 Hz, 1H).

A further iteration of the first aspect of Category II relates to compounds wherein R$^2$ comprises —OCH$_2$CH$_3$ (ethoxy); the following is a non-limiting example thereof.

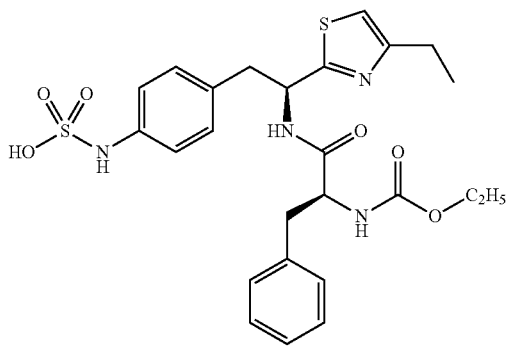 [SMILES: CCOC(=O)N[C@@H](Cc1ccccc1)C(=O)N[C@@H](Cc1ccc(NS(=O)(=O)O)cc1)c1nc(CC)cs1]

4-{(S)-2-[(S)-2-(Ethoxycarbonylamino)-3-phenylpropanamido]-2-(4-ethylthiazol-2-yl)ethyl}phenylsulfamic acid: $^1$H(CD$_3$OD): δ 7.22-7.00 (m, 10H), 5.39 (t, 1H, J=6.0 Hz), 4.37 (t, 1H, J=6.1 Hz), 4.08-4.00 (q, 2H, J=7.1 Hz), 3.25-2.74 (m, 6H), 1.30 (t, 3H, J=7.5 Hz), 1.20 (t, 3H, J=6.9 Hz).

The second aspect of Category II of the present disclosure relates to compounds having the formula:

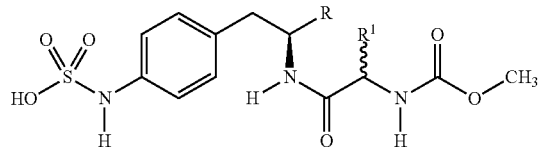

wherein R is a substituted or unsubstituted thiazol-4-yl unit and non-limiting examples of R and R$^1$ and the stereochemistry at R$^1$ are further described in Table IV.

TABLE IV

| No. | R | R$^1$ |
|---|---|---|
| 76 | thiazol-4-yl | (S)-benzyl |
| 77 | 2-methylthiazol-4-yl | (S)-benzyl |
| 78 | 2-ethylthiazol-4-yl | (S)-benzyl |
| 79 | 2-propylthiazol-4-yl | (S)-benzyl |
| 80 | 2-iso-propylthiazol-4-yl | (S)-benzyl |
| 81 | 2-cyclopropylthiazol-4-yl | (S)-benzyl |
| 82 | 2-butylthiazol-4-yl | (S)-benzyl |
| 83 | 2-tert-butylthiazol-4-yl | (S)-benzyl |
| 84 | 2-cyclohexylthiazol-4-yl | (S)-benzyl |
| 85 | 2-(2,2,2-trifluoroethyl)thiazol-4-yl | (S)-benzyl |
| 86 | 2-(3,3,3-trifluoropropyl)thiazol-4-yl | (S)-benzyl |
| 87 | 2-(2,2-difluorocyclopropyl)thiazol-4-yl | (S)-benzyl |
| 88 | 2-phenylthiazol-4-yl | (S)-benzyl |
| 89 | 2-(4-chlorophenyl)thiazol-4-yl | (S)-benzyl |
| 90 | 2-(3,4-dimethylphenyl)thiazol-4-yl | (S)-benzyl |
| 91 | 2-(thiophene-2-yl)thiazol-4-yl | (S)-benzyl |
| 92 | 2-(thiophene-3-yl)thiazol-4-yl | (S)-benzyl |

TABLE IV-continued

| No. | R | R$^1$ |
|---|---|---|
| 93 | 2-(3-chlorothiophene-2-yl)thiazol-4-yl | (S)-benzyl |
| 94 | 2-(3-methylthiophene-2-yl)thiazol-4-yl | (S)-benzyl |
| 95 | 2-(2-methylthiazol-4-yl)thiazol-4-yl | (S)-benzyl |
| 96 | 2-(furan-2-yl)thiazol-4-yl | (S)-benzyl |
| 97 | 2-(pyrazin-2-yl)thiazol-4-yl | (S)-benzyl |
| 98 | 2-[(2-methyl)pyridin-5-yl]thiazol-4-yl | (S)-benzyl |
| 99 | 2-(4-chlorobenzenesulfonylmethyl)thiazol-4-yl | (S)-benzyl |
| 100 | 2-(tert-butylsulfonylmethyl)thiazol-4-yl | (S)-benzyl |

The compounds encompassed within the second aspect of Category II of the present disclosure can be prepared by the procedure outlined in Scheme IV and described in Example 4 herein below.

Scheme IV

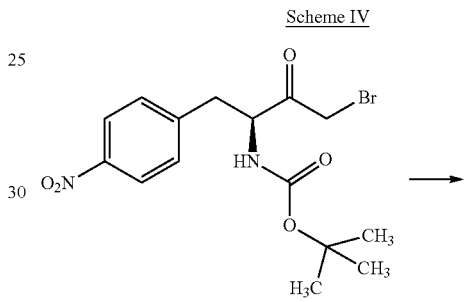

7

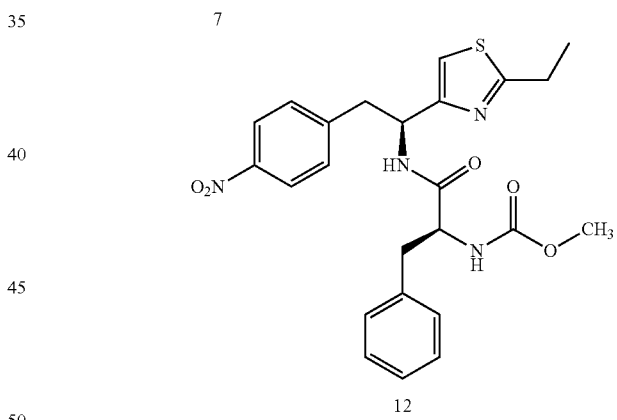

12

Reagents and conditions: (a)(i) propanethioamide, CH$_3$CN; reflux, 2 hr. (ii) Boc-Phe, HOBt, DIPEA, DMF; rt, 18 hr.

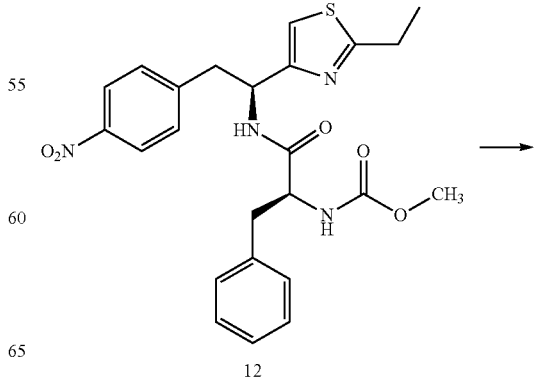

12

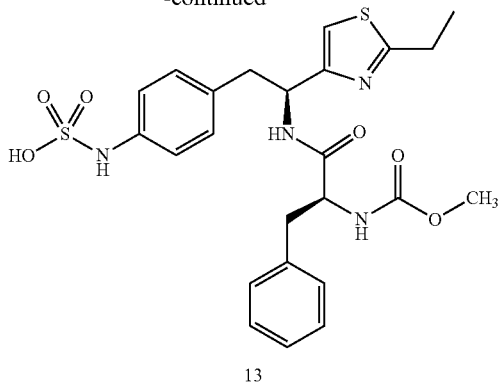

13

Reagents and conditions: (b) (i) H₂:Pd/C, MeOH; (ii) SO₃-pyridine, NH₄OH; rt, 18 hr.

Example 4

4-{(S)-2-[(S)-2-(Methoxycarbonylamino)-3-phenyl-propanamido]-2-(2-ethylthiazol-4-yl)ethyl}phenylsulfamic acid (13)

Preparation of methyl (S)-1-[(S)-1-(2-ethylthiazole-4-yl)-2-(4-nitrophenyl)-ethyl]amino-1-oxo-3-phenylpropane-2-ylcarbamate (12): A mixture of propanethioamide (69 mg, 0.78 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed for 2 hours. The reaction mixture is cooled to room temperature and diethyl ether is added to precipitate the intermediate 2-(nitrophenyl)-(S)-1-(4-ethylthiazol-2-yl)ethylamine which is isolated by filtration as the hydrobromide salt. The hydrobromide salt is dissolved in DMF (8 mL) together with diisoproylethylamine (0.38 mL, 2.13 mmol), 1-hydroxybenzotriazole (107 mg, 0.71 mmol) and (S)-(2-methoxycarbonyl-amino)-3-phenylpropionic acid (175 mg, 0.78 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.300 g (81% yield) of the desired product which is used without further purification. LC/MS ESI+MS 483 (M+1).

Preparation of 4-((S)-2-((S)-2-(methoxycarbonylamino)-3-phenylpropanamido)-2-(2-ethylthiazol-4-yl)ethyl)phenylsulfamic acid ammonium salt (13): tert-Butyl (S)-1-(S)-2-(4-nitrophenyl)-1-(2-ethylthiazole-4-yl)ethylamino-1-oxo-3-phenylpropan-2-ylcarbamate, 12, (0.300 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (223 mg, 1.40 mmol). The reaction is stirred at room temperature for 5 minutes after which a 7% solution of NH₄OH (12 mL) is added. The mixture is then concentrated and the resulting residue is purified by reverse phase chromatography to afford 25 mg of the desired product as the ammonium salt. ¹H NMR (300 MHz, MeOH-d₄) δ 7.14-7.24 (m, 6H), 6.97-7.0 (m, 4H), 6.62 (s, 1H), 5.10-5.30 (m, 1H), 4.36 (t, J=7.2 Hz, 1H), 3.63 (s, 3H), 3.14 (dd, J=13.5 and 6.3 Hz, 1H), 2.93-3.07 (m, 5H), 2.81 (dd, J=13.5 and 6.3 Hz, 1H), 1.39 (t, J=7.8 Hz, 3H).

In another iteration of the process of the present disclosure, compound 13, as well as the other analogs which comprise the present disclosure, can be isolated as the free acid by adapting the procedure described herein below.

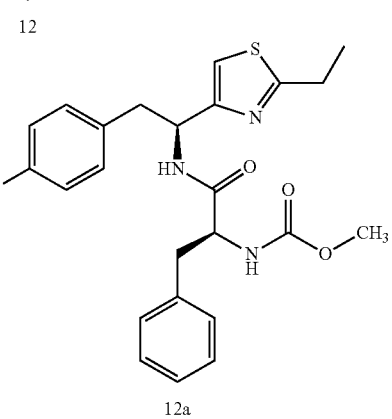

12

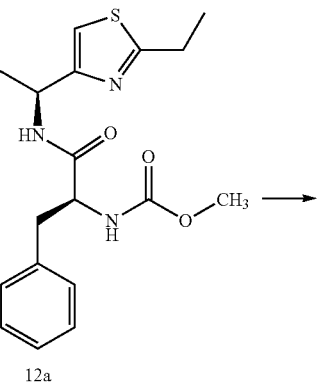

12a

Reagents and conditions: (a) H₂:Pd/C, MeOH; rt, 40 hr.

12a

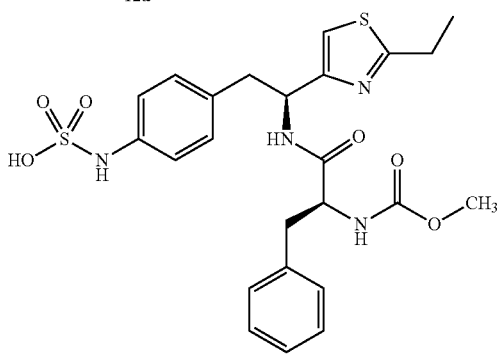

13

Reagents and conditions: (b) SO₃-pyridine, CH₃CN; heat, 45 min.

Example 4a

4-((S)-2-((S)-2-(Methoxycarbonylamino)-3-phenyl-propanamido)-2-(2-ethylthiazol-4-yl)ethyl)phenyl-sulfamic acid [Free Acid Form](13)

Preparation of {1-[2-(S)-(4-(S)-aminophenyl)-1-(2-ethylthiazol-4-yl)ethyl-carbamoyl]-2-phenylethyl}-carbamic acid methyl ester (12a): A Parr hydrogenation vessel is charged with tert-butyl (S)-1-(S)-2-(4-nitrophenyl)-1-(2-ethylthiazole-4-yl)ethylamino-1-oxo-3-phenylpropan-2-ylcarbamate, 12, (18.05 g, 37.4 mmol, 1.0 eq) and Pd/C (10% Pd on C, 50% wet, Degussa-type E101 NE/W, 2.68 g, 15 wt %) as solids. MeOH (270 mL, 15 mL/g) is added to provide a suspension. The vessel is put on a Parr hydrogenation apparatus. The vessel is submitted to a fill/vacuum evacuate process with $N_2$ (3×20 psi) to inert, followed by the same procedure with $H_2$ (3×40 psi). The vessel is filled with $H_2$ and the vessel is shaken under 40 psi $H_2$ for ~40 hr. The vessel is evacuated and the atmosphere is purged with $N_2$ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford 16.06 g (95% yield) of the desired product as a tan solid, which is used without further purification.

Preparation of 4-((S)-2-((S)-2-(methoxycarbonylamino)-3-phenylpropanamido)-2-(2-ethylthiazol-4-yl)ethyl)phenyl-sulfamic acid (13): A 100 mL RBF is charged with {1-[2-(S)-(4-(S)-aminophenyl)-1-(2-ethylthiazol-4-yl)ethyl-carbamoyl]-2-phenylethyl}-carbamic acid methyl ester, 12a, (10.36 g, 22.9 mmol, 1.0 eq) prepared in the step described herein above. Acetonitrile (50 mL, 5 mL/g) is added and the yellow suspension is stirred at room temperature. A second 3-necked 500 mL RBF is charged with $SO_3$.pyr (5.13 g, 32.2 mmol, 1.4 eq) and acetonitrile (50 mL 5 mL/g) and the white suspension is stirred at room temperature. Both suspensions are gently heated until the reaction solution containing {1-[2-(S)-(4-(S)-aminophenyl)-1-(2-ethylthiazol-4-yl)ethyl-carbamoyl]-2-phenylethyl}-carbamic acid methyl ester becomes red-orange in color (typically for this example about 44° C.). This substrate containing solution is poured in one portion into the stirring suspension of $SO_3$.pyr at 35° C. The resulting opaque mixture (39° C.) is stirred vigorously while allowed to slowly cool to room temperature. After stirring for 45 min, the reaction is determined to be complete by HPLC. $H_2O$ (200 mL, 20 mL/g) is added to the orange suspension to provide a yellow-orange homogeneous solution having a pH of approximately 2.4. Concentrated $H_3PO_4$ is added slowly over 12 minutes to lower the pH to approximately 1.4. During this pH adjustment, an off-white precipitate is formed and the solution is stirred at room temperature for 1 hr. The suspension is filtered and the filter cake is washed with the filtrate. The filter cake is air-dried on the filter overnight to afford 10.89 g (89% yield) of the desired product as a tan solid.

The following are further non-limiting examples of the second aspect of Category II of the present disclosure.

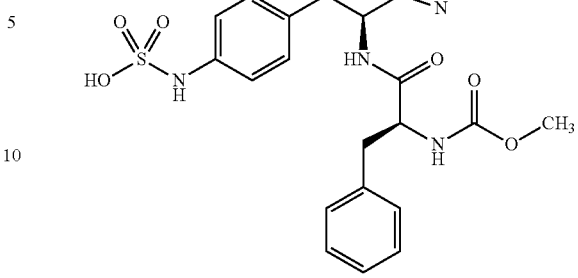

4-{(S)-2-[(S)-2-(Methoxycarbonylamino)-3-phenylpropanamido]-2-(2-methylthiazol-4-yl)ethyl}phenylsulfamic acid: $^1$H NMR (300 MHz, MeOH-d$_4$) δ 8.15 (d, J=8.4 Hz, 1H), 7.16-7.25 (m, 5H), 6.97-7.10 (m, 4H), 6.61 (s, 1H), 5.00-5.24 (m, 1H), 4.36 (t, J=7.2 Hz, 1H), 3.64 (s, 2H), 3.11-3.19 (s, 1H), 2.92-3.04 (s, 2H), 2.81 (dd, J=13.5 and 8.1 Hz, 1H), 2.75 (s, 3H).

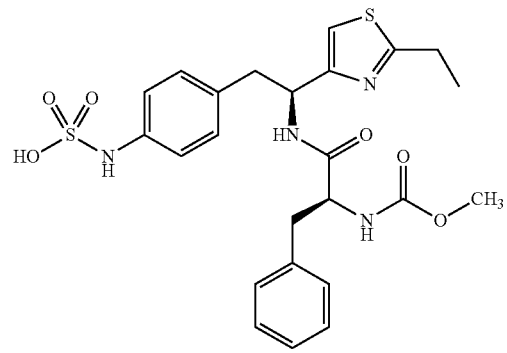 [SMILES: CCc1nc([C@H](Cc2ccc(NS(=O)(=O)O)cc2)NC(=O)[C@H](Cc2ccccc2)NC(=O)OC)cs1]

4-{(S)-2-(2-Ethylthiazole-4-yl)-2-[(S)-2-(methoxycarbonylamino)-3-phenylpropan-amido]ethyl}phenylsulfamic acid: $^1$HNMR (300 MHz, MeOH-d$_4$) δ 7.16-7.29 (m, 5H), 7.02-7.12 (m, 4H), 6.83 (s, 1H), 5.10-5.35 (m, 1H), 3.52-3.67 (m, 3H), 3.18-3.25 (m, 2H), 3.05 (q, J=7.5 Hz, 2H), 2.82-2.95 (m, 2H), 2.65 (s, 3H), 1.39 (t, J=7.5 Hz, 3H).

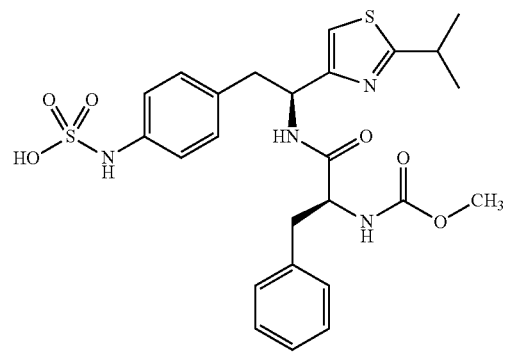 [SMILES: COC(=O)N[C@@H](Cc1ccccc1)C(=O)N[C@@H](Cc1ccc(NS(=O)(=O)O)cc1)c1csc(C(C)C)n1]

4-{(S)-2-(2-Isopropylthiazol-4-yl)-2-[(S)-2-(methoxycarbonylamino)-3-phenylpropan-amido]ethyl}phenylsulfamic acid: $^1$H NMR (CD$_3$OD) δ 8.16 (d, 1H, J=8.7 Hz), 7.22-7.13 (m, 3H), 7.07 (d, 1H, J=8.4 Hz), 6.96 (d, 1H, J=8.1 Hz), 6.62 (s, 1H), 5.19 (t, 1H, J=7.2 Hz), 4.36 (t, 1H, J=7.8 Hz), 3.63 (s, 3H), 3.08 (1H, A of ABX, J=3.6, 14.5 Hz), 2.99 (1H, B of ABX, J=7.2, 13.8 Hz), 2.85-2.78 (m, 1H), 1.41 (d, 6H, J=6.9 Hz).

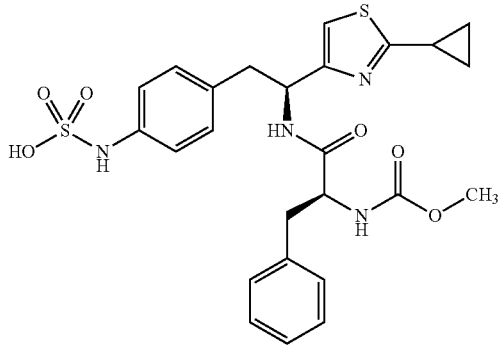 [SMILES: COC(=O)N[C@@H](Cc1ccccc1)C(=O)N[C@@H](Cc1ccc(NS(=O)(=O)O)cc1)c1csc(C2CC2)n1]

4-{(S)-2-(2-Cyclopropylthiazol-4-yl)-2-[(S)-2-(methoxycarbonylamino)-3-phenylpropanamido]ethyl}phenylsulfamic acid: $^{1}$H(CD$_{3}$OD): δ 7.15-7.02 (m, 5H), 6.96-6.93 (d, 2H, J=8.4 Hz), 6.86-6.83 (d, 2H, J=8.3 Hz), 6.39 (s, 1H), 5.01 (t, 1H, J=5.0 Hz), 4.22 (t, 1H, J=7.4 Hz), 3.51 (s, 3H), 2.98-2.69 (m, 2H), 2.22-2.21 (m, 1H), 1.06-1.02 (m, 2H), 0.92-0.88 (m, 2H).

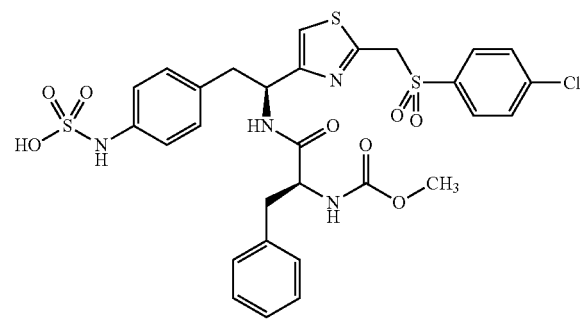 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1]

4-{(S)-2-{2-[(4-Chlorophenylsulfonyl)methyl]thiazol-4-yl}-2-[(S)-2-(methoxycarbonyl-amino)-3-phenylpropanamido]ethyl}phenylsulfamic acid: $^{1}$H(CD$_{3}$OD): δ 7.96-7.93 (d, 2H, J=8.6 Hz), 7.83-7.80 (d, 2H, J=8.6 Hz), 7.44-7.34 (m, 5H), 7.29-7.27 (d, 2H, J=8.4 Hz), 7.14-7.11 (d, 2H, J=8.4 Hz), 6.97 (s, 1H), 5.31 (t, 1H, J=6.8 Hz), 5.22-5.15 (m, 2H), 4.55 (t, 1H, J=7.3 Hz), 3.84 (s, 3H), 3.20-2.96 (m, 4H).

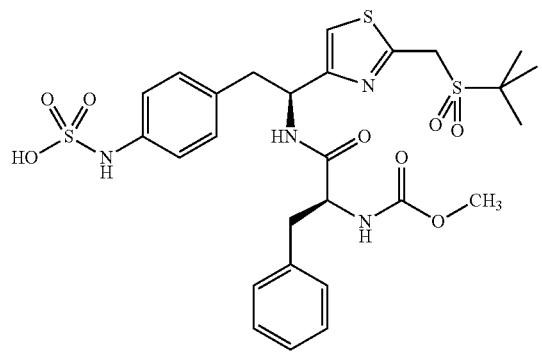 [SMILES: COC(=O)N[C@@H](Cc1ccccc1)C(=O)N[C@@H](Cc1ccc(NS(=O)(=O)O)cc1)c1csc(CS(=O)(=O)C(C)(C)C)n1]

4-{(S)-2-[2-(tert-Butylsulfonylmethyl)thiazol-4-yl]-2-[(S)-2-(methoxycarbonyl-amino)-3-phenylpropanamido]

ethyl}phenylsulfamic acid: $^{1}$H(CD$_{3}$OD): δ 7.40-7.30 (m, 5H), 7.21-7.10 (m, 4H), 7.02 (s, 1H), 5.37 (t, 1H, J=6.9 Hz), 5.01-4.98 (m, 2H), 4.51 (t, 1H, J=7.1 Hz), 3.77 (s, 3H), 3.34-2.91 (m, 4H), 1.58 (s, 9H).

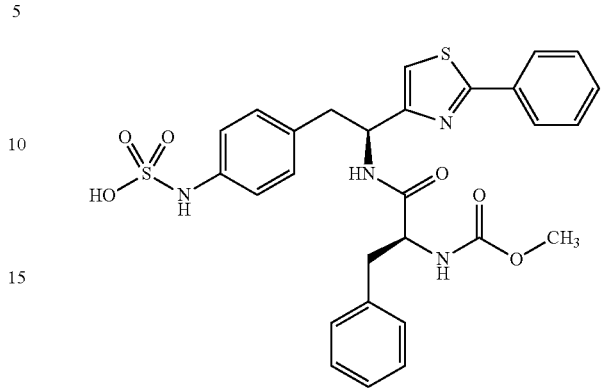

4-{(S)-2-[(S)-2-(Methoxycarbonylamino)-3-phenylpropionamido]-2-(2-phenylthiazole-4-yl)ethyl}phenylsulfamic acid: $^{1}$H NMR (300 MHz, DMSO-d$_{6}$) δ 7.96-7.99 (m, 2H), 7.51-7.56 (m, 3H), 7.13-7.38 (m, 6H), 6.92-6.95 (m, 4H), 5.11-5.16 (m, 1H), 4.32-4.35 (m, 1H), 3.51 (s, 3H), 3.39-3.40 (m, 2H), 3.09-3.19 (m, 1H), 2.92-3.02 (m, 2H), 2.75 (dd, J=10.5 Hz and 9.9 Hz, 1H).

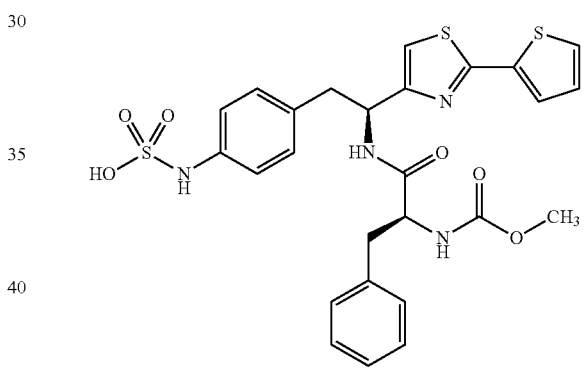

4-{(S)-2-[(S)-2-(Methoxycarbonylamino)-3-phenylpropanamido]-2-[2-(thiophen-2-yl)thiazol-4-yl]ethyl}phenylsulfamic acid: $^{1}$H(CD$_{3}$OD): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

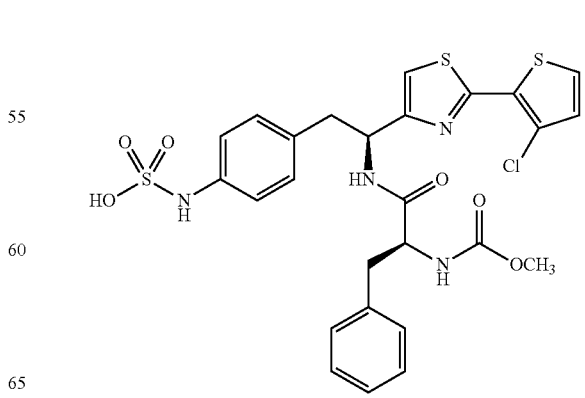

4-{(S)-2-[2-(3-Chlorothiophen-2-yl)thiazol-4-yl]-2-[(S)-2-(methoxycarbonyl-amino)-3-phenylpropanamido]ethyl}phenylsulfamic acid: $^1$H(CD$_3$OD): δ 7.78-7.76 (d, 1H, J=5.4 Hz), 7.36-7.14 (m, 10H), 7.03 (s, 1H), 5.39 (t, 1H, J=6.9 Hz), 4.54 (t, 1H, J=7.3 Hz), 3.80 (s, 3H), 3.39-2.98 (m, 4H).

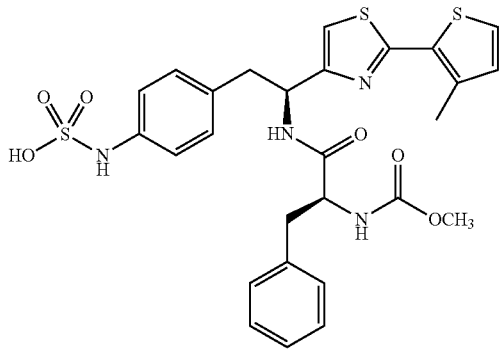 [SMILES: COC(=O)N[C@@H](Cc1ccccc1)C(=O)N[C@@H](Cc1ccc(NS(=O)(=O)O)cc1)c1csc(-c2sccc2C)n1]

4-{(S)-2-[(S)-2-(Methoxycarbonylamino)-3-phenylpropanamido]-2-[2-(3-methylthiophen-2-yl)thiazol-4-yl]ethyl}phenylsulfamic acid: $^1$H(CD$_3$OD): δ 7.38 (d, 1H, J=5.1 Hz), 7.15-6.93 (m, 10H), 6.73 (s, 1H), 5.17 (t, 1H, J=6.9 Hz), 4.31 (t, 1H, J=7.3 Hz), 3.57 (s, 3H), 3.18-3.11 (m, 1H), 3.02-2.94 (m, 2H), 2.80-2.73 (m, 1H) 2.46 (s, 3H).

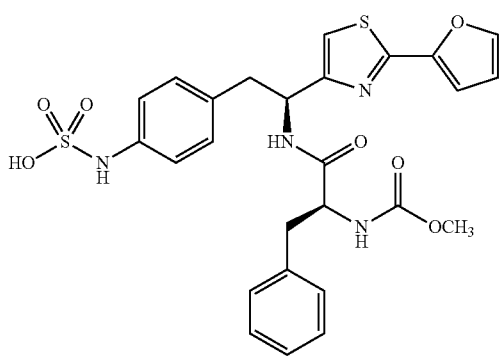 [SMILES: COC(=O)N[C@@H](Cc1ccccc1)C(=O)N[C@@H](Cc1ccc(NS(=O)(=O)O)cc1)c1csc(-c2ccco2)n1]

4-{[(S)-2-(2-(Furan-2-yl)thiazol-4-yl]-2-[(S)-2-(methoxycarbonylamino)-3-phenylpropanamido]ethyl}phenylsulfamic acid: $^1$H(CD$_3$OD): δ 7.54-7.46 (m, 1H), 7.02-6.79 (m, 10H), 6.55-6.51 (m, 1H), 6.44-6.41 (m, 1H), 5.02-5.00 (q, 1H, J=6.4 Hz), 4.16-4.14 (q, 1H, J=7.1 Hz), 3.43 (s, 3H) 2.96-2.58 (m, 4H).

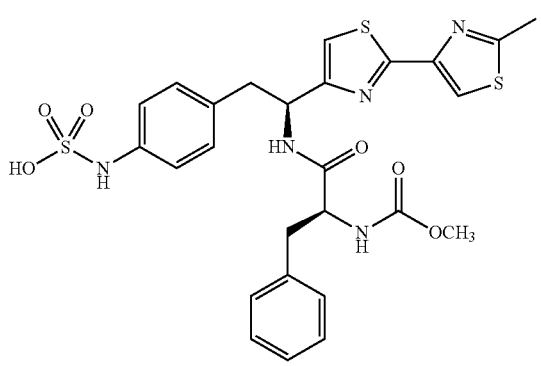 [SMILES: COC(=O)N[C@@H](Cc1ccccc1)C(=O)N[C@@H](Cc1ccc(NS(=O)(=O)O)cc1)c1csc(-c2csc(C)n2)n1]

4-{(S)-2-[(S)-2-(Methoxycarbonylamino)-3-phenylpropanamido]2-[2-(2-methylthiazole-4-yl)thiazole-4yl]ethyl}phenylsulfamic acid: $^1$H NMR (300 MHz, MeOH-d$_4$) δ 8.27 (d, J=5.4 Hz, 1H), 7.97 (s, 1H), 6.99-7.21 (m, 8H), 5.18-5.30 (m, 1H), 4.30-4.39 (m, 1H), 3.64 (s, 3H), 3.20 (dd, J=14.1 and 6.6 Hz, 1H), 2.98-3.08 (m, 2H), 2.84 (dd, J=14.1 and 6.6 Hz, 1H), 2.78 (s, 3H).

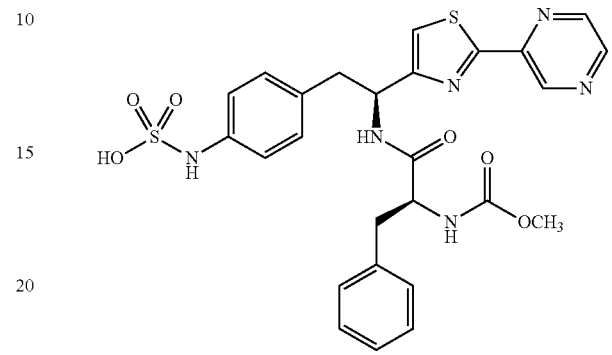

4-{(S)-2-[(S)-2-(Methoxycarbonylamino)-3-phenylpropanamido]-2-(2-pyrazine-2-yl)thiazole-4-yl}phenylsulfamic acid: $^1$H NMR (300 MHz, MeOH-d$_4$) δ 9.34 (s, 1H), 8.65 (s, 2H), 8.34 (d, J=8.1 Hz, 1H), 7.00-5.16 (m, 9H), 5.30 (q, J=7.2 Hz, 1H), 4.41 (t, J=7.2 Hz, 1H), 3.65 (s, 3H), 3.23 (dd, J=13.8 and 6.9 Hz, 1H), 2.98-3.13 (m, 2H), 2.85 (dd, J=13.8 and 6.9 Hz, 1H).

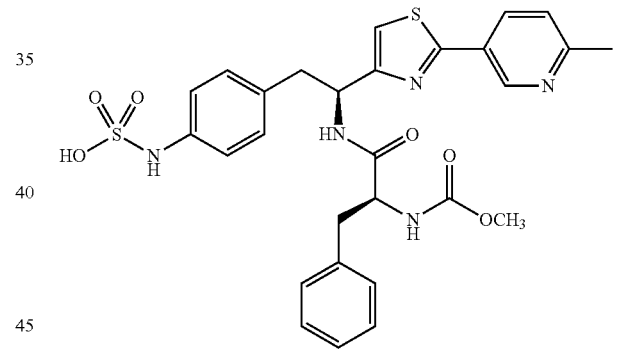

4-{(S)-2-[(S)-2-(Methoxycarbonylamino)-3-phenylpropanamido]-2-[2-(6-methylpyridin-3-yl)thiazol-4-yl]ethyl}phenylsulfamic acid: $^1$H(CD$_3$OD): δ 8.90 (s, 1H), 8.19-8.13 (m, 1H), 7.39-7.36 (d, 1H, J=8.2 Hz), 7.07-6.88 (m, 9H), 6.79 (s, 1H), 5.17 (t, 1H, J=7.0 Hz), 4.29 (t, 1H, J=7.4 Hz), 3.54 (s, 3H), 3.10-2.73 (m, 4H), 2.53 (s, 3H).

Category III of the present disclosure relates to compounds having the formula:

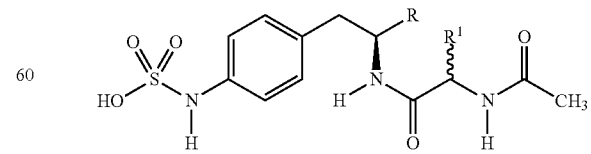

wherein R is a substituted or unsubstituted thiazol-2-yl unit and non-limiting examples of R and R$^1$ and the stereochemistry at R$^1$ are further described in Table V.

TABLE V

| No. | R | R¹ |
|---|---|---|
| 101 | thiazol-2-yl | (S)-benzyl |
| 102 | 4-methylthiazol-2-yl | (S)-benzyl |
| 103 | 4-ethylthiazol-2-yl | (S)-benzyl |
| 104 | 4-propylthiazol-2-yl | (S)-benzyl |
| 105 | 4-iso-propylthiazol-2-yl | (S)-benzyl |
| 106 | 4-cyclopropylthiazol-2-yl | (S)-benzyl |
| 107 | 4-butylthiazol-2-yl | (S)-benzyl |
| 108 | 4-tert-butylthiazol-2-yl | (S)-benzyl |
| 109 | 4-cyclohexylthiazol-2-yl | (S)-benzyl |
| 110 | 4-(2,2,2-trifluoroethyl)thiazol-2-yl | (S)-benzyl |
| 111 | 4-(3,3,3-trifluoropropyl)thiazol-2-yl | (S)-benzyl |
| 112 | 4-(2,2-difluorocyclopropyl)thiazol-2-yl | (S)-benzyl |
| 113 | 4-(methoxymethyl)thiazol-2-yl | (S)-benzyl |
| 114 | 4-(carboxylic acid ethyl ester)thiazol-2-yl | (S)-benzyl |
| 115 | 4,5-dimethylthiazol-2-yl | (S)-benzyl |
| 116 | 4-methyl-5-ethylthiazol-2-yl | (S)-benzyl |
| 117 | 4-phenylthiazol-2-yl | (S)-benzyl |
| 118 | 4-(4-chlorophenyl)thiazol-2-yl | (S)-benzyl |
| 119 | 4-(3,4-dimethylphenyl)thiazol-2-yl | (S)-benzyl |
| 120 | 4-methyl-5-phenylthiazol-2-yl | (S)-benzyl |
| 121 | 4-(thiophene-2-yl)thiazol-2-yl | (S)-benzyl |
| 122 | 4-(thiophene-3-yl)thiazol-2-yl | (S)-benzyl |
| 123 | 4-(5-chlorothiophene-2-yl)thiazol-2-yl | (S)-benzyl |
| 124 | 5,6-dihydro-4H-cyclopenta[d]thiazol-2-yl | (S)-benzyl |
| 125 | 4,5,6,7-tetrahydrobenzo[d]thiazol-2-yl | (S)-benzyl |

The compounds encompassed within Category III of the present disclosure can be prepared by the procedure outlined in Scheme V and described in Example 5 herein below.

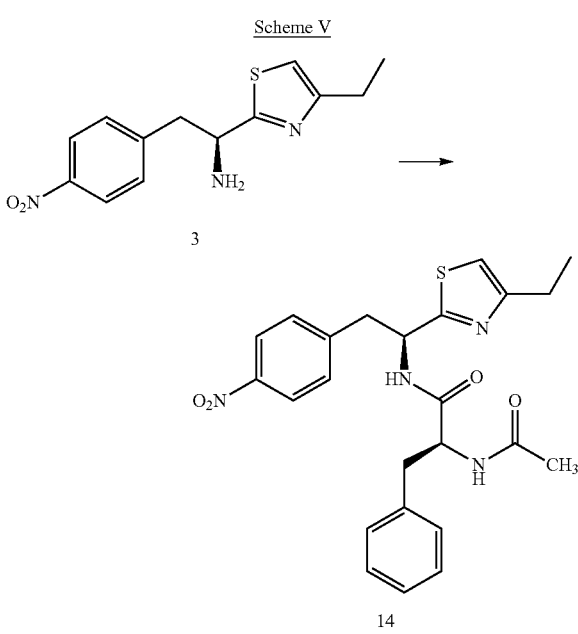

Scheme V

Reagents and conditions: (a) Ac-Phe, EDCI, HOBt, DIPEA, DMF; rt, 18 hr.

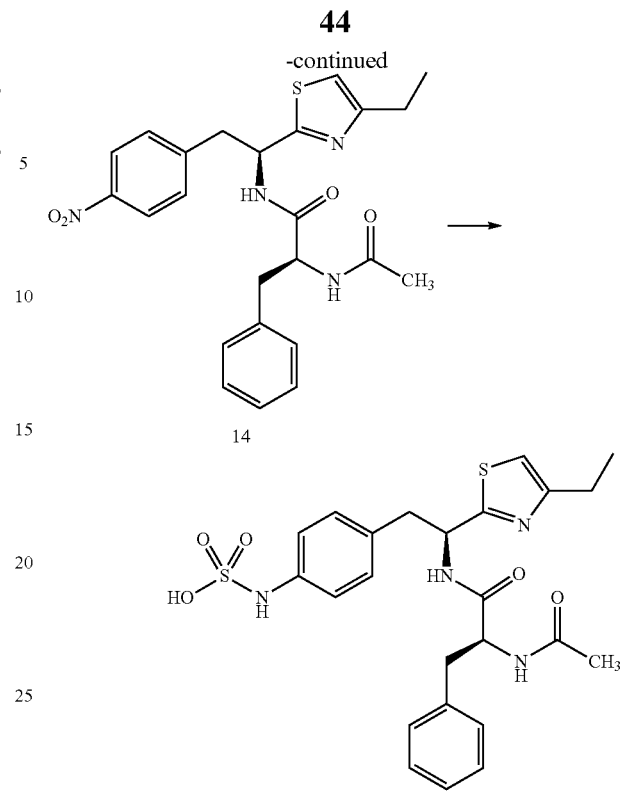

Reagents and conditions: (b) (i) H₂:Pd/C, MeOH; (ii) SO₃-pyridine, NH₄OH.

Example 5

4-[(S)-2-((S)-2-Acetamido-3-phenylpropanamido)-2-(4-ethylthiazol-2-yl)ethyl]phenylsulfamic acid (15)

Preparation of (S)-2-acetamido-N—[(S)-1-(4-ethylthiazol-2-yl)-2-(4-nitrophenyl)ethyl]-3-phenylpropanamide (14): To a solution of 1-(S)-(4-ethylthiazol-2-yl)-2-(4-nitrophenyl)ethyl amine hydrobromide, 3, (0.343 g, 0.957 mmol), N-acetyl-L-phenylalanine (0.218 g), 1-hydroxybenzotriazole (HOBt) (0.161 g), diisopropyl-ethylamine (0.26 g), in DMF (10 mL) at 0°, is added 1-(3-dimethylaminopropyl)-3-ethylcarbodiimide (EDCI) (0.201 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.313 g (70% yield) of the desired product which is used without further purification. LC/MS ESI+467 (M+1).

Preparation of 4-((S)-2-((S)-2-acetamido-3-phenylpropanamido)-2-(4-ethylthiazol-2-yl)ethyl)phenylsulfamic acid (15): (S)-2-Acetamido-N—[(S)-1-(4-ethylthiazol-2-yl)-2-(4-nitrophenyl)ethyl]-3-phenylpropanamide, 14, (0.313 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.320 g). The reaction is stirred at room temperature for 5 minutes after which a 7% solution of NH₄OH (30 mL) is added. The mixture is then concentrated and the resulting residue is purified by reverse phase chromatography to afford 0.215 g of the desired product as the ammonium salt. $^1$H(CD$_3$OD): δ 7.23-6.98 (m, 10H), 5.37 (t, 1H), 4.64 (t, 1H, J=6.3 Hz), 3.26-2.74 (m, 6H), 1.91 (s, 3H), 1.29 (t, 3H, J=7.5 Hz).

The following are further non-limiting examples of compounds encompassed within Category III of the present disclosure.

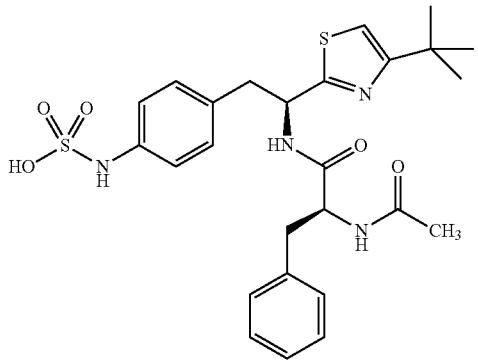 [SMILES: CC(=O)N[C@@H](Cc1ccccc1)C(=O)N[C@@H](Cc1ccc(NS(=O)(=O)O)cc1)c1nc(C(C)(C)C)cs1]

4-[(S)-2-((S)-2-Acetamido-3-phenylpropanamido)-2-(4-tert-butylthiazol-2-yl)ethyl]phenylsulfamic acid: $^1$H NMR (300 MHz, CD$_3$OD): δ 7.22-7.17 (m, 5H), 7.06 (dd, J=14.1, 8.4 Hz, 4H), 6.97 (d, J=0.9 Hz, 1H), 5.39 (dd, J=8.4, 6.0 Hz, 1H), 4.65 (t, J=7.2 Hz, 1H), 3.33-3.26 (m, 1H), 3.13-3.00 (m, 3H), 2.80 (dd, J=13.5, 8.7 Hz, 1H), 1.91 (s, 3H), 1.36 (s, 9H).

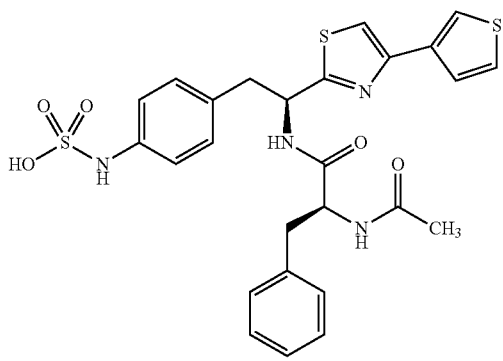 [SMILES: CC(=O)N[C@@H](Cc1ccccc1)C(=O)N[C@@H](Cc1ccc(NS(=O)(=O)O)cc1)c1nc(-c2ccsc2)cs1]

4-{(S)-2-((S)-2-Acetamido-3-phenylpropanamido)-2-[4-(thiophen-3-yl)thiazol-2-yl]ethyl}phenylsulfamic acid: $^1$H NMR (300 MHz, CD$_3$OD): δ 8.58 (d, J=8.1 Hz, 1H), 7.83-7.82 (m, 1H), 7.57-7.46 (m, 3H), 7.28-6.93 (m, 11H), 5.54-5.43 (m, 1H), 4.69-4.55 (m, 2H), 3.41-3.33 (m, 1H), 3.14-3.06 (3H), 2.86-2.79 (m, 1H), 1.93 (s, 3H).

The first aspect of Category IV of the present disclosure relates to compounds having the formula

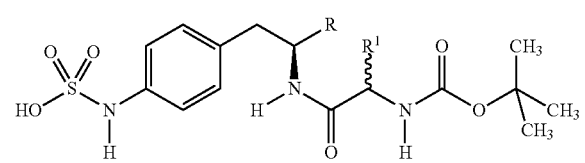

wherein R is a substituted or unsubstituted thiophene-2-yl unit and non-limiting examples of R and R$^1$ and the stereochemistry at R$^1$ are further described in Table VI.

TABLE VI

| No. | R | R$^1$ |
|---|---|---|
| 126 | thiazol-2-yl | hydrogen |
| 127 | 4-methylthiazol-2-yl | hydrogen |
| 128 | 4-ethylthiazol-2-yl | hydrogen |
| 129 | 4-propylthiazol-2-yl | hydrogen |
| 130 | 4-iso-propylthiazol-2-yl | hydrogen |
| 131 | 4-cyclopropylthiazol-2-yl | hydrogen |
| 132 | 4-butylthiazol-2-yl | hydrogen |
| 133 | 4-tert-butylthiazol-2-yl | hydrogen |
| 134 | 4-cyclohexylthiazol-2-yl | hydrogen |
| 135 | 4,5-dimethylthiazol-2-yl | hydrogen |
| 136 | 4-methyl-5-ethylthiazol-2-yl | hydrogen |
| 137 | 4-phenylthiazol-2-yl | hydrogen |
| 138 | thiazol-2-yl | (S)-iso-propyl |
| 139 | 4-methylthiazol-2-yl | (S)-iso-propyl |
| 140 | 4-ethylthiazol-2-yl | (S)-iso-propyl |
| 141 | 4-propylthiazol-2-yl | (S)-iso-propyl |
| 142 | 4-iso-propylthiazol-2-yl | (S)-iso-propyl |
| 143 | 4-cyclopropylthiazol-2-yl | (S)-iso-propyl |
| 144 | 4-butylthiazol-2-yl | (S)-iso-propyl |
| 145 | 4-tert-butylthiazol-2-yl | (S)-iso-propyl |
| 146 | 4-cyclohexylthiazol-2-yl | (S)-iso-propyl |
| 147 | 4,5-dimethylthiazol-2-yl | (S)-iso-propyl |
| 148 | 4-methyl-5-ethylthiazol-2-yl | (S)-iso-propyl |
| 149 | 4-phenylthiazol-2-yl | (S)-iso-propyl |
| 150 | 4-(thiophene-2-yl)thiazol-2-yl | (S)-iso-propyl |

The compounds encompassed within Category IV of the present disclosure can be prepared by the procedure outlined in Scheme VI and described in Example 6 herein below.

Scheme VI

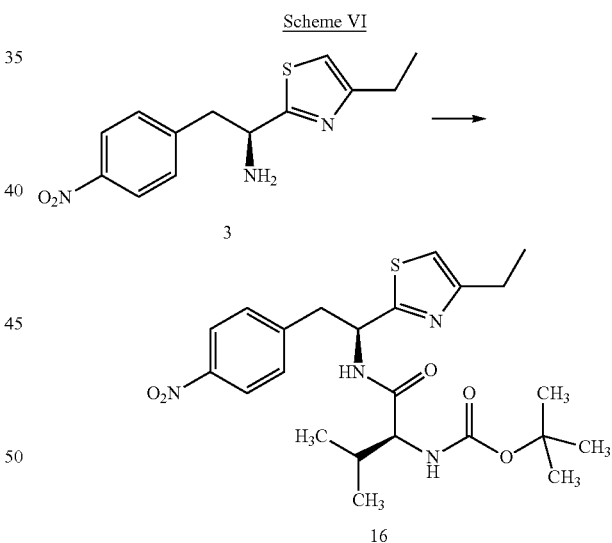

Reagents and conditions: (a) Boc-Val; EDCI, HOBt, DIPEA, DMF; rt, 18 hr.

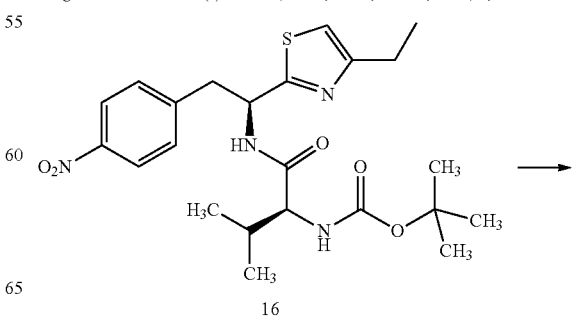

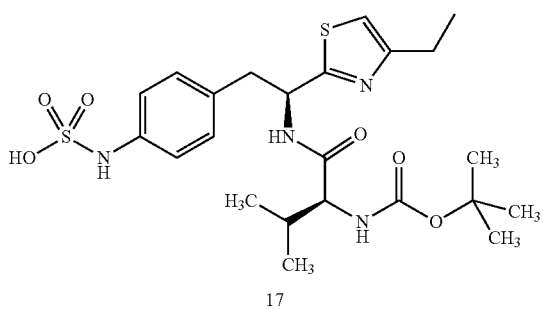

17

Reagents and conditions: (b) (i) H₂:Pd/C, MeOH; (ii) SO₃-pyridine, NH₄OH, rt, 2 hr. . .

Example 6

4-{(S)-2-[(S)-2-(tert-Butoxycarbonylamino)-3-methylbutanamido]-2-(4-ethylthiazol-2-yl)ethyl}phenylsulfamic acid (17)

Preparation of {1-[1-(ethylthiazol-2-yl)-2-(4-nitrophenyl)ethylcarbamoyl]-2-methylpropyl}carbamic acid tert-butylester (16): To a solution of 1-(S)-(4-ethylthiazol-2-yl)-2-(4-nitrophenyl)ethyl amine hydrobromide, 3, (0.200 g, 0.558 mmol), (S)-(2-tert-butoxycarbonylamino)-3-methylbutyric acid (0.133 g) and 1-hydroxybenzotriazole (HOBt) (0.094 g) in DMF (5 mL) at 0°, is added 1-(3-dimethylaminopropyl)-3-ethylcarbodiimide (EDCI) (0.118 g) followed by diisopropylamine (0.151 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.219 g (82% yield) of the desired product which is used without further purification. LC/MS ESI+477 (M+1).

Preparation of 4-{(S)-2-[(S)-2-(tert-butoxycarbonylamino)-3-methylbutanamido]-2-(4-ethylthiazol-2-yl)ethyl}phenylsulfamic acid (17): {{1-[1-(ethylthiazol-2-yl)-2-(4-nitrophenyl)ethylcarbamoyl]-2-methylpropyl}carbamic acid tert-butylester, 16, (0.219 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (5 mL) and treated with SO₃-pyridine (0.146 g). The reaction is stirred at room temperature for 5 minutes after which a 7% solution of NH₄OH (30 mL) is added. The mixture is then concentrated and the resulting residue is purified by reverse phase chromatography to afford 0.148 g of the desired product as the ammonium salt. ¹H(CD₃OD): δ 7.08 (s, 4H), 7.02 (s, 1H), 5.43 (s, 1H), 3.85 (s, 1H), 3.28-2.77 (m, 4H), 1.94 (s, 1H), 1.46 (s, 9H), 1.29 (s, 3H, J=7.3 Hz), 0.83 (s, 6H).

The following are further non-limiting examples of the first aspect of Category IV of the present disclosure.

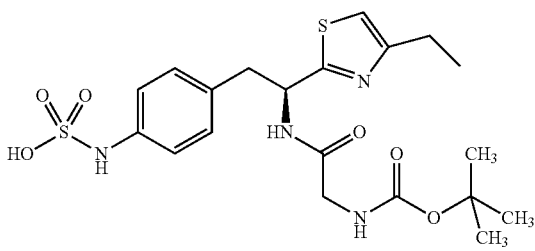 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonylamino)acetamido]2-(4-ethylthiazol-2-yl)ethyl}phenyl-sulfamic acid: ¹H(CD₃OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

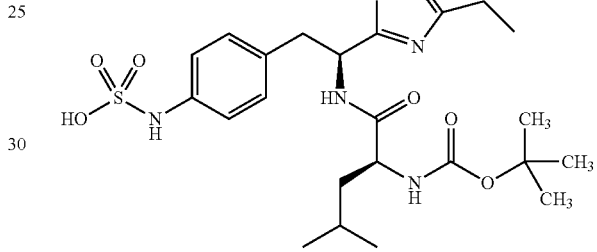

4-{(S)-2-[(S)-2-(tert-Butoxycarbonylamino)-4-methylpentanamido]-2-(4-ethylthiazol-2-yl)ethyl}phenylsulfamic acid: ¹H NMR (CD₃OD) δ 7.19-7.00 (m, 4H), 5.50-5.40 (m, 1H), 4.13-4.06 (m, 1H), 3.32 (1H, A of ABX, J=7.5, 18 Hz), 3.12 (1H, B of ABX, J=8.1, 13.8 Hz), 2.79 (q, 2H, J=7.8, 14.7 Hz), 1.70-1.55 (m, 1H), 1.46 (s, 9H), 1.33 (t, 3H, J=2.7 Hz), 0.92 (q, 6H, J=6, 10.8 Hz).

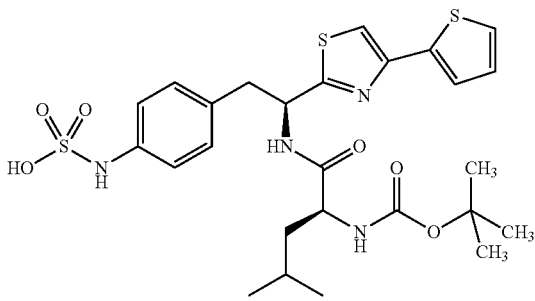 [SMILES: CC(C)C[C@H](NC(=O)OC(C)(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methylpentanamido]-2-[2-(thiophen-2-yl)thiazol-4-yl]ethyl}phenylsulfamic acid: ¹H NMR (CD₃OD) δ 8.06 (d, 1H, J=8.4 Hz), 7.61-7.58 (m, 1H), 7.57 (s, 1H), 7.15 (t, 1H, J=0.6 Hz), 7.09-6.98 (m, 6H), 5.30-5.20 (m, 1H), 4.10-4.00 (m, 1H), 3.19-3.13 (m, 2H), 1.63-1.55 (m, 2H), 1.48-1.33 (m, 10H), 0.95-0.89 (m, 6H).

The following are non-limiting examples of the second aspect of Category IV of the present disclosure.

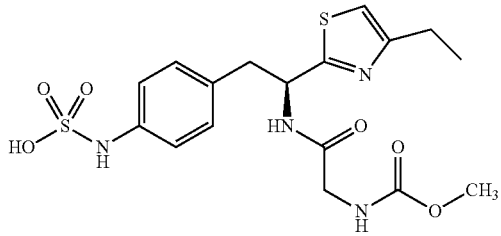 [SMILES: CCc1csc([C@H](Cc2ccc(NS(=O)(=O)O)cc2)NC(=O)CNC(=O)OC)n1]

(S)-4-{2-(4-Ethylthiazol-2-yl)-2-[2-(methoxycarbonylamino)acetamido]ethyl}-phenylsulfamic acid: $^1$H(CD$_3$OD): δ 7.12-7.07 (m, 4H), 7.03 (s, 1H), 5.42 (t, 1H, J=5.7 Hz), 3.83-3.68 (q, 2H, J=11.4 Hz), 3.68 (s, 3H), 3.34-3.04 (m, 2H), 2.83-2.76 (q, 2H, J=7.8 Hz), 1.31 (t, 3H, J=7.5 Hz).

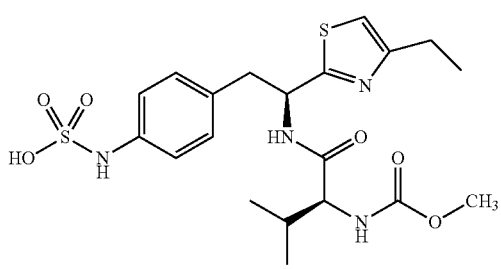 [SMILES: CCc1csc([C@H](Cc2ccc(NS(=O)(=O)O)cc2)NC(=O)[C@@H](NC(=O)OC)C(C)C)n1]

4-{(S)-2-(4-Ethylthiazol-2-yl)-2-[(S)-2-(methoxycarbonylamino)-3-methylbutanamido]-ethyl}phenylsulfamic acid: $^1$H NMR (CD$_3$OD) δ 8.56 (d, 1H, J=7.8 Hz), 7.09 (s, 4H), 7.03 (s, 1H), 5.26-5.20 (m, 1H), 3.90 (d, 1H, J=7.8 Hz), 3.70 (s, 3H), 3.30 (1H, A of ABX, obscured by solvent), 3.08 (1H, B of ABX, J=9.9, 9 Hz), 2.79 (q, 2H, J=11.1, 7.2 Hz), 2.05-1.97 (m, 1H), 1.31 (t, 3H, J=7.5 Hz), 0.88 (s, 3H), 0.85 (s, 3H), 0.79-0.75 (m, 1H).

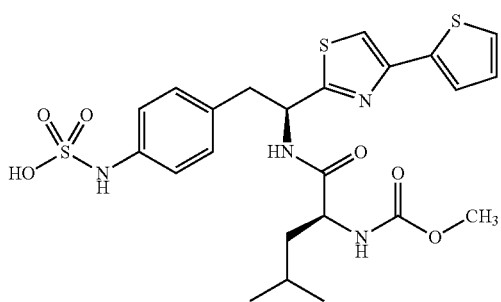 [SMILES: COC(=O)N[C@@H](CC(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methyl-pentanamido]-2-(4-ethylthiazol-2-yl)ethyl}phenylsulfamic acid: $^1$H NMR (CD$_3$OD) δ 7.19-7.00 (m, 4H), 5.50-5.40 (m, 1H), 4.13-4.06 (m, 1H), 3.32 (1H, A of ABX, J=7.5, 18 Hz), 3.12 (1H, B of ABX, J=8.1, 13.8 Hz), 2.79 (q, 2H, J=7.8, 14.7 Hz), 1.70-1.55 (m, 1H), 1.46 (s, 9H), 1.33 (t, 3H, J=2.7 Hz), 0.92 (q, 6H, J=6, 10.8 Hz).

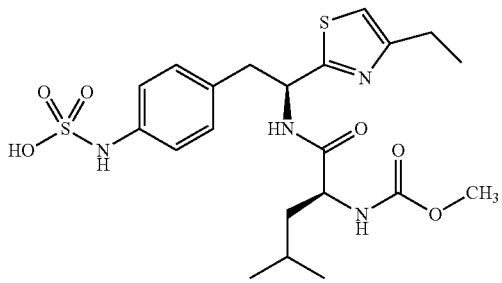 [SMILES: CCc1csc([C@H](Cc2ccc(NS(=O)(=O)O)cc2)NC(=O)[C@H](CC(C)C)NC(=O)OC)n1]

4-{(S)-2-(4-Ethylthiazol-2-yl)-2-[(S)-2-(methoxycarbonylamino)-4-methylpentan-amido]ethyl}phenylsulfamic acid: $^1$H NMR (CD$_3$OD) δ 7.12-7.03 (m, 5H), 6.84 (d, 1H, J=8.4 Hz), 5.40 (t, 1H, J=5.7 Hz), 4.16 (t, 1H, J=6.3 Hz), 3.69 (s, 3H), 3.61-3.55 (m, 1H), 3.29-3.27 (m, 1H), 3.14-3.07 (m, 1H), 2.81 (q, 2H, J=3.9, 11.2 Hz), 1.66-1.59 (m, 1H), 1.48-1.43 (m, 2H), 1.31 (t, 3H, J=4.5 Hz), 0.96-0.90 (m, 6H).

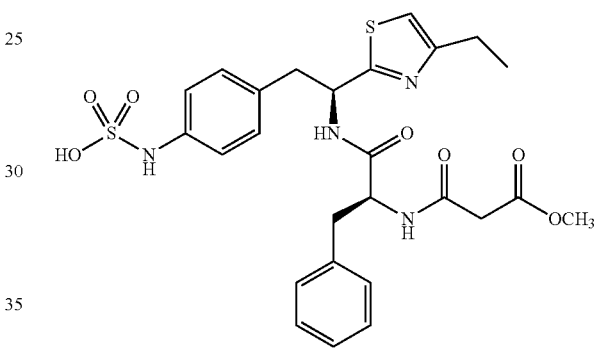

4-((S)-2-(4-Ethylthiazol-2-yl)-2-{(S)-2-[2-(methoxycarbonyl)acetamido]-3-phenylpropanamido}ethyl)phenylsulfamic acid: $^1$H(CD$_3$OD): δ 7.22-7.01 (m, 9H), 6.97 (s, 1H), 5.37-5.32 (m, 1H), 4.64 (t, 1H, J=7.1 Hz), 3.71-3.68 (m, 2H), 3.64 (s, 3H), 3.28-3.26 (m, 1H), 3.03-2.96 (m, 2H), 2.83-2.72 (m, 3H), 1.28 (t, 3H, J=7.5 Hz).

Category V of the present disclosure relates to compounds having the formula:

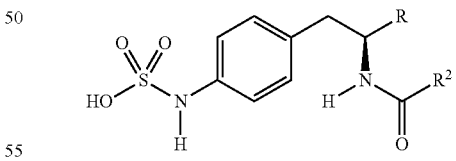

wherein R is a substituted or unsubstituted thiophene-2-yl or thiophene-4-yl unit and non-limiting examples of R$^2$ are further described in Table VII.

TABLE VII

| No. | R | R$^2$ |
|---|---|---|
| 151 | thiazol-2-yl | —OC(CH$_3$)$_3$ |
| 152 | 4-methylthiazol-2-yl | —OC(CH$_3$)$_3$ |
| 153 | 4-ethylthiazol-2-yl | —OC(CH$_3$)$_3$ |

TABLE VII-continued

| No. | R | R² |
|---|---|---|
| 154 | 4-cyclopropylthiazol-2-yl | —OC(CH₃)₃ |
| 155 | 4-tert-butylthiazol-2-yl | —OC(CH₃)₃ |
| 156 | 4-cyclohexylthiazol-2-yl | —OC(CH₃)₃ |
| 157 | 4-(2,2,2-trifluoroethyl)thiazol-2-yl | —OC(CH₃)₃ |
| 158 | 4-(3,3,3-trifluoropropyl)thiazol-2-yl | —OC(CH₃)₃ |
| 159 | 4-(2,2-difluorocyclopropyl)thiazol-2-yl | —OC(CH₃)₃ |
| 160 | 4,5-dimethylthiazol-2-yl | —OC(CH₃)₃ |
| 161 | 4-methyl-5-ethylthiazol-2-yl | —OC(CH₃)₃ |
| 162 | 4-phenylthiazol-2-yl | —OC(CH₃)₃ |
| 163 | 4-(4-chlorophenyl)thiazol-2-yl | —OC(CH₃)₃ |
| 164 | 4-(3,4-dimethylphenyl)thiazol-2-yl | —OC(CH₃)₃ |
| 165 | 4-methyl-5-phenylthiazol-2-yl | —OC(CH₃)₃ |
| 166 | 4-(thiophene-2-yl)thiazol-2-yl | —OC(CH₃)₃ |
| 167 | thiazol-4-yl | —OC(CH₃)₃ |
| 168 | 2-methylthiazol-4-yl | —OC(CH₃)₃ |
| 169 | 2-ethylthiazol-4-yl | —OC(CH₃)₃ |
| 170 | 2-cyclopropylthiazol-4-yl | —OC(CH₃)₃ |
| 171 | 2-tert-butylthiazol-4-yl | —OC(CH₃)₃ |
| 172 | 2-cyclohexylthiazol-4-yl | —OC(CH₃)₃ |
| 173 | 2-(2,2,2-trifluoroethyl)thiazol-4-yl | —OC(CH₃)₃ |
| 174 | 2-(3,3,3-trifluoropropyl)thiazol-4-yl | —OC(CH₃)₃ |
| 175 | 2-(2,2-difluorocyclopropyl)thiazol-4-yl | —OC(CH₃)₃ |
| 178 | 2-phenylthiazol-4-yl | —OC(CH₃)₃ |
| 179 | 2-(4-chlorophenyl)thiazol-4-yl | —OC(CH₃)₃ |
| 180 | 2-(3,4-dimethylphenyl)thiazol-4-yl | —OC(CH₃)₃ |
| 182 | 2-(thiophene-2-yl)thiazol-4-yl | —OC(CH₃)₃ |
| 183 | thiazol-2-yl | —OCH₃ |
| 184 | 4-methylthiazol-2-yl | —OCH₃ |
| 185 | 4-ethylthiazol-2-yl | —OCH₃ |
| 186 | 4-cyclopropylthiazol-2-yl | —OCH₃ |
| 187 | 4-tert-butylthiazol-2-yl | —OCH₃ |
| 188 | 4-cyclohexylthiazol-2-yl | —OCH₃ |
| 189 | 4-(2,2,2-trifluoroethyl)thiazol-2-yl | —OCH₃ |
| 190 | 4-(3,3,3-trifluoropropyl)thiazol-2-yl | —OCH₃ |
| 191 | 4-(2,2-difluorocyclopropyl)thiazol-2-yl | —OCH₃ |
| 192 | 4,5-dimethylthiazol-2-yl | —OCH₃ |
| 193 | 4-methyl-5-ethylthiazol-2-yl | —OCH₃ |
| 194 | 4-phenylthiazol-2-yl | —OCH₃ |
| 195 | 4-(4-chlorophenyl)thiazol-2-yl | —OCH₃ |
| 196 | 4-(3,4-dimethylphenyl)thiazol-2-yl | —OCH₃ |
| 197 | 4-methyl-5-phenylthiazol-2-yl | —OCH₃ |
| 198 | 4-(thiophene-2-yl)thiazol-2-yl | —OCH₃ |
| 199 | thiazol-4-yl | —OCH₃ |
| 200 | 2-methylthiazol-4-yl | —OCH₃ |
| 201 | 2-ethylthiazol-4-yl | —OCH₃ |
| 202 | 2-cyclopropylthiazol-4-yl | —OCH₃ |
| 203 | 2-tert-butylthiazol-4-yl | —OCH₃ |
| 204 | 2-cyclohexylthiazol-4-yl | —OCH₃ |
| 205 | 2-(2,2,2-trifluoroethyl)thiazol-4-yl | —OCH₃ |
| 206 | 2-(3,3,3-trifluoropropyl)thiazol-4-yl | —OCH₃ |
| 207 | 2-(2,2-difluorocyclopropyl)thiazol-4-yl | —OCH₃ |
| 210 | 2-phenylthiazol-4-yl | —OCH₃ |
| 211 | 2-(4-chlorophenyl)thiazol-4-yl | —OCH₃ |
| 212 | 2-(3,4-dimethylphenyl)thiazol-4-yl | —OCH₃ |
| 214 | 2-(thiophene-2-yl)thiazol-4-yl | —OCH₃ |
| 215 | thiazol-2-yl | —CH₃ |
| 216 | 4-methylthiazol-2-yl | —CH₃ |
| 217 | 4-ethylthiazol-2-yl | —CH₃ |
| 218 | 4-cyclopropylthiazol-2-yl | —CH₃ |
| 219 | 4-tert-butylthiazol-2-yl | —CH₃ |
| 220 | 4-cyclohexylthiazol-2-yl | —CH₃ |
| 221 | 4-(2,2,2-trifluoroethyl)thiazol-2-yl | —CH₃ |
| 222 | 4-(3,3,3-trifluoropropyl)thiazol-2-yl | —CH₃ |
| 223 | 4-(2,2-difluorocyclopropyl)thiazol-2-yl | —CH₃ |
| 224 | 4,5-dimethylthiazol-2-yl | —CH₃ |
| 225 | 4-methyl-5-ethylthiazol-2-yl | —CH₃ |
| 226 | 4-phenylthiazol-2-yl | —CH₃ |
| 227 | 4-(4-chlorophenyl)thiazol-2-yl | —CH₃ |
| 228 | 4-(3,4-dimethylphenyl)thiazol-2-yl | —CH₃ |
| 229 | 4-methyl-5-phenylthiazol-2-yl | —CH₃ |
| 230 | 4-(thiophene-2-yl)thiazol-2-yl | —CH₃ |
| 231 | thiazol-4-yl | —CH₃ |
| 232 | 2-methylthiazol-4-yl | —CH₃ |
| 233 | 2-ethylthiazol-4-yl | —CH₃ |
| 234 | 2-cyclopropylthiazol-4-yl | —CH₃ |
| 235 | 2-tert-butylthiazol-4-yl | —CH₃ |
| 236 | 2-cyclohexylthiazol-4-yl | —CH₃ |
| 237 | 2-(2,2,2-trifluoroethyl)thiazol-4-yl | —CH₃ |
| 238 | 2-(3,3,3-trifluoropropyl)thiazol-4-yl | —CH₃ |
| 239 | 2-(2,2-difluorocyclopropyl)thiazol-4-yl | —CH₃ |
| 242 | 2-phenylthiazol-4-yl | —CH₃ |
| 243 | 2-(4-chlorophenyl)thiazol-4-yl | —CH₃ |
| 244 | 2-(3,4-dimethylphenyl)thiazol-4-yl | —CH₃ |
| 246 | 2-(thiophene-2-yl)thiazol-4-yl | —CH₃ |

The compounds encompassed within Category V of the present disclosure can be prepared by the procedure outlined in Scheme VI and described in Example 7 herein below.

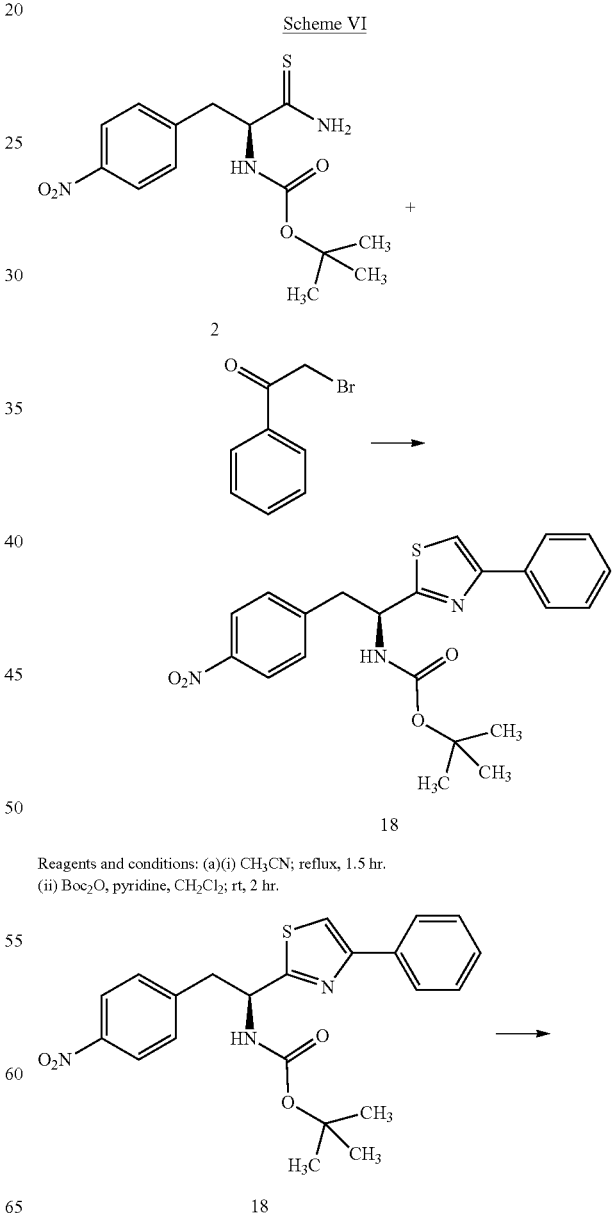

Scheme VI

Reagents and conditions: (a)(i) CH₃CN; reflux, 1.5 hr.
(ii) Boc₂O, pyridine, CH₂Cl₂; rt, 2 hr.

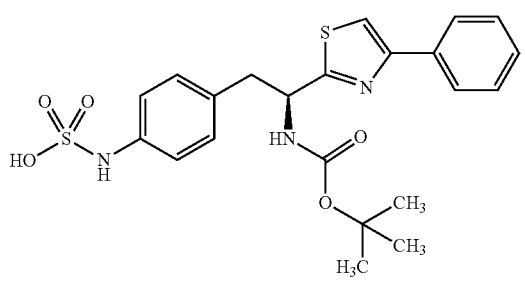

19

Reagents and conditions: (b)(i) H₂:Pd/C, MeOH; reflux
(ii) SO₃-pyridine, NH₄OH; rt, 12 hr.

Example 7

[1-(S)-(Phenylthiazol-2-yl)-2-(4-sulfoaminophenyl)ethyl]-carbamic acid tert-butyl ester (19)

Preparation of [2-(4-nitrophenyl)-1-(S)-(4-phenylthiazol-2-yl)ethyl]-carbamic acid tert-butyl ester (18): A mixture of [2-(4-nitrophenyl)-1-(S)-thiocarbamoylethyl]-carbamic acid tert-butyl ester, 2, (0.343 g, 1.05 mmol), 2-bromo-acetophenone (0.231 g, 1.15 mmol), in CH₃CN (5 mL) is refluxed 1.5 hour. The solvent is removed under reduced pressure and the residue re-dissolved in CH₂Cl₂ then pyridine (0.24 mL, 3.0 mmol) and Boc₂O (0.24 mL, 1.1 mmol) are added. The reaction is stirred for 2 hours and diethyl ether is added to the solution and the precipitate which forms is removed by filtration. The organic layer is dried (Na₂SO₄), filtered, and concentrated to a residue which is purified over silica to afford 0.176 g (39%) of the desired product ESI+MS 426 (M+1).

Preparation of [1-(S)-(phenylthiazol-2-yl)-2-(4-sulfoaminophenyl)ethyl]-carbamic acid tert-butyl ester (19): [2-(4-nitrophenyl)-1-(S)-(4-phenylthiazol-2-yl)ethyl]-carbamic acid tert-butyl ester, 18, (0.176 g, 0.41 mmol) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.195 g, 1.23 mmol). The reaction is stirred at room temperature for 5 minutes after which a 7% solution of NH₄OH (10 mL) is added. The mixture is then concentrated and the resulting residue is purified by reverse phase chromatography to afford 0.080 g of the desired product as the ammonium salt. ¹H NMR (300 MHz, MeOH-d₄) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

The following are further non-limiting examples of Category V of the present disclosure.

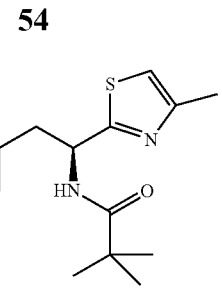

(S)-4-(2-(4-Methylthiazol-2-yl)-2-pivalamidoethyl)phenylsulfamic acid: ¹H (CD₃OD): δ 7.31 (s, 4H), 7.20 (s, 1H), 5.61-5.56 (m, 1H), 3.57-3.22 (m, 2H), 2.62 (s, 3H), 1.31 (s, 3H).

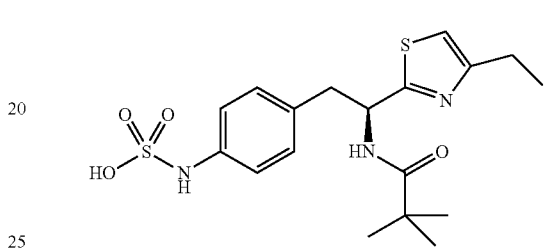

(S)-4-(2-(4-Ethylthiazol-2-yl)-2-pivalamidoethyl)phenylsulfamic acid: ¹H NMR (300 MHz, MeOH-d₄) δ 7.92 (d, J=8.1 Hz, 1H), 7.12-7.14 (m, 4H), 7.03 (s, 1H), 5.38-5.46 (m, 1H), 3.3-3.4 (m, 1H), 3.08 (dd, J=10.2 and 13.8 Hz, 1H), 2.79 (q, J=7.2 Hz, 2H), 1.30 (t, J=7.2 Hz, 3H), 1.13 (s, 9H).

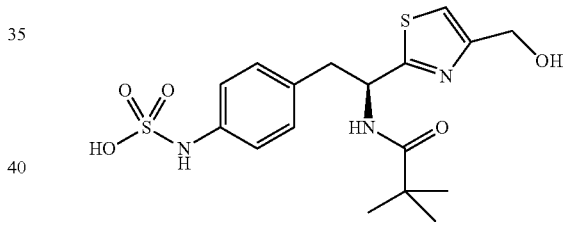

(S)—N-(1-(4-Hydroxymethyl)thiazol-2-yl)-2-pivalamidoethyl)phenylsulfamic acid: ¹H NMR (300 MHz, MeOH-d₄) δ 7.92 (d, J=8.1 Hz, 1H), 7.24 (s, 1H), 7.08 (d, J=8.7 Hz, 2H), 7.00 (d, J=8.7 Hz, 2H), 5.29-5.37 (m, 1H), 4.55 (s, 2H), 3.30 (dd, J=4.8 and 13.5 Hz, 1H), 2.99 (dd, J=10.5 and 13.5 Hz, 1H), 0.93 (s, 9H).

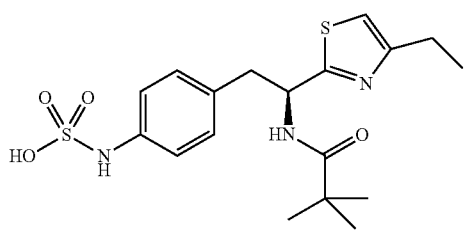 [SMILES: CCc1csc([C@H](Cc2ccc(NS(=O)(=O)O)cc2)NC(=O)C(C)(C)C)n1]

(S)-4-(2-(4-Ethoxycarbonyl)thiazol-2-yl)-2-pivalamideoethyl)phenylsulfamic acid: ¹H NMR (300 MHz, MeOH-d₄) δ 8.30 (s, 1H), 8.04 (d, J=8.1 Hz, 1H), 7.13 (s, 4H), 5.41-5.49 (m, 1H), 4.41 (q, J=7.2 Hz, 2H), 3.43 (dd, J=5.1 and 13.8 Hz, 1H), 3.14 (dd, J=5.7 and 9.9 Hz, 1H), 1.42 (t, J=7.2 Hz, 3H), 1.14 (s, 9H).

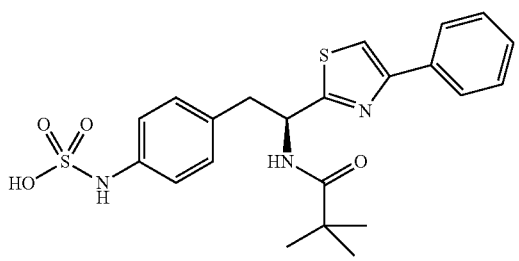 [SMILES: CC(C)(C)C(=O)N[C@@H](Cc1ccc(NS(=O)(=O)O)cc1)c1nc(-c2ccccc2)cs1]

(S)-4-(2-(4-Phenylthiazol-2-yl)-2-pivalamidoethyl)phenylsulfamic acid: $^1$H NMR (300 MHz, MeOH-d$_4$) δ 7.94-8.01 (m, 3H), 7.70 (s, 1H), 7.42-7.47 (m, 2H), 7.32-7.47 (m, 1H), 7.13-7.20 (m, 3H), 5.48-5.55 (m, 1H), 3.50 (dd, J=5.1 and 14.1 Hz, 1H), 3.18 (dd, J=10.2 and 14.1 Hz, 1H), 1.67 (s, 9H).

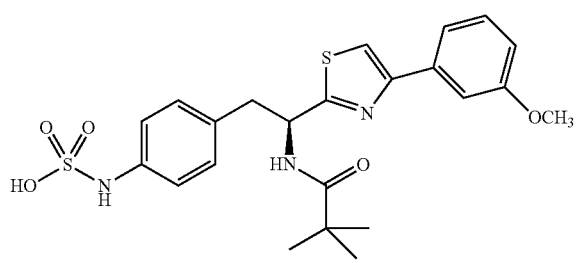 [SMILES: COc1cccc(-c2csc([C@H](Cc3ccc(NS(=O)(=O)O)cc3)NC(=O)C(C)(C)C)n2)c1]

4-((S)-2-(4-(3-Methoxyphenyl)thiazol-2-yl)-2-pivalamidoethyl)phenylsulfamic acid: $^1$H(CD$_3$OD): δ 7.96-7.93 (d, 1H, J=8.1 Hz), 7.69 (s, 1H), 7.51-7.49 (d, 2H, J=7.9 Hz), 7.33 (t, 1H, J=8.0 Hz), 7.14 (s, 4H), 6.92-6.90 (d, 1H, J=7.8 Hz), 5.50 (t, 1H, J=5.1 Hz), 3.87 (s, 3H), 3.50-3.13 (m, 2H), 1.15 (s, 9H).

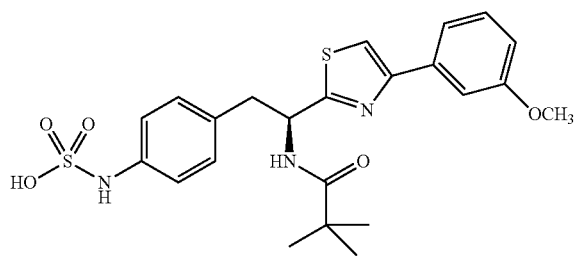 [SMILES: COc1cccc(-c2csc([C@H](Cc3ccc(NS(=O)(=O)O)cc3)NC(=O)C(C)(C)C)n2)c1]

4-((S)-2-(4-(3-methoxyphenyl)thiazol-2-yl)-2-pivalamidoethyl)phenylsulfamic acid: $^1$H(CD$_3$OD): δ 7.98-7.85 (m, 3H), 7.53 (s, 1H), 7.26-7.12 (m, 3H), 7.03-6.98 (m, 2H), 5.54-5.46 (m, 1H), 3.52-3.13 (m, 2H), 1.15 (s, 9H).

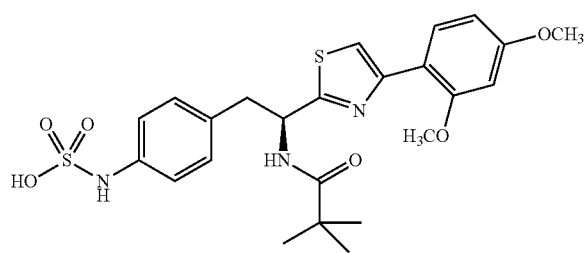 [SMILES: COc1ccc(-c2csc([C@H](Cc3ccc(NS(=O)(=O)O)cc3)NC(=O)C(C)(C)C)n2)c(OC)c1]

4-((S)-2-(4-(2,4-Dimethoxyphenyl)thiazol-2-yl)-2-pivalamidoethyl)phenyl-sulfamic acid: $^1$H(CD$_3$OD): δ 8.11-8.09 (d, 1H, J=7.8 Hz), 7.96-7.93 (d, 1H, J=8.4 Hz), 7.74 (s, 1H), 7.18-7.16 (m, 4H), 6.67-6.64 (d, 2H, J=9.0 Hz), 5.55-5.47 (m, 1H), 3.95 (s, 3H), 3.87 (s, 3H), 3.52-3.13 (m, 2H), 1.17 (s, 9H).

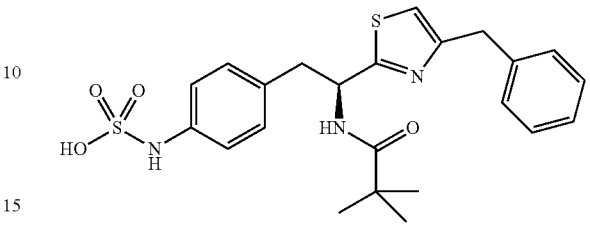

(S)-4-(2-(4-Benzylthiazol-2-yl)-2-pivalamidoethyl)phenylsulfamic acid $^1$H NMR (CD$_3$OD) δ 7.85 (d, 1H, J=8.4 Hz), 7.38-7.20 (m, 4H), 7.11-7.02 (m, 1H), 7.00 (s, 1H), 5.42-5.37 (m, 1H), 4.13 (s, 2H), 3.13-3.08 (m, 2H), 1.13 (s, 9H).

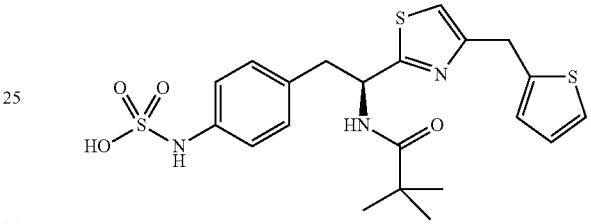

(S)-4-(2-Pivalamido-2-(4-(thiophen-2-ylmethyl)thiazol-2-yl)ethyl)phenylsulfamic acid: $^1$H NMR (CD$_3$OD) δ 7.88-7.85 (d, 1H), 7.38-7.35 (m, 1H), 7.10-7.01 (m, 4H), 7.02 (s, 1H), 5.45-5.38 (m, 1H), 4.13 (s, 2H), 3.13-3.05 (m, 2H), 1.13 (2, 9H).

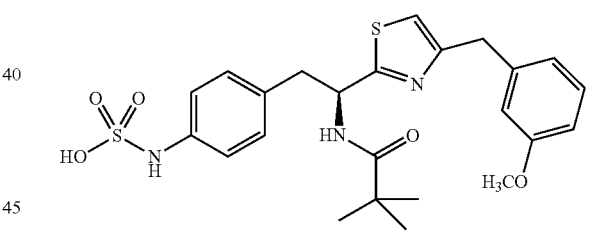

(S)-4-(2-(4-(3-Methoxybenzyl)thiazol-2-yl)-2-pivalamidoethyl)phenylsulfamic acid: $^1$H NMR (CD$_3$OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

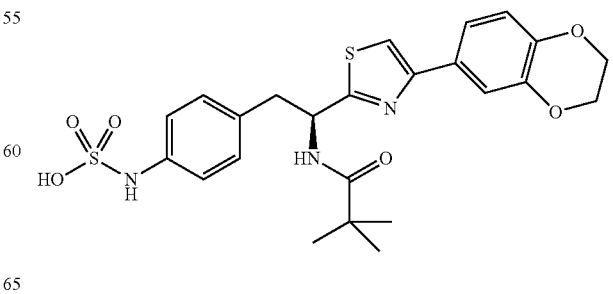

4-((S)-2-(4-(2,3-Dihydrobenzo[b][1,4]dioxin-6-yl)thiazol-2-yl)-2-pivalamidoethyl)phenylsulfamic acid:

¹H(CD₃OD): δ 7.53 (s, 1H), 7.45 (s, 1H), 7.42-7.40 (d, 1H, J=8.4 Hz), 7.19-7.15 (m, 4H), 6.91-6.88 (d, 2H, J=8.4 Hz), 5.51-5.46 (m, 1H), 4.30 (s, 4H), 3.51-3.12 (m, 2H), 1.16 (s, 9H).

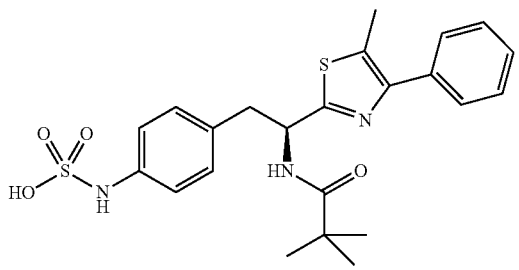 [SMILES: Cc1sc([C@H](Cc2ccc(NS(=O)(=O)O)cc2)NC(=O)C(C)(C)C)nc1-c1ccccc1]

(S)-4-(2-(5-Methyl-4-phenylthiazol-2-yl)-2-pivalamido-ethyl)phenylsulfamic acid: ¹H(CD₃OD): δ 7.63-7.60 (d, 2H, J=7.1 Hz), 7.49-7.35 (m, 3H), 7.14 (s, 4H), 5.43-5.38 (m, 1H), 3.42-3.09 (m, 2H), 2.49 (s, 3H), 1.14 (s, 9H).

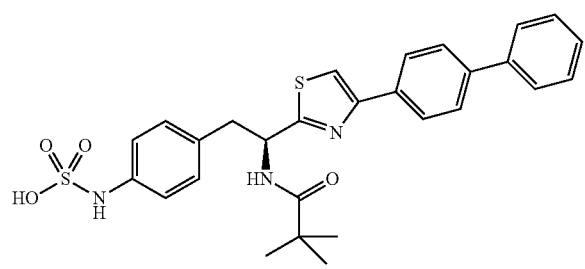 [SMILES: CC(C)(C)C(=O)N[C@@H](Cc1ccc(NS(=O)(=O)O)cc1)c1nc(-c2ccc(-c3ccccc3)cc2)cs1]

(S)-4-(2-(4-(Biphenyl-4-yl)thiazol-2-yl)-2-pivalamidoethyl)-phenylsulfamic acid: ¹H(CD₃OD): δ 8.04-8.01 (m, 2H), 7.72-7.66 (m, 5H), 7.48-7.35 (m, 3H), 7.15 (s, 4H), 5.50 (t, 1H, J=5.0 Hz), 3.57-3.15 (d, 2H), 1.16 (s, 9H).

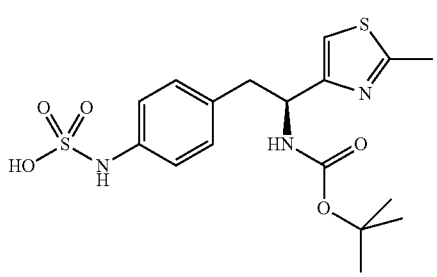 [SMILES: Cc1nc([C@H](Cc2ccc(NS(=O)(=O)O)cc2)NC(=O)OC(C)(C)C)cs1]

(S)-4-(2-(tert-Butoxycarbonylamino)-2-(2-methylthaizol-4-yl)ethyl)phenylsulfamic acid: ¹H NMR (300 MHz, D₂O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

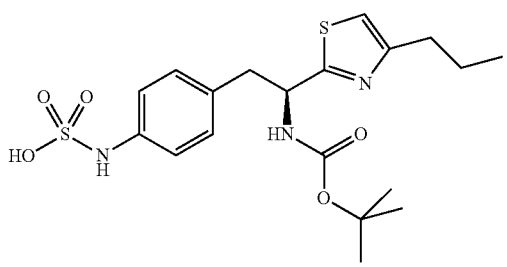 [SMILES: CCCc1csc([C@H](Cc2ccc(NS(=O)(=O)O)cc2)NC(=O)OC(C)(C)C)n1]

(S)-4-(2-(tert-Butoxycarbonyl)-2-(4-propylthiazol-2-yl)ethyl)-phenyl sulfamic acid: ¹H NMR (300 MHz, CD₃OD): δ 7.18-7.02 (m, 5H), 5.06-5.03 (m, 1H), 3.26 (dd, J=13.8, 4.8 Hz, 1H), 2.95 (dd, J=13.8, 9.3 Hz, 1H), 2.74 (dd, J=15.0, 7.2 Hz, 2H), 1.81-1.71 (m, 2H), 1.40 (s, 7H), 1.33 (bs, 2H), 0.988 (t, J=7.5 Hz 3H).

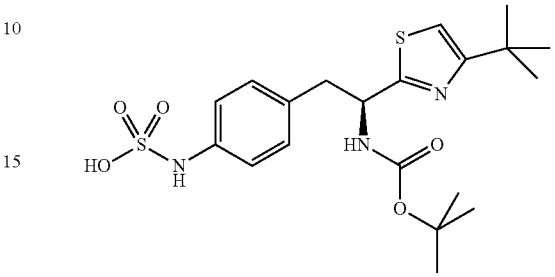

(S)-4-(2-(tert-Butoxycarbonyl)-2-(4-tert-butylthiazol-2-yl)ethyl)-phenyl sulfamic acid: ¹H NMR (300 MHz, CD₃OD): δ 7.12 (s, 4H), 7.01 (s, 1H), 5.11-5.06 (m, 1H), 3.32-3.25 (m, 1H), 2.96 (m, 1H), 1.42 (s, 8H), 1.38 (s, 9H), 1.32 (s, 1H).

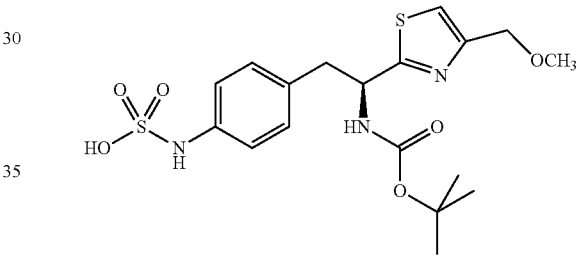

(S)-4-(2-(tert-Butoxycarbonyl)-2-(4-(methoxymethyl)thiazol-2-yl)ethyl)-phenyl sulfamic acid: ¹H NMR (300 MHz, CD₃OD): δ 7.36 (s, 1H), 7.14-7.05 (m, 4H), 5.06 (dd, J=9.0, 5.1 Hz, 1H), 4.55 (s, 2H), 3.42 (s, 3H), 3.31-3.24 (m, 1H), 2.97 (dd, J=13.8, 9.9 Hz, 1H), 1.47-1.31 (m, 9H).

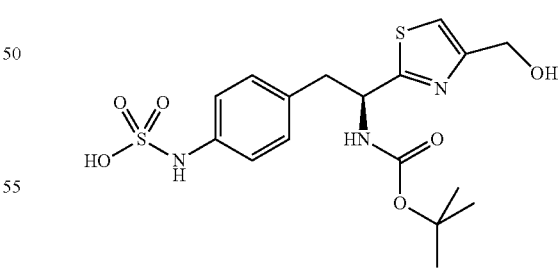

(S)-4-(2-tert-Butoxycarbonyl)-2-(4-(2-hydroxymethyl)thiazol-2 yl)ethyl)phenylsulfamic acid: ¹H NMR (300 MHz, MeOH-d₄) δ 7.22-7.25 (m, 1H), 7.09-7.15 (m, 4H), 5.00-5.09 (m, 1H), 4.32-4.35 (m, 1H), 3.87 (t, J=6.6 Hz, 2H), 3.23-3.29 (m, 1H), 3.09-3.18 (m, 1H), 2.98 (t, J=6.6 Hz, 2H), 1.41 (s, 9H).

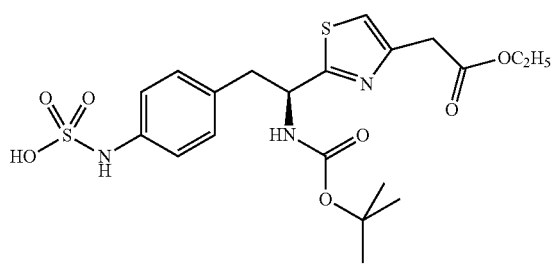 [SMILES: CCOC(=O)Cc1csc([C@H](Cc2ccc(NS(=O)(=O)O)cc2)NC(=O)OC(C)(C)C)n1]

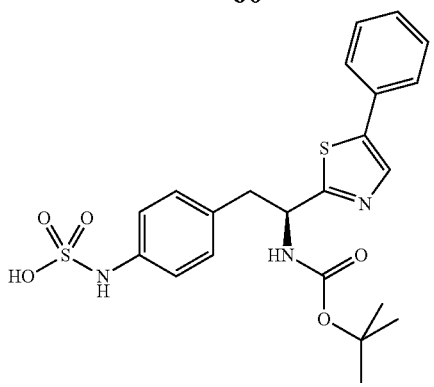

(S)-4-(2-tert-Butoxycarbonyl)-2-(4-(2-ethoxy-2-oxoethyl)-thiazole-2-yl)-ethyl)phenylsulfamic acid: ¹H NMR (300 MHz, MeOH-d₄) δ 7.29 (s, 1H), 7.09-7.16 (m, 4H), 5.04-5.09 (m, 1H), 4.20 (q, J=6.9 Hz, 2H), 3.84 (s, 2H), 3.30 (dd, J=4.8 and 14.1 HZ, 1H), 2.97 (dd, J=9.6 Hz and 13.8 Hz, 1H), 1.41 (s, 9H), 1.29 (t, J=7.2 Hz, 3H).

(S)-4-(2-(tert-Butoxycarbonylamino)-2-(5-phenylthiazol-2-yl)ethyl)-phenyl sulfamic acid: ¹H NMR (300 MHz, CD₃OD): δ 7.98 (s, 1H), 7.62 (d, J=7.2 Hz, 2H), 7.46-7.35 (m, 4H), 7.14 (s, 4H), 5.09 (bs, 1H), 3.07-2.99 (m, 2H), 1.43 (s, 9H).

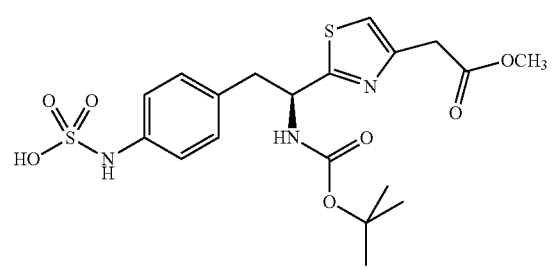 [SMILES: COC(=O)Cc1csc([C@H](Cc2ccc(NS(=O)(=O)O)cc2)NC(=O)OC(C)(C)C)n1]

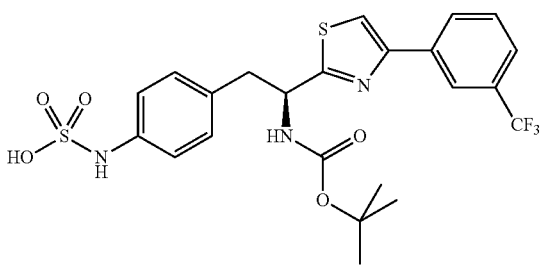 [SMILES: CC(C)(C)OC(=O)N[C@@H](Cc1ccc(NS(=O)(=O)O)cc1)c1nc(-c2cccc(C(F)(F)F)c2)cs1]

(S)-4-(2-(tert-Butoxycarbonyl)-2-(4-(2-(2-methoxy-2-oxoethyl amino)-2-oxoethyl)thiazole-2-yl)ethyl)phenylsulfamic acid: ¹H NMR (300 MHz, MeOH-d₄) δ 7.31 (s, 1H), 7.01-7.16 (m, 4H), 5.04-5.09 (m, 1H), 4.01 (s, 2H), 3.78 (s, 2H), 3.74 (s, 3H), 3.29 (dd, J=5.1 and 13.8 Hz, 1H), 2.99 (dd, J=9.3 and 13.8 Hz, 1H), 1.41 (s, 9H).

4-((S)-2-(tert-Butoxycarbonylamino)-2-(4-(3-(trifluoromethyl)phenyl)thiazol-2-yl)ethyl)-phenyl sulfamic acid: ¹H NMR (300 MHz, CD₃OD): δ 8.28 (s, 1H), 8.22-8.19 (m, 1H), 7.89 (s, 1H), 7.65 (d, J=5.1 Hz, 2H), 7.45 (d, J=8.1 Hz, 1H), 7.15 (s, 4H), 5.17-5.14 (m, 1H), 3.43-3.32 (m, 1H), 3.05 (dd, J=14.1, 9.6 Hz, 1H), 1.42 (s, 9H).

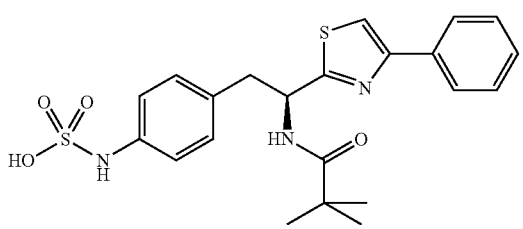 [SMILES: CC(C)(C)C(=O)N[C@@H](Cc1ccc(NS(=O)(=O)O)cc1)c1nc(-c2ccccc2)cs1]

(S)-4-(2-(tert-Butoxycarbonylamino)-2-(5-phenylthiazol-2-yl)ethyl)-phenyl sulfamic acid: ¹H NMR (300 MHz, CD₃OD): δ 7.98 (s, 1H), 7.94 (d, J=7.2 Hz, 2H), 7.46-7.35 (m, 4H), 7.14 (s, 4H), 5.09 (bs, 1H), 3.07-2.99 (m, 2H), 1.43 (s, 9H).

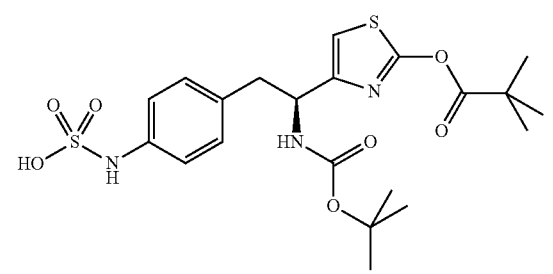

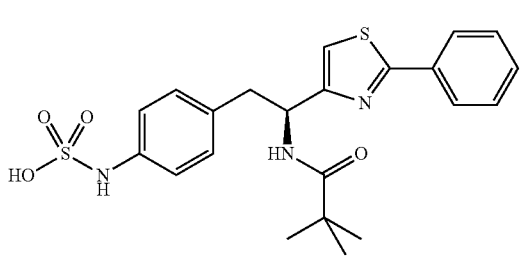 [SMILES: CC(C)(C)C(=O)N[C@@H](Cc1ccc(NS(=O)(=O)O)cc1)c1csc(-c2ccccc2)n1]

(S)-4-(2-(tert-Butoxycarbonylamino)-2-(2-(pivaloyloxy) thiazol-4-yl)ethyl)phenyl-sulfamic acid: ¹H NMR (300 MHz, D₂O) δ 6.95 (s, 4H), 6.63 (s, 1H), 2.94 (dd, J=13.5 and 4.8 Hz, 1H), 2.75 (dd, J=13.5 and 4.8 Hz, 1H), 1.16 (s, 9H), 1.13 (s, 9H).

(S)-{4-[2,2-Dimethyl-propionylamino)-2-(2-phenyl-thiazole-4-yl)ethyl]phenyl}-sulfamic acid: $^1$H NMR (300 MHz, MeOH-d$_4$) δ 7.92-7.96 (m, 2H), 7.65 (d, J=8.4 Hz, 1H), 7.45-7.49 (m, 3H), 7.18 (s, 1H), 7.08-7.15 (m, 4H), 5.34-5.41 (m, 1H), 3.26 (dd, J=14.1 and 6.0 Hz, 1H), 3.08 (dd, J=13.8 and 9.0 Hz, 1H), 1.47 (s, 9H).

(S)-4-(2-tert-Butoxycarbonylamido)-2-(4-phenyl)-2-(4-phenylthiazole-2-yl)ethyl)-phenylsulfamic acid: $^1$H NMR (300 MHz, MeOH-d$_4$) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

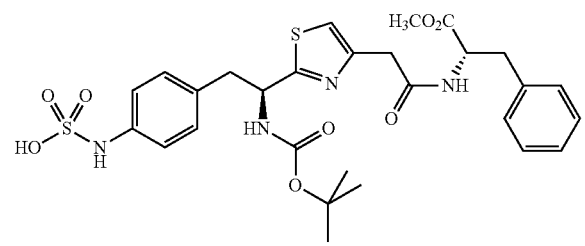 [SMILES: COC(=O)[C@H](Cc1ccccc1)NC(=O)Cc1csc([C@H](Cc2ccc(NS(=O)(=O)O)cc2)NC(=O)OC(C)(C)C)n1]

(S,S)-2-(2-{2-[2-tert-Butoxycarbonylamino-2-(4-sulfoaminophenyl)ethyl]thiazol-4-yl}acetylamido)-3-phenyl-propionic acid methyl ester: $^1$H NMR (300 MHz, MeOH-d$_4$) δ 6.85-6.94 (m, 9H), 6.64 (s, 1H), 4.83 (s, 1H), 4.54-4.58 (m, 1H), 3.49 (s, 3H), 3.39 (s, 2H), 2.80-2.97 (m, 1H), 2.64-2.78 (m, 1H), 1.12 (s, 9H).

(S)-[1-{1-Oxo-4-[2-(1-phenyl-1H-tetrazol-5-sulfonyl)ethyl]-1H-1λ$^4$-thiazol-2-yl}-2-(4-sulfamino-phenyl)-ethyl]-carbamic acid tert-butyl ester: $^1$H NMR (300 MHz, MeOH-d$_4$) δ 7.22-7.75 (m, 2H), 7.62-7.69 (m, 2H), 7.55 (s, 1H), 7.10-7.20 (m, 5H), 5.25 (m, 1H), 4.27-4.36 (m, 1H), 4.11-4.21 (m, 1H), 3.33-3.44 (m, 4H), 2.84-2.90 (m, 1H), 1.33 (s, 9H).

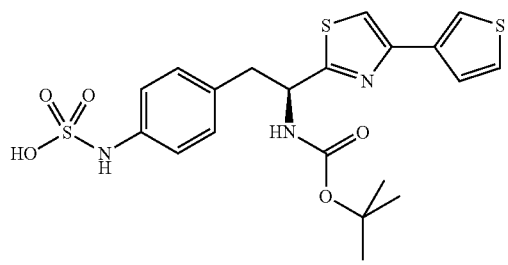 [SMILES: CC(C)(C)OC(=O)N[C@@H](Cc1ccc(NS(=O)(=O)O)cc1)c1nc(-c2ccsc2)cs1]

4-((S)-2-(tert-Butoxycarbonylamino)-2-(4-(thiophen-3-yl)thiazol-2-yl)ethyl)phenyl sulfamic acid: $^1$H NMR (300 MHz, CD$_3$OD): δ 7.84 (dd, J=3.0, 1.5 Hz, 1H), 7.57-7.55 (m, 2H), 7.47 (dd, J=4.8, 3.0 Hz, 1H), 7.15 (s, 4H), 5.15-5.10 (m, 1H), 3.39-3.34 (m, 1H), 3.01 (dd, J=14.1, 9.6 Hz, 1H), 1.42 (s, 8H), 1.32 (s, 1H).

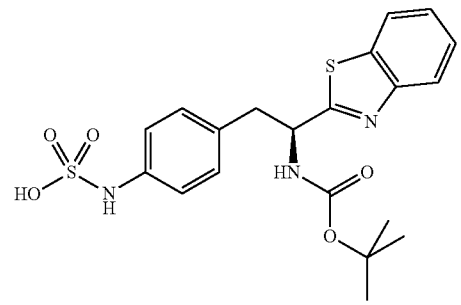 [SMILES: CC(C)(C)OC(=O)N[C@@H](Cc1ccc(NS(=O)(=O)O)cc1)c1nc2ccccc2s1]

(S)-4-(2-(Benzo[d]thiazol-2-ylamino)-2-(tert-butoxycarbonylamino)ethyl)-phenylsulfamic acid: $^1$H NMR (CD$_3$OD) δ 7.86-7.82 (m, 2H), 7.42 (t, 2H, J=7.1 Hz), 7.33 (t, 1H, J=8.2 Hz), 7.02 (s, 4H), 5.10-5.05 (m, 1H), 2.99-2.91 (m, 2H), 1.29 (s, 9H).

(S)-4-(2-tert-Butoxycarbonylamino)-2-(2-methylthiazol-4-yl)-phenylsulfamic acid $^1$H NMR (300 MHz, D$_2$O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

Regulation of HPTP-β provides a means for modulating the activity of angiopoietin receptor-type tyrosine kinase Tie-2, and thereby mediate disease states wherein angiogenesis is improperly regulated by the human body. The compounds of the present disclosure serve as a means for providing regulation of angiogenesis. As such the present disclosure addresses several unmet medical needs, inter alia;

1) Providing compositions effective as human protein tyrosine phosphatase beta (HPTP-β) inhibitors; and thereby provide a means for regulating angiogenesis in a disorder wherein angiogenesis is elevated;
2) Providing compositions effective as human protein tyrosine phosphatase beta (HPTP-β) inhibitors; and thereby provide a means for regulating angiogenesis in a disorder; and
3) Providing compositions effective human protein tyrosine phosphatase (HPTP-β) inhibitors; and thereby provide a means for regulating angiogenesis in a disorder wherein angiogenesis is decreased.

For purposes of the present disclosure the term "regulate" is defined as in its accepted dictionary meanings. Thus, the meaning of the term "regulate" includes, but is not limited to, up-regulate or down-regulate, to fix, to bring order or uniformity, to govern, or to direct by various means. In one aspect, an antibody may be used in a method for the treatment of an "angiogenesis elevated disorder" or "angiogenesis reduced disorder". As used herein, an "angiogenesis elevated disorder" is one that involves unwanted or elevated angiogenesis in the biological manifestation of the disease, disorder, and/or condition; in the biological cascade leading to the disorder; or as a symptom of the disorder. Similarly, the "angiogenesis reduced disorder" is one that involves wanted or reduced angiogenesis in the biological manifestations. This "involvement" of angiogenesis in an angiogenesis elevated/reduced disorder includes, but is not limited to, the following:

1. The angiogenesis as a "cause" of the disorder or biological manifestation, whether the level of angiogenesis is elevated or reduced genetically, by infection, by autoimmunity, trauma, biomechanical causes, lifestyle, or by some other causes.
2. The angiogenesis as part of the observable manifestation of the disease or disorder. That is, the disease or disorder is measurable in terms of the increased or reduced angiogenesis. From a clinical standpoint, angiogenesis indicates the disease; however, angiogenesis need not be the "hallmark" of the disease or disorder.
3. The angiogenesis is part of the biochemical or cellular cascade that results in the disease or disorder. In this respect, regulation of angiogenesis may interrupt the cascade, and may control the disease. Non-limiting examples of angiogenesis regulated disorders that may be treated by the present disclosure are herein described below.

Formulations

The present disclosure also relates to compositions or formulations which comprise the Kv1.5 potassium channel inhibitors according to the present disclosure. In general, the compositions of the present disclosure comprise:
  a) an effective amount of one or more phenylsufamic acids and salts thereof according to the present disclosure which are effective as human protein tyrosine phosphatase beta (HPTP-β) inhibitors; and
  b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:
  a) from about 0.001 mg to about 1000 mg of one or more phenylsulfamic acids according to the present disclosure; and
  b) one or more excipients.

Another embodiment according to the present disclosure relates to the following compositions:
  a) from about 0.01 mg to about 100 mg of one or more phenylsulfamic acids according to the present disclosure; and
  b) one or more excipients.

A further embodiment according to the present disclosure relates to the following compositions:
  a) from about 0.1 mg to about 10 mg of one or more phenylsulfamic acids according to the present disclosure; and
  b) one or more excipients.

The term "effective amount" as used herein means "an amount of one or more phenylsulfamic acids, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. Thus, it is not possible to specify an exact "effective amount." For example, several divided doses may be administered daily or the dose may be proportionally reduced as indicated by the exigencies of the therapeutic situation. In addition, the compositions of the present disclosure can be administered as frequently as necessary to achieve a therapeutic amount.

Method of Use

The present disclosure relates to methods for regulating angiogenesis in a human comprising administering to a human one or more of the disclosed compounds.

One example of the disclosed methods includes a method for treating an angiogenesis regulated disorder in a subject, wherein the angiogenesis regulated disorder is an angiogenesis elevated disorder, and said disorder is chosen from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy.

Another example of the disclosed methods includes a method for treating an angiogenesis regulated disorder in a subject, wherein the angiogenesis regulated disorder is an angiogenesis elevated disorder, and said disorder is chosen from inflammatory bowel diseases such as Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

A further example of the disclosed methods includes a method for treating an angiogenesis regulated disorder in a subject wherein the angiogenesis regulated disorder is an angiogenesis reduced disorder and chosen from skeletal muscle and myocardial ischemia, stroke, coronary artery disease, peripheral vascular disease, coronary artery disease.

A yet further example of the disclosed methods includes a method of vascularizing ischemic tissue. As used herein, "ischemic tissue," means tissue that is deprived of adequate blood flow. Examples of ischemic tissue include, but are not limited to, tissue that lack adequate blood supply resulting from myocardial and cerebral infarctions, mesenteric or limb ischemia, or the result of a vascular occlusion or stenosis. In one example, the interruption of the supply of oxygenated blood may be caused by a vascular occlusion. Such vascular occlusion may be caused by arteriosclerosis, trauma, surgical procedures, disease, and/or other etiologies. Also included within the methods of treatment of the present disclosure is the treatment of skeletal muscle and myocardial ischemia, stroke, coronary artery disease, peripheral vascular disease, coronary artery disease.

A still further example of the disclosed methods includes a method of repairing tissue. As used herein, "repairing tissue" means promoting tissue repair, regeneration, growth, and/or maintenance including, but not limited to, wound repair or tissue engineering. One skilled in the art appreciates that new blood vessel formation is required for tissue repair. In turn, tissue may be damaged by, including, but not limited to, traumatic injuries or conditions including arthritis, osteoporosis and other skeletal disorders, and burns. Tissue may also be damaged by injuries due to surgical procedures, irradiation, laceration, toxic chemicals, viral infection or bacterial infections, or burns. Tissue in need of repair also includes non-healing wounds. Examples of non-healing wounds include non-healing skin ulcers resulting from diabetic pathology; or fractures that do not heal readily.

The disclosed compounds are also suitable for use in effecting tissue repair in the context of guided tissue regeneration (GTR) procedures. Such procedures are currently used by those skilled in the arts to accelerate wound healing following invasive surgical procedures.

A yet still further example of the disclosed methods includes a method of promoting tissue repair characterized by enhanced tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present methods may be used to augment the design and growth of human tissues outside the body for later implantation in the repair or replacement of diseased tissues. For example, antibodies may be useful in promoting the growth of skin graft replacements that are used as a therapy in the treatment of burns.

Other examples of the tissue engineering example of the disclosed methods includes in cell-containing or cell-free devices that induce the regeneration of functional human tissues when implanted at a site that requires regeneration. As discussed herein, biomaterial-guided tissue regeneration may be used to promote bone re-growth in, for example, periodontal disease. Thus, antibodies may be used to promote the growth of reconstituted tissues assembled into three-dimensional configurations at the site of a wound or other tissue in need of such repair.

A yet further example of the tissue engineering example of the disclosed methods, the compounds disclosed herein can be included in external or internal devices containing human tissues designed to replace the function of diseased internal tissues. This approach involves isolating cells from the body, placing them with structural matrices, and implanting the new system inside the body or using the system outside the body. For example, antibodies may be included in a cell-lined vascular graft to promote the growth of the cells contained in the graft. It is envisioned that the methods of the disclosure may be used to augment tissue repair, regeneration and engineering in products such as cartilage and bone, central nervous system tissues, muscle, liver, and pancreatic islet (insulin-producing) cells.

The present disclosure also relates to the use of the disclosed phenylsulfamic acids in the manufacture of a medicament for promoting the growth of skin graft replacements.

The present disclosure also relates to the use of the disclosed phenylsulfamic acids according to the present disclosure in the manufacture of a medicament for use in effecting tissue repair in the context of guided tissue regeneration (GTR) procedures.

The disclosed compounds can be used in the manufacture of one or more medicaments, non-limiting examples of these medicaments are:

Medicaments for the treatment an angiogenesis regulated disorder in a subject, wherein the angiogenesis regulated disorder is an angiogenesis elevated disorder.

Medicaments for the treatment an angiogenesis regulated disorder in a subject, wherein the angiogenesis regulated disorder is an angiogenesis elevated disorder chosen from Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

Medicaments useful for the purposes of tissue engineering thereby inducing enhanced tissue growth.

Medicaments for the treatment an angiogenesis regulated disorder in a subject, wherein the angiogenesis regulated disorder is an angiogenesis reduced disorder.

Procedures

Screening Assays Using In Vitro and In Vivo Models of Angiogenesis

Antibodies of the disclosure may be screened in angiogenesis assays that are known in the art. Such assays include in vitro assays that measure surrogates of blood vessel growth in cultured cells or formation of vascular structures from tissue explants and in vivo assays that measure blood vessel growth directly or indirectly (Auerbach, R., et al. (2003). Clin Chem 49, 32-40, Vailhe, B., et al. (2001). Lab Invest 81, 439-452).

1. In Vitro Models of Angiogenesis

The in vitro models which are suitable for use in the present disclosure employ cultured endothelial cells or tissue explants and measure the effect of agents on "angiogenic" cell responses or on the formation of blood capillary-like structures. Non-limiting examples of in vitro angiogenesis assays include but are not limited to endothelial cell migration and proliferation, capillary tube formation, endothelial sprouting, the aortic ring explant assay and the chick aortic arch assay.

2. In Vivo Models of Angiogenesis

The in vivo agents or antibodies which are suitable for use in the present disclosure are administered locally or systemically in the presence or absence of growth factors (i.e. VEGF or angiopoietin 1) and new blood vessel growth is measured by direct observation or by measuring a surrogate marker such as hemoglobin content or a fluorescent indicator. Non-limiting examples of in vitro angiogenesis assays include but are not limited to chick chorioallantoic membrane assay, the corneal angiogenesis assay, and the Matrigel® plug assay.

3. Procedures for Determining Vascularization of Ischemic Tissue.

Standard routine techniques are available to determine if a tissue is at risk of suffering ischemic damage from undesirable vascular occlusion. For example, in myocardial disease these methods include a variety of imaging techniques (e.g., radiotracer methodologies, x-ray, and MRI) and physiological tests. Therefore, induction of angiogenesis as an effective means of preventing or attenuating ischemia in tissues affected by or at risk of being affected by a vascular occlusion can be readily determined.

A person skilled in the art of using standard techniques may measure the vascularization of tissue. Non-limiting examples of measuring vascularization in a subject include SPECT (single photon emission computed tomography); PET (positron emission tomography); MRI (magnetic resonance imaging); and combination thereof, by measuring blood flow to tissue before and after treatment. Angiography may be used as an assessment of macroscopic vascularity. Histologic evaluation may be used to quantify vascularity at the small vessel level. These and other techniques are discussed in Simons, et al., "Clinical trials in coronary angiogenesis," *Circulation,* 102, 73-86 (2000).

The following are non-limiting examples of HPTPβ ($IC_{50}$ μM) and PTP1B ($IC_{50}$ μM) activity is listed herein below in Table VIII.

TABLE VIII

| No. | Compound | HPTPβ $IC_{50}$ μM | PTP1B $IC_{50}$ μM |
|---|---|---|---|
| A1 | 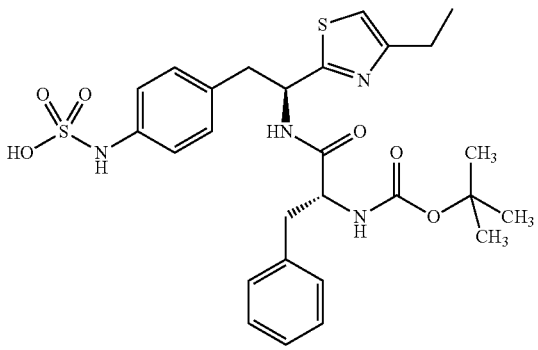 [SMILES: CCc1csc([C@H](Cc2ccc(NS(=O)(=O)O)cc2)NC(=O)[C@@H](Cc2ccccc2)NC(=O)OC(C)(C)C)n1] 4-{(S)-2-[(R)-2-(tert-butoxycarbonyl)-3-phenylpropanamido]-2-(4-ethylthiazol-2-yl)ethyl}phenylsulfamic acid | 0.004 | 7.12 |
| A2 | 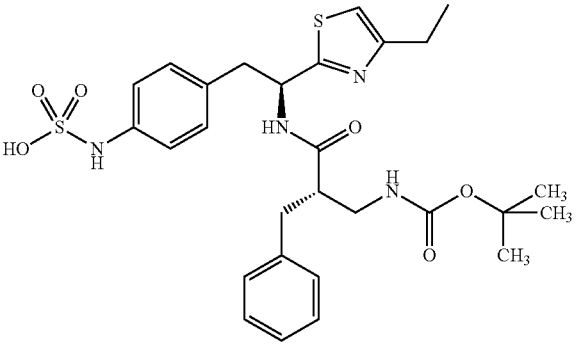 [SMILES: CCc1csc([C@H](Cc2ccc(NS(=O)(=O)O)cc2)NC(=O)[C@H](CNC(=O)OC(C)(C)C)Cc2ccccc2)n1] {1-[1-(5-Ethylthiazol-2-yl)-(S)-2-(4-sulfoaminophenyl)ethyl-carbamoyl]-(S)-2-phenylethyl}methyl carbamic acid tert-butyl ester | 0.031 | 7.05 |
| A3 | 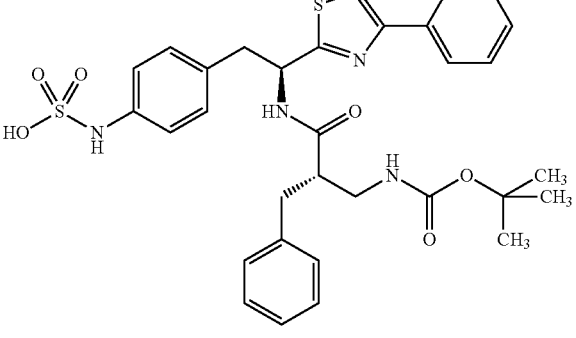 {1-[1-(5-phenylthiazol-2-yl)-(S)-2-(4-sulfoaminophenyl)ethylcarbamoyl]-(S)-2-phenylethyl}methyl carbamic acid tert-butyl ester | <5 × $10^{-8}$ | 0.754 |

TABLE VIII-continued
| No. | Compound | HPTPβ IC$_{50}$ μM | PTP1B IC$_{50}$ μM |
|---|---|---|---|
| A4 | 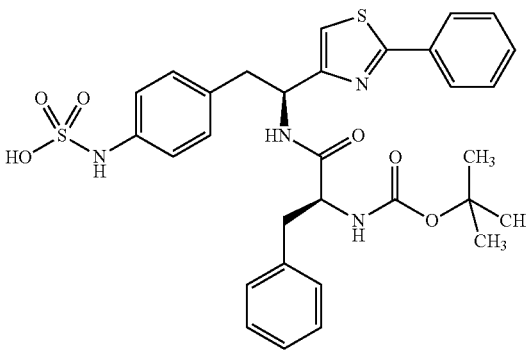<br>4-{(S)-2-(S)-2-(tert-Butoxycarbonylamino)-3-phenylpropanamido-2-(2-phenylthiazol-4-yl)}phenylsulfamic acid | <5 × 10$^{-8}$ | 0.905 |
| A5 | 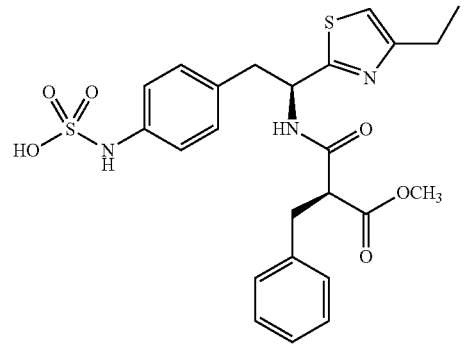 [SMILES: CCc1csc([C@H](Cc2ccc(NS(=O)(=O)O)cc2)NC(=O)[C@H](Cc2ccccc2)C(=O)OC)n1]<br>4-{(S)-2-(4-Ethylthiazol-2-yl)-2-[(S)-2-(methoxycarbonyl)-3-phenylpropanamido]ethyl}phenylsulfamic acid | 0.000162 | 0.49 |
| A6 | 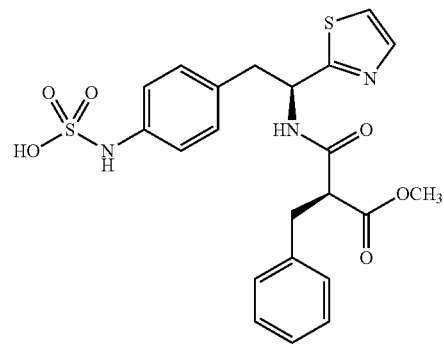 [SMILES: COC(=O)[C@@H](Cc1ccccc1)C(=O)N[C@@H](Cc1ccc(NS(=O)(=O)O)cc1)c1nccs1]<br>4-{(S)-2-[(S)-2-(Methoxycarbonyl)-3-phenylpropanamido]-2-(thiazol-2-yl)ethyl}phenylsulfamic acid | 0.006 | 1.02 |

TABLE VIII-continued
| No. | Compound | HPTPβ IC$_{50}$ μM | PTP1B IC$_{50}$ μM |
|---|---|---|---|
| A7 | 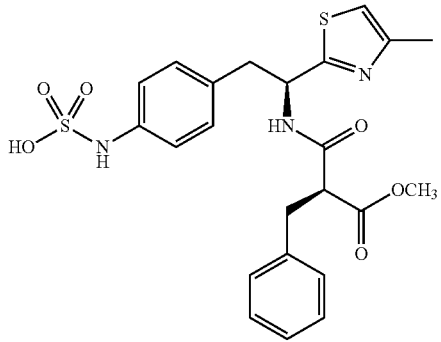 [SMILES: COC(=O)[C@@H](Cc1ccccc1)C(=O)N[C@@H](Cc1ccc(NS(=O)(=O)O)cc1)c1nc(C)cs1]<br>4-{(S)-2-[(S)-2-(Methoxycarbonyl)-3-phenylpropanamido]-2-(4-methylthiazol-2-yl)ethyl}phenylsulfamic acid | 0.001 | 0.48 |
| A8 | 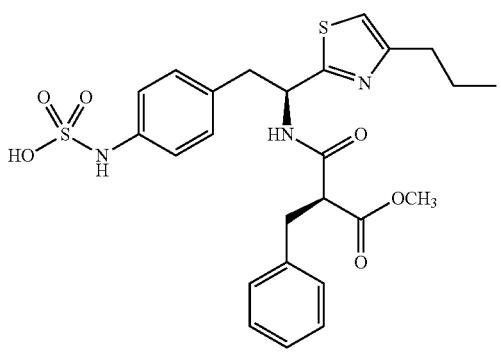 [SMILES: CCCc1csc([C@H](Cc2ccc(NS(=O)(=O)O)cc2)NC(=O)[C@H](Cc2ccccc2)C(=O)OC)n1]<br>4-{(S)-2-[(S)-2-(Methoxycarbonyl)-3-phenylpropanamido]-2-(4-propylthiazol-2-yl)ethyl}phenylsulfamic acid | 0.0001 | 1.03 |
| A9 | 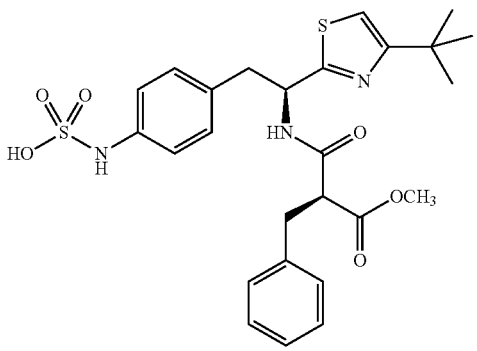 [SMILES: COC(=O)[C@@H](Cc1ccccc1)C(=O)N[C@@H](Cc1ccc(NS(=O)(=O)O)cc1)c1nc(C(C)(C)C)cs1]<br>4-{(S)-2-(4-tert-Butylthiazol-2-yl)-2-[(S)-2-(methoxycarbonyl)-3-phenylpropanamido]ethyl}phenylsulfamic acid | 0.0002 | 0.708 |

TABLE VIII-continued
| No. | Compound | HPTPβ IC$_{50}$ μM | PTP1B IC$_{50}$ μM |
|---|---|---|---|
| A10 | 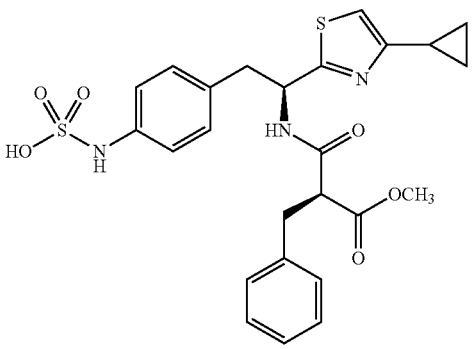 [SMILES: COC(=O)[C@@H](Cc1ccccc1)C(=O)N[C@@H](Cc1ccc(NS(=O)(=O)O)cc1)c1nc(C2CC2)cs1]<br>4-{(S)-2-(4-Cyclopropylthiazol-2-yl)-2-[(S)-2-(methoxy-carbonyl)-3-phenylpropanamido]ethyl}phenylsulfamic acid | 0.00001 | 0.3 |
| A11 | 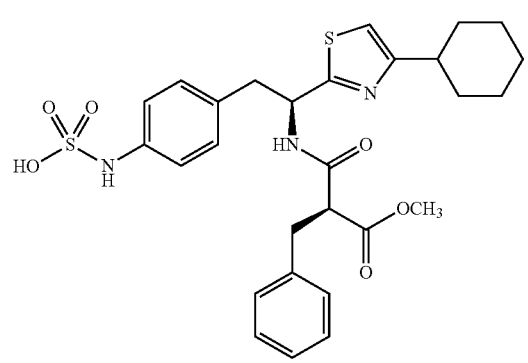 [SMILES: COC(=O)[C@@H](Cc1ccccc1)C(=O)N[C@@H](Cc1ccc(NS(=O)(=O)O)cc1)c1nc(C2CCCCC2)cs1]<br>4-{(S)-2-(4-Cyclohexylthiazol-2-yl)-2-[(S)-2-(methoxycarbonyl)-3-phenyl-propanamido]ethyl}phenylsulfamic acid | <5 × 10$^{-8}$ | 1.78 |
| A12 | 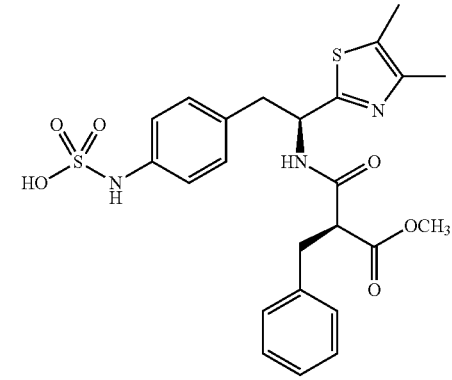 [SMILES: COC(=O)[C@@H](Cc1ccccc1)C(=O)N[C@@H](Cc1ccc(NS(=O)(=O)O)cc1)c1nc(C)c(C)s1]<br>4-{(S)-2-(4,5-Dimethylthiazol-2-yl)-2-[(S)-2-(methoxycarbonyl)-3-phenyl-propanamido]ethyl}phenylsulfamic acid | 0.001 | 0.31 |

TABLE VIII-continued
| No. | Compound | HPTPβ IC$_{50}$ μM | PTP1B IC$_{50}$ μM |
|---|---|---|---|
| A13 | 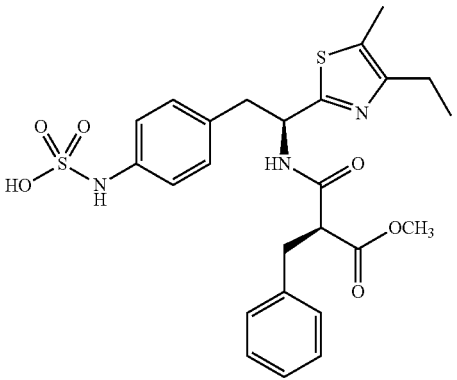 [SMILES: CCc1nc([C@H](Cc2ccc(NS(=O)(=O)O)cc2)NC(=O)[C@H](Cc2ccccc2)C(=O)OC)sc1C] 4-{(S)-2-(4-Ethyl-5-methylthiazol-2-yl)-2-[(S)-2-(methoxy-carbonyl)-3-phenyl-propanamido]ethyl}phenylsulfamic acid | 0.0001 | 1.12 |
| A14 | 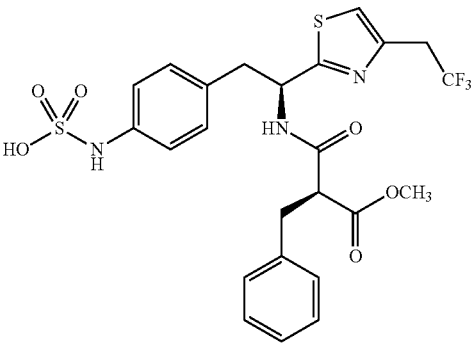 [SMILES: COC(=O)[C@@H](Cc1ccccc1)C(=O)N[C@@H](Cc1ccc(NS(=O)(=O)O)cc1)c1nc(CC(F)(F)F)cs1] 4-{(S)-2-[(S)-2-(Methoxycarbonyl)-3-phenylpropanamido]-2-[4-(2,2,2-trifluoroethyl)thiazol-2-yl]ethyl}phenylsulfamic acid | 0.0003 | 1.63 |
| A15 | 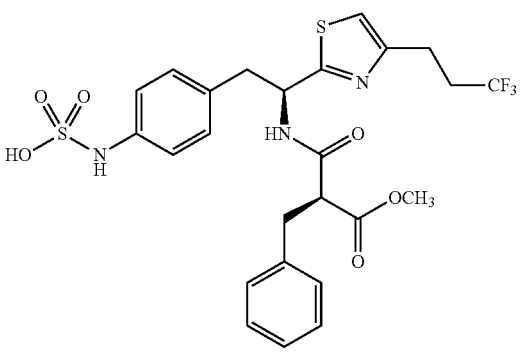 [SMILES: COC(=O)[C@@H](Cc1ccccc1)C(=O)N[C@@H](Cc1ccc(NS(=O)(=O)O)cc1)c1nc(CCC(F)(F)F)cs1] 4-{(S)-2-[(S)-2-(Methoxycarbonyl)-3-phenylpropanamido)-2-[4-(3,3,3-trifluoropropyl)thiazol-2-yl]ethyl}phenylsulfamic acid | 0.00008 | 0.12 |

TABLE VIII-continued
| No. | Compound | HPTPβ IC$_{50}$ μM | PTP1B IC$_{50}$ μM |
|---|---|---|---|
| A16 | 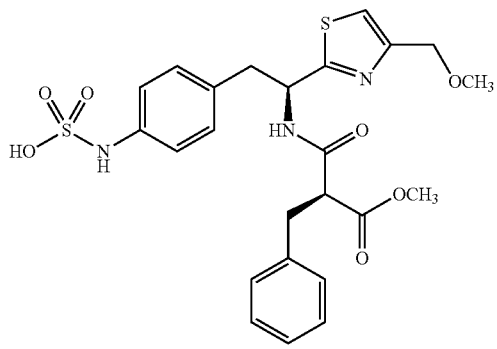 [SMILES: COCc1csc([C@H](Cc2ccc(NS(=O)(=O)O)cc2)NC(=O)[C@H](Cc2ccccc2)C(=O)OC)n1]<br>4-{(S)-2-[(S)-2-(Methoxycarbonyl)-3-phenylpropanamido]-2-[4-(methoxymethyl)thiazol-2-yl]ethyl}phenylsulfamic acid | 0.001 | 0.64 |
| A17 | 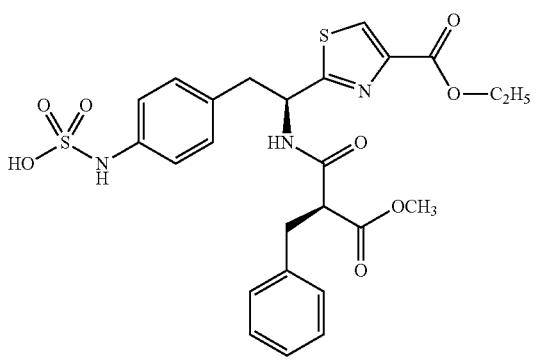 [SMILES: CCOC(=O)c1csc([C@H](Cc2ccc(NS(=O)(=O)O)cc2)NC(=O)[C@H](Cc2ccccc2)C(=O)OC)n1]<br>4-{(S)-2-(4-(Ethoxycarbonyl)thiazol-2-yl)-2-[(S)-2-(methoxy-carbonyl)-3-phenylpropanamido]ethyl}phenylsulfamic acid | 0.0002 | 0.07 |
| A18 | 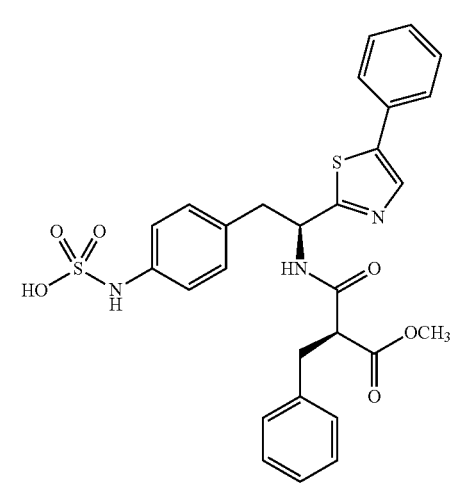 [SMILES: COC(=O)[C@@H](Cc1ccccc1)C(=O)N[C@@H](Cc1ccc(NS(=O)(=O)O)cc1)c1ncc(-c2ccccc2)s1]<br>4-{(S)-2-[(S)-2-(Methoxycarbonyl)-3-phenylpropanamido]-2-(5-phenylthiazol-2-yl)ethyl}phenylsulfamic acid | 0.0003 | 0.81 |

TABLE VIII-continued
| No. | Compound | HPTPβ IC$_{50}$ μM | PTP1B IC$_{50}$ μM |
|---|---|---|---|
| A19 | 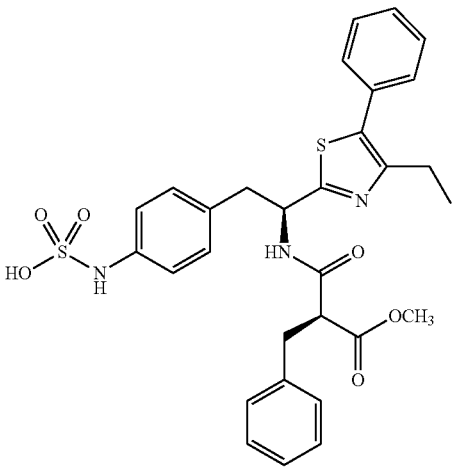 [SMILES: CCc1nc([C@H](Cc2ccc(NS(=O)(=O)O)cc2)NC(=O)[C@H](Cc2ccccc2)C(=O)OC)sc1-c1ccccc1] 4-{(S)-2-(4-Ethyl-5-phenylthiazol-2-yl)-2-[(S)-2-(methoxy-carbonyl)-3-phenyl-propanamido]ethyl}phenylsulfamic acid | <5 × 10$^{-8}$ | 0.39 |
| A20 | 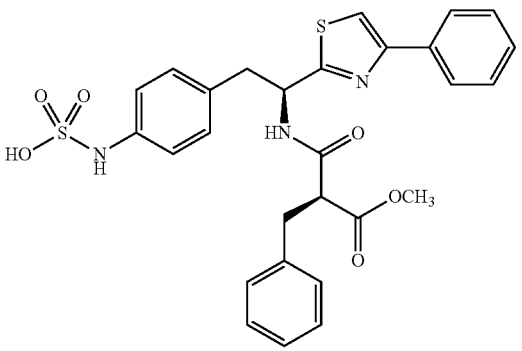 [SMILES: COC(=O)[C@@H](Cc1ccccc1)C(=O)N[C@@H](Cc1ccc(NS(=O)(=O)O)cc1)c1nc(-c2ccccc2)cs1] 4-{(S)-2-[(S)-2-(Methoxycarbonyl)-3-phenylpropanamido]-2-(4-phenylthiazol-2-yl)ethyl}phenylsulfamic acid | <2 × 10$^{-6}$ | 0.597 |
| A21 | 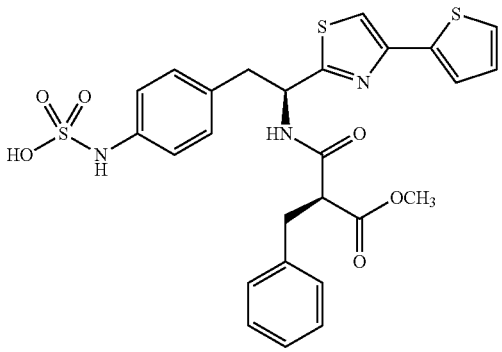 [SMILES: COC(=O)[C@@H](Cc1ccccc1)C(=O)N[C@@H](Cc1ccc(NS(=O)(=O)O)cc1)c1nc(-c2cccs2)cs1] 4-{(S)-2-[(S)-2-(Methoxycarbonyl)-3-phenylpropanamido]-2-[4-(thiophen-2-yl)thiazol-2-yl]ethyl}phenylsulfamic acid | <5 × 10$^{-8}$ | 0.99 |

TABLE VIII-continued

| No. | Compound | HPTPβ IC$_{50}$ μM | PTP1B IC$_{50}$ μM |
|---|---|---|---|
| A22 | 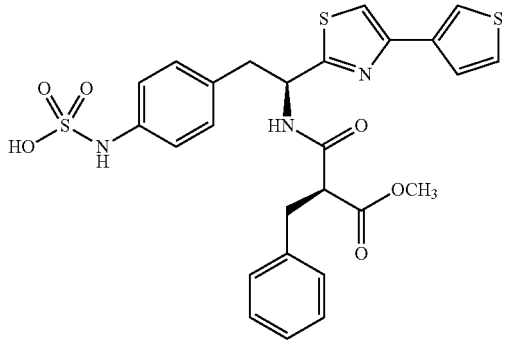 [SMILES: COC(=O)[C@@H](Cc1ccccc1)C(=O)N[C@@H](Cc1ccc(NS(=O)(=O)O)cc1)c1nc(-c2ccsc2)cs1]<br>4-{(S)-2-[(S)-2-(Methoxycarbonyl)-3-phenylpropanamido]-2-[4-(thiophen-3-yl)thiazol-2-yl]ethyl}phenylsulfamic acid | 0.00009 | 0.44 |
| A23 | 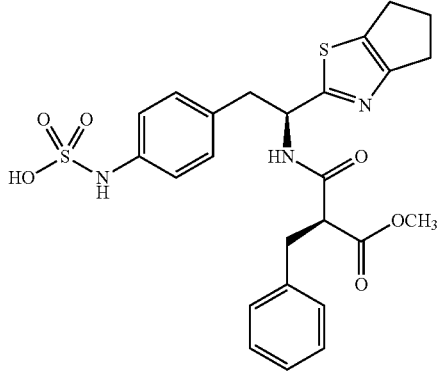 [SMILES: COC(=O)[C@@H](Cc1ccccc1)C(=O)N[C@@H](Cc1ccc(NS(=O)(=O)O)cc1)c1nc2c(s1)CCC2]<br>4-{(S)-2-(5,6-Dihydro-4H-cyclopenta[d]thiazol-2-yl)-2-[(S)-2-(methoxy-carbonyl)-3-phenylpropanamido]ethyl}phenylsulfamic acid | 0.001 | 0.18 |
| A24 | 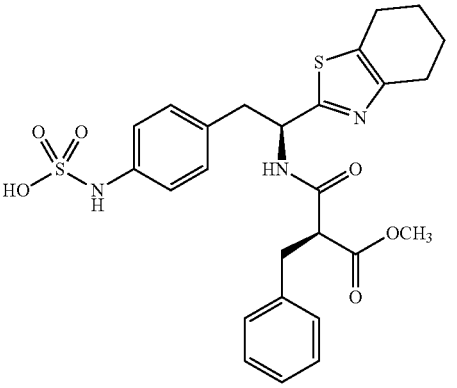 [SMILES: COC(=O)[C@@H](Cc1ccccc1)C(=O)N[C@@H](Cc1ccc(NS(=O)(=O)O)cc1)c1nc2c(s1)CCCC2]<br>4-{(S)-2-[(S)-2-(Methoxycarbonyl)-3-phenylpropanamido]-2-(4,5,6,7-tetrahydrobenzo[d]thiazol-2-yl)ethyl}phenylsulfamic acid | 0.0004 | 0.089 |

TABLE VIII-continued
| No. | Compound | HPTPβ IC$_{50}$ μM | PTP1B IC$_{50}$ μM |
|-----|----------|--------------------|--------------------|
| A25 | 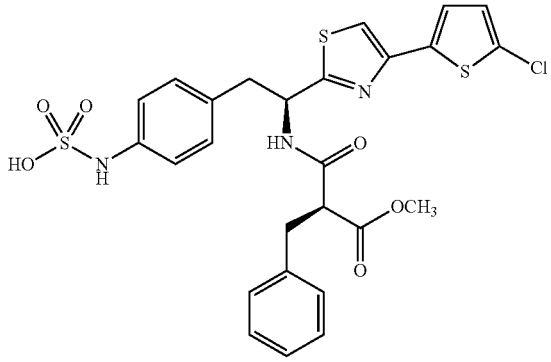 [SMILES: COC(=O)[C@@H](Cc1ccccc1)C(=O)N[C@@H](Cc1ccc(NS(=O)(=O)O)cc1)c1nc(-c2ccc(Cl)s2)cs1]<br>4-{(S)-2-[4-(5-Chlorothiophen-2-yl)thiazol-2-yl]-2-[(S)-2-(methoxycarbonyl)-3-phenylpropanamido]ethyl}phenyl-sulfamic acid | $<5 \times 10^{-8}$ | 0.37 |
| A26 | 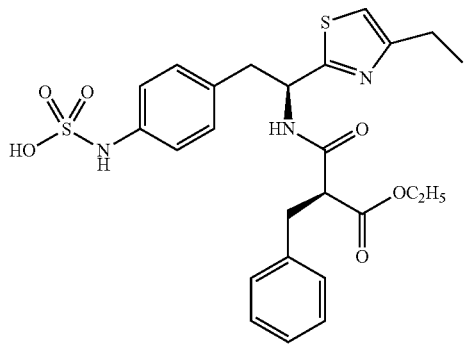 [SMILES: CCOC(=O)[C@@H](Cc1ccccc1)C(=O)N[C@@H](Cc1ccc(NS(=O)(=O)O)cc1)c1nc(CC)cs1]<br>4-{(S)-2-[(S)-2-(Ethoxycarbonyl)-3-phenylpropanamido]-2-(4-ethylthiazol-2-yl)ethyl}phenylsulfamic acid | 0.00014 | 0.68 |
| A27 | 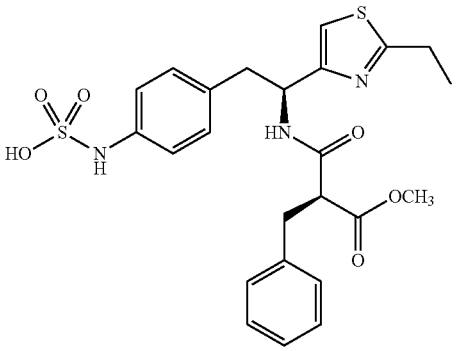 [SMILES: CCc1nc([C@H](Cc2ccc(NS(=O)(=O)O)cc2)NC(=O)[C@H](Cc2ccccc2)C(=O)OC)cs1]<br>4-{(S)-2-[(S)-2-(Methoxycarbonyl)-3-phenylpropanamido]-2-(2-ethylthiazol-4-yl)ethyl}phenylsulfamic acid | 0.0001 | 1.01 |

TABLE VIII-continued

| No. | Compound | HPTPβ IC$_{50}$ μM | PTP1B IC$_{50}$ μM |
|-----|----------|-----|-----|
| A28 | 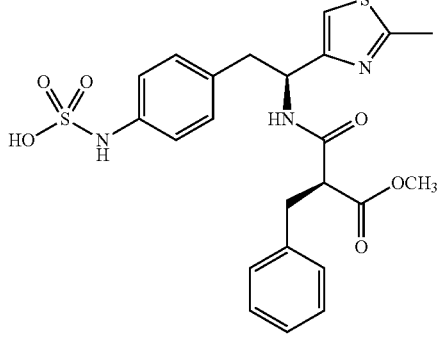<br>4-{(S)-2-[(S)-2-(Methoxycarbonyl)-3-phenylpropanamido]-2-(2-methylthiazol-4-yl)ethyl}phenylsulfamic acid | 0.001 | 1.16 |
| A29 | 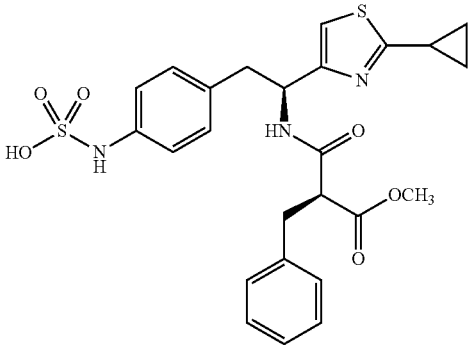 [SMILES: COC(=O)[C@@H](Cc1ccccc1)C(=O)N[C@@H](Cc1ccc(NS(=O)(=O)O)cc1)c1csc(C2CC2)n1]<br>4-{(S)-2-(2-Cyclopropylthiazol-4-yl)-2-[(S)-2-(methoxy-carbonyl)-3-phenylpropanamido]ethyl}phenylsulfamic acid | 0.0002 | 1.35 |
| A30 | 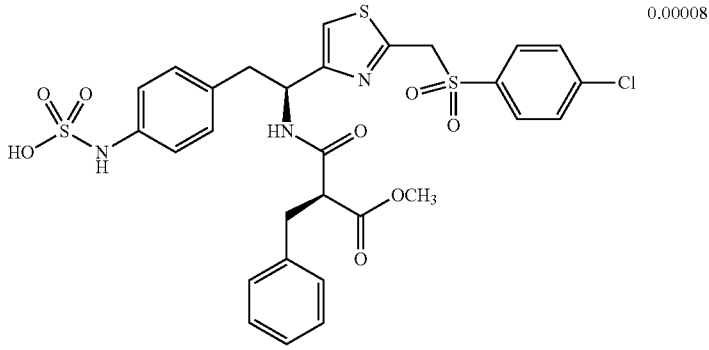<br>4-{(S)-2-{2-[(4-Chlorophenylsulfonyl)methyl]thiazol-4-yl}-2-[(S)-2-(methoxy-carbonyl)-3-phenylpropanamido]ethyl}phenylsulfamic acid | 0.00008 | 2.54 |

TABLE VIII-continued

| No. | Compound | HPTPβ IC$_{50}$ μM | PTP1B IC$_{50}$ μM |
|---|---|---|---|
| A31 | 4-{(S)-2-[2-(tert-Butylsulfonylmethyl)thiazol-4-yl]-2-[(S)-2-(methoxycarbonyl)-3-phenylpropanamido]ethyl}phenylsulfamic acid | 0.002 | 1.21 |
| A32 | 4-{(S)-2-[(S)-2-(Methoxycarbonyl)-3-phenylpropionamido]-2-(2-phenylthiazole-4-yl)ethyl}phenylsulfamic acid | $7 \times 10^{-7}$ | 0.508 |
| A33 | 4-{(S)-2-[(S)-2-(Methoxycarbonyl)-3-phenylpropanamido]-2-[2-(thiophen-2-yl)thiazol-4-yl]ethyl}phenylsulfamic acid | $5 \times 10^{-8}$ | 0.604 |

TABLE VIII-continued

| No. | Compound | HPTPβ IC$_{50}$ μM | PTP1B IC$_{50}$ μM |
|---|---|---|---|
| A34 | 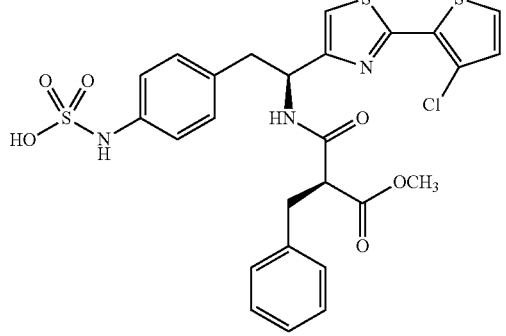<br>4-{(S)-2-[2-(3-Chlorothiophen-2-yl)thiazol-4-yl]-2-[(S)-2-(methoxycarbonyl)-3-phenylpropanamido]ethyl}phenylsulfamic acid | <5 × 10$^{-8}$ | 0.95 |
| A35 | 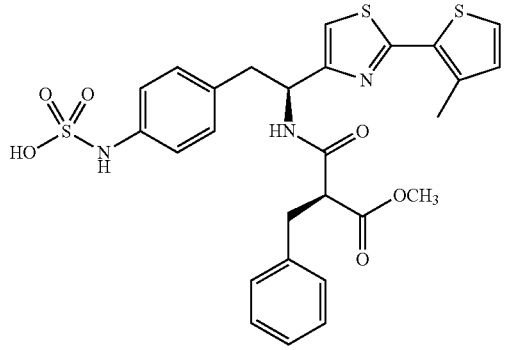 [SMILES: COC(=O)[C@@H](Cc1ccccc1)C(=O)N[C@@H](Cc1ccc(NS(=O)(=O)O)cc1)c1csc(-c2sccc2C)n1]<br>4-{(S)-2-[(S)-2-(Methoxycarbonyl)-3-phenylpropanamido]-2-[2-(3-methylthiophen-2-yl)thiazol-4-yl]ethyl}phenylsulfamic acid | <5 × 10$^{-8}$ | 1.09 |
| A36 | 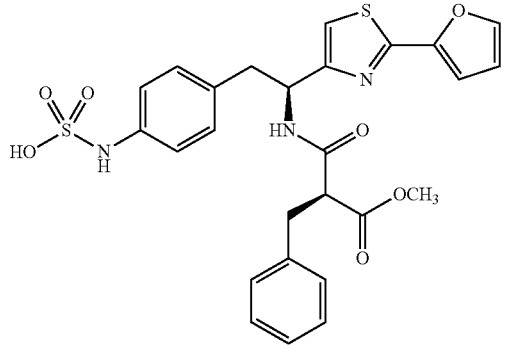 [SMILES: COC(=O)[C@@H](Cc1ccccc1)C(=O)N[C@@H](Cc1ccc(NS(=O)(=O)O)cc1)c1csc(-c2ccco2)n1]<br>4-{[(S)-2-(2-(Furan-2-yl)thiazol-4-yl]-2-[(S)-2-(methoxy-carbonyl)-3-phenylpropanamido]ethyl}phenylsulfamic acid | 0.0004 | 5 |

TABLE VIII-continued
| No. | Compound | HPTPβ IC$_{50}$ μM | PTP1B IC$_{50}$ μM |
|---|---|---|---|
| A37 | 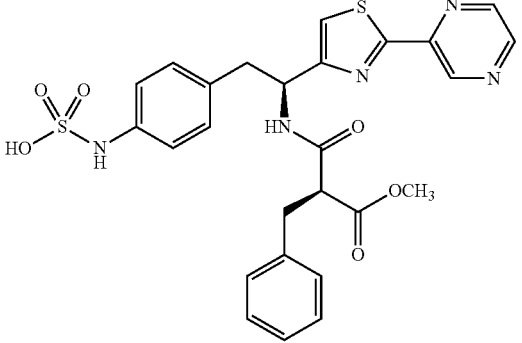<br>4-{(S)-2-[(S)-2-(Methoxycarbonyl)-3-phenylpropanamido]-2-[2-(pyrazin-2-yl)thiazol-4-yl]ethyl}phenylsulfamic acid | 0.003 | 0.295 |
| A38 | 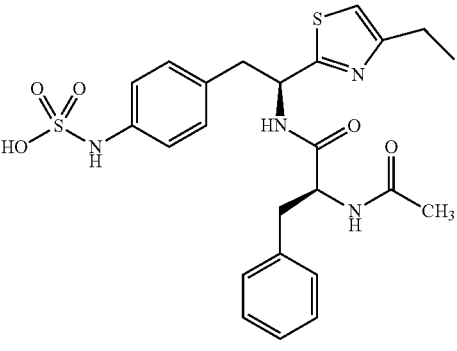 [SMILES: CCc1csc([C@H](Cc2ccc(NS(=O)(=O)O)cc2)NC(=O)[C@H](Cc2ccccc2)NC(C)=O)n1]<br>4-[(S)-2-((S)-2-Acetamido-3-phenylpropanamido)-2-(4-ethylthiazol-2-yl)ethyl]phenylsulfamic acid | 0.001 | 1.97 |
| A39 | 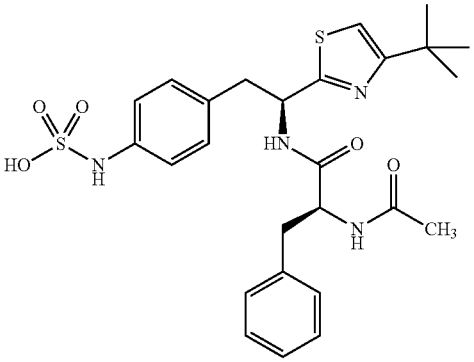 [SMILES: CC(=O)N[C@@H](Cc1ccccc1)C(=O)N[C@@H](Cc1ccc(NS(=O)(=O)O)cc1)c1nc(C(C)(C)C)cs1]<br>4-[(S)-2-((S)-2-Acetamido-3-phenylpropanamido)-2-(4-tert-butylthiazol-2-yl)ethyl]phenylsulfamic acid | 0.0003 | 1.52 |

TABLE VIII-continued

| No. | Compound | HPTPβ IC$_{50}$ μM | PTP1B IC$_{50}$ μM |
|---|---|---|---|
| A40 | 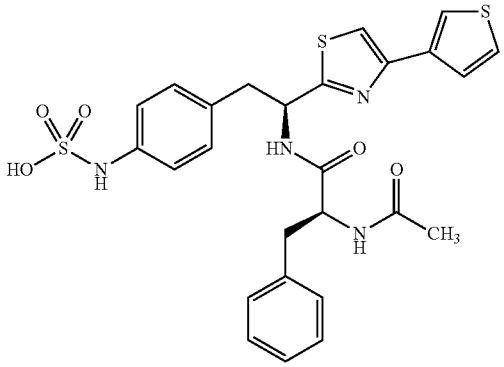 [SMILES: CC(=O)N[C@@H](Cc1ccccc1)C(=O)N[C@@H](Cc1ccc(NS(=O)(=O)O)cc1)c1nc(-c2ccsc2)cs1]<br>4-{(S)-2-((S)-2-Acetamido-3-phenylpropanamido)-2-[4-(thiophen-3-yl)thiazol-2-yl]ethyl}phenylsulfamic acid | 0.00024 | 1.16 |
| A41 | 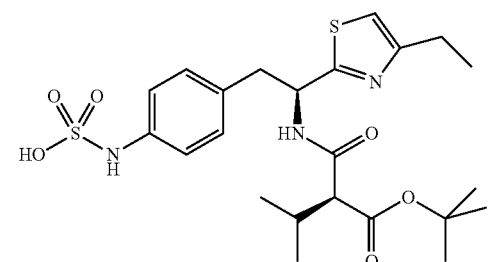<br>4-{(S)-2-[(S)-2-(tert-Butoxycarbonyl)-3-methylbutanamido]-2-(4-ethylthiazol-2-yl)ethyl}phenylsulfamic acid | 0.006 | 1.06 |
| A42 | 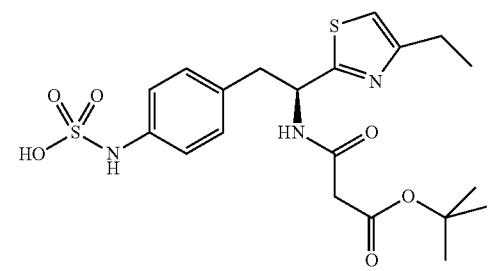 [SMILES: CCc1csc([C@H](Cc2ccc(NS(=O)(=O)O)cc2)NC(=O)CC(=O)OC(C)(C)C)n1]<br>(S)-4-{2-[2-(tert-Butoxycarbonyl)acetamido]-2-(4-ethylthiazol-2-yl)ethyl}phenylsulfamic acid | 0.028 | 16.0 |
| A43 | 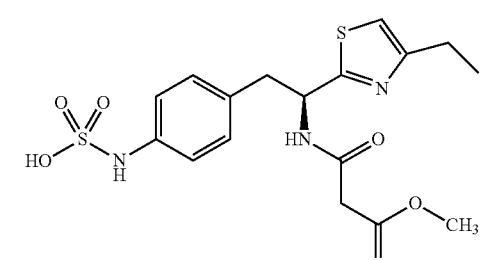<br>(S)-4-{2-(4-Ethylthiazol-2-yl)-2-[2-(methoxycarbonyl)acetamido]ethyl}phenylsulfamic acid | 0.020 | 5.26 |

TABLE VIII-continued

| No. | Compound | HPTPβ IC$_{50}$ μM | PTP1B IC$_{50}$ μM |
|---|---|---|---|
| A44 | 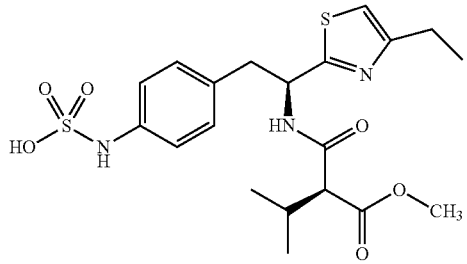 [SMILES: CCc1csc([C@H](Cc2ccc(NS(=O)(=O)O)cc2)NC(=O)[C@@H](C(=O)OC)C(C)C)n1]<br>4-{(S)-2-(4-Ethylthiazol-2-yl)-2-[(S)-2-(methoxycarbonyl)-3-methylbutanamido]-ethyl}phenylsulfamic acid | 0.003 | 1.03 |
| A45 | 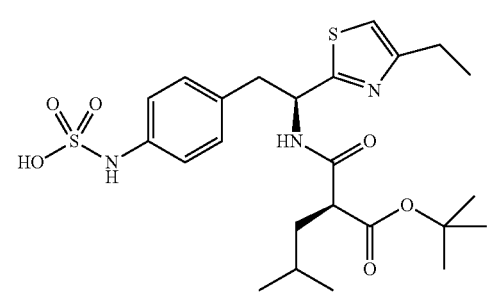 [SMILES: CCc1csc([C@H](Cc2ccc(NS(=O)(=O)O)cc2)NC(=O)[C@H](CC(C)C)C(=O)OC(C)(C)C)n1]<br>4-{(S)-2-[(S)-2-(tert-Butoxycarbonyl)-4-methylpentanamido]-2-(4-ethylthiazol-2-yl)ethyl}phenylsulfamic acid | 0.001 | 0.48 |
| A46 | 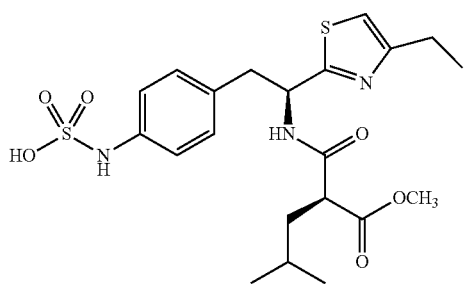 [SMILES: CCc1csc([C@H](Cc2ccc(NS(=O)(=O)O)cc2)NC(=O)[C@H](CC(C)C)C(=O)OC)n1]<br>4-{(S)-2-(4-Ethylthiazol-2-yl)-2-[(S)-2-(methoxycarbonyl)-4-methylpentanamido]ethyl}phenylsulfamic acid | 0.0003 | 0.07 |
| A47 | 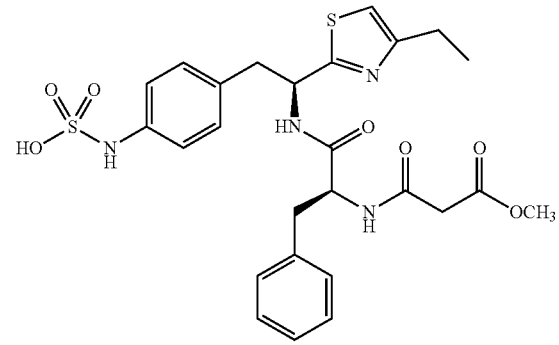 [SMILES: CCc1csc([C@H](Cc2ccc(NS(=O)(=O)O)cc2)NC(=O)[C@H](Cc2ccccc2)NC(=O)CC(=O)OC)n1]<br>4-((S)-2-(4-Ethylthiazol-2-yl)-2-{(S)-2-[2-(methoxycarbonyl)-acetamido]-3-phenylpropanamido}ethyl)phenylsulfamic acid | 0.0003 | 0.299 |

TABLE VIII-continued

| No. | Compound | HPTPβ IC$_{50}$ μM | PTP1B IC$_{50}$ μM |
|---|---|---|---|
| A48 | 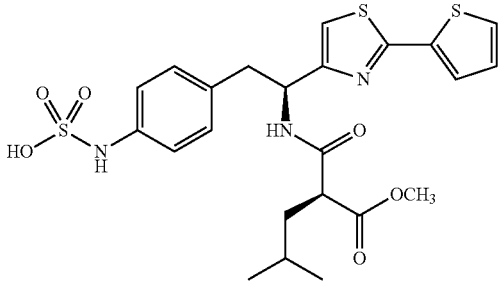 [SMILES: COC(=O)[C@@H](CC(C)C)C(=O)N[C@@H](Cc1ccc(NS(=O)(=O)O)cc1)c1csc(-c2cccs2)n1]<br>4-{(S)-2-[(S)-2-(Methoxycarbonyl)-4-methylpentanamido]-2-[2-(thiophen-2-yl)thiazol-4-yl]ethyl}phenylsulfamic acid | <5 × 10$^{-8}$ | 0.52 |
| A49 | 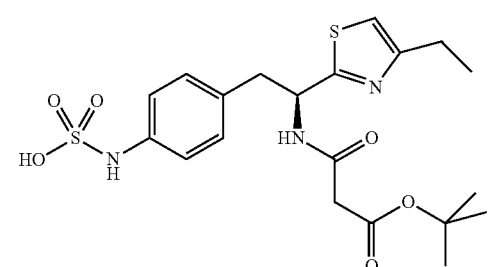<br>(S)-4-{2-[2-(tert-Butoxycarbonyl)acetamido]-2-(4-ethylthiazol-2-yl)ethyl}-phenylsulfamic acid | 0.028 | 16.0 |
| A50 | 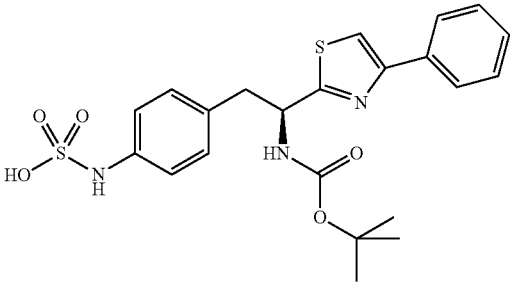 [SMILES: CC(C)(C)OC(=O)N[C@@H](Cc1ccc(NS(=O)(=O)O)cc1)c1nc(-c2ccccc2)cs1]<br>[1-(S)-(Phenylthiazol-2-yl)-2-(4-sulfoaminophenyl)ethyl]-carbamic acid tert-butyl ester | 0.049 | 33.02 |
| A51 | 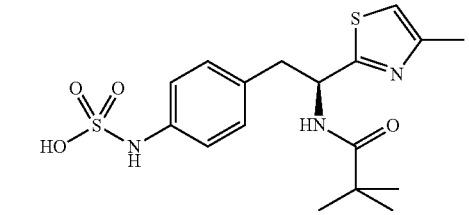 [SMILES: Cc1csc([C@H](Cc2ccc(NS(=O)(=O)O)cc2)NC(=O)C(C)(C)C)n1]<br>(S)-4-(2-(4-Methylthiazol-2-yl)-2-pivalamidoethyl)phenyl-sulfamic acid | 0.112 | 50 |

TABLE VIII-continued

| No. | Compound | HPTPβ IC$_{50}$ μM | PTP1B IC$_{50}$ μM |
|---|---|---|---|
| A52 | (S)-4-(2-(4-Ethylthiazol-2-yl)-2-pivalamidoethyl)phenyl-sulfamic acid | 0.085 | 142 |
| A53 | (S)-4-{2-[4-(hydroxymethyl)thiazol-2-yl]-2-pivalamidoethyl}phenyl-sulfamic acid | 0.266 | 50 |
| A54 | (S)-4-{[2-(4-Ethoxycarbonyl)thiazol-2-yl]-2-pivalamidoethyl}phenylsulfamic acid | 0.584 | 44.9 |
| A55 | (S)-4-(2-(4-Phenylthiazol-2-yl)-2-pivalamidoethyl)phenylsulfamic acid | 0.042 | 82.3 |
| A56 | 4-((S)-2-(4-(3-Methoxyphenyl)thiazol-2-yl)-2-pivalamidoethyl)phenylsulfamic acid | 0.110 | 40.1 |

TABLE VIII-continued

| No. | Compound | HPTPβ IC$_{50}$ μM | PTP1B IC$_{50}$ μM |
|---|---|---|---|
| A57 | 4-((S)-2-(4-(2,4-Dimethoxyphenyl)thiazol-2-yl)-2-pivalamidoethyl)phenyl-sulfamic acid | 0.086 | 43.1 |
| A58 | (S)-4-(2-(4-Benzylthiazol-2-yl)-2-pivalamidoethyl)phenylsulfamic acid | 0.113 | 38.2 |
| A59 | (S)-4-(2-(4-(3-Methoxybenzyl)thiazol-2-yl)-2-pivalamidoethyl)phenylsulfamic acid | 0.132 | 50 |
| A60 | 4-((S)-2-(4-(2,3-Dihydrobenzo[b][1,4]dioxin-6-yl)thiazol-2-yl)-2-pivalamidoethyl)phenylsulfamic acid | 0.138 | 38.3 |
| A61 | (S)-4-(2-(5-Methyl-4-phenylthiazol-2-yl)-2-pivalamidoethyl)phenylsulfamic acid | 0.098 | 50.5 |

TABLE VIII-continued

| No. | Compound | HPTPβ IC$_{50}$ μM | PTP1B IC$_{50}$ μM |
|---|---|---|---|
| A62 | 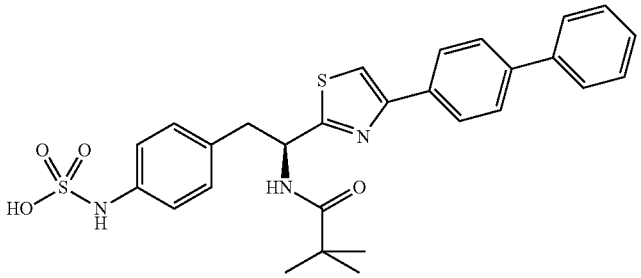 [SMILES: CC(C)(C)C(=O)N[C@@H](Cc1ccc(NS(=O)(=O)O)cc1)c1nc(-c2ccc(-c3ccccc3)cc2)cs1]<br>(S)-4-(2-(4-(Biphen-4-yl)thiazol-2-yl)-2-pivalamidoethyl)phenylsulfamic acid | 0.381 | 28.6 |
| A63 | 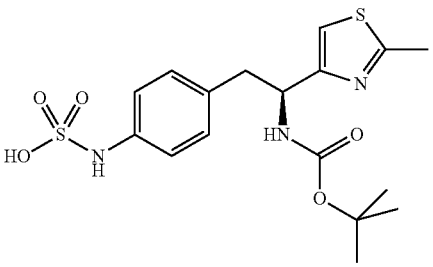 [SMILES: Cc1nc([C@H](Cc2ccc(NS(=O)(=O)O)cc2)NC(=O)OC(C)(C)C)cs1]<br>(S)-4-(2-tert-Butoxycarbonylamino)-2-(2-methylthiazol-4-yl)ethyl)phenylsulfamic acid | 0.033 | 18.9 |
| A64 | 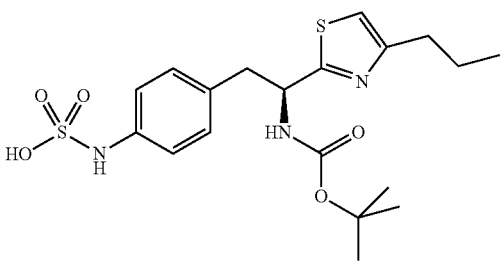 [SMILES: CCCc1csc([C@H](Cc2ccc(NS(=O)(=O)O)cc2)NC(=O)OC(C)(C)C)n1]<br>(S)-4-(2-(tert-Butoxycarbonylamino)-2-(4-propylthiazol-2-yl)ethyl)phenyl sulfamic acid | 0.04 | 35.6 |
| A65 | 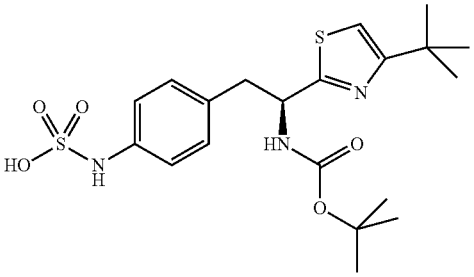 [SMILES: CC(C)(C)OC(=O)N[C@@H](Cc1ccc(NS(=O)(=O)O)cc1)c1nc(C(C)(C)C)cs1]<br>(S)-4-(2-(tert-Butoxycarbonylamino)-2-(4-tert-butylthiazol-2-yl)ethyl)phenyl sulfamic acid | 0.027 | 50 |

| No. | Compound | HPTPβ IC$_{50}$ μM | PTP1B IC$_{50}$ μM |
|---|---|---|---|
| A66 | 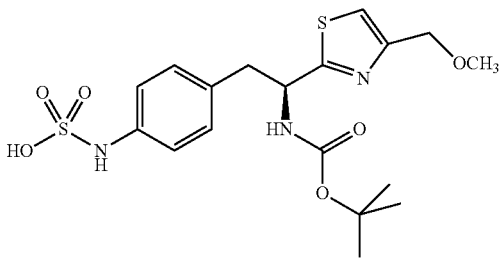 [SMILES: COCc1csc([C@H](Cc2ccc(NS(=O)(=O)O)cc2)NC(=O)OC(C)(C)C)n1]<br>(S)-4-(2-(tert-Butoxycarbonylamino)-2-(4-(methoxymethyl)thiazol-2-yl)ethyl)-phenyl sulfamic acid | 0.18 | 27.6 |
| A67 | 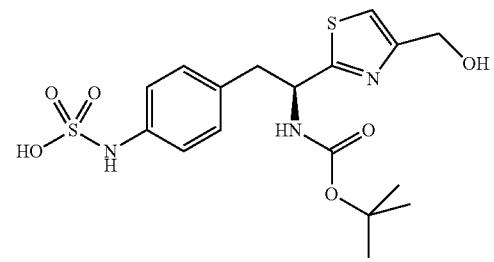 [SMILES: CC(C)(C)OC(=O)N[C@@H](Cc1ccc(NS(=O)(=O)O)cc1)c1nc(CO)cs1]<br>(S)-4-(2-(tert-Butoxycarbonylamino)-2-(4-(hydroxymethyl)thiazol-2-yl)ethyl)phenylsulfamic acid | 0.644 | 31.6 |
| A68 | 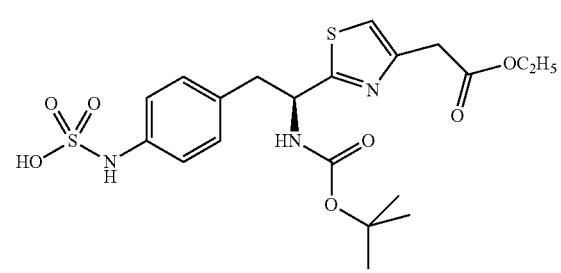 [SMILES: CCOC(=O)Cc1csc([C@H](Cc2ccc(NS(=O)(=O)O)cc2)NC(=O)OC(C)(C)C)n1]<br>(S)-4-(2-tert-Butoxycarbonylamino)-2-(4-(2-ethoxy-2-oxoethyl)thiazol-2-yl)ethyl)phenylsulfamic acid | 0.167 | 50 |
| A69 | 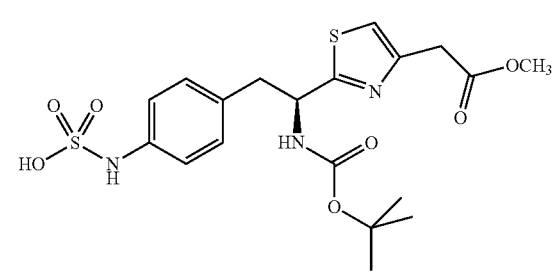 [SMILES: COC(=O)Cc1csc([C@H](Cc2ccc(NS(=O)(=O)O)cc2)NC(=O)OC(C)(C)C)n1]<br>(S)-4-(2-(tert-Butoxycarbonyl)-2-(4-(2-(2-methoxy-2-oxoyethyl amino)-2-oxoethyl)thiazole-2-yl)ethyl)phenylsulfamic acid | 0.132 | 50 |

TABLE VIII-continued

| No. | Compound | HPTPβ IC$_{50}$ μM | PTP1B IC$_{50}$ μM |
|---|---|---|---|
| A70 | (S)-4-(2-(tert-Butoxycarbonylamino)-2-(2-pivalamidothiazol-4-yl)ethyl)phenylsulfamic acid | 0.555 | 9.12 |
| A71 | (S)-4-(2-(tert-Butoxycarbonylamino)-2-(5-phenylthiazol-2-yl)ethyl)-phenyl sulfamic acid | 0.308 | 11.4 |
| A72 | 4-((S)-2-(tert-Butoxycarbonylamino)-2-(4-(3-(trifluoromethyl)phenyl)thiazol-2-yl)ethyl)-phenyl sulfamic acid | 0.253 | 11.8 |
| A73 | 4-((S)-2-(tert-Butoxycarbonylamino)-2-(4-(thiophen-3-yl)thiazol-2-yl)ethyl)phenyl sulfamic acid | 0.045 | 14.6 |

The Rat hindlimb model is used to evaluate angiogenic properties of novel HPTPβ inhibitors. Specifically to determine if there is enhanced blood flow to the collateral dependent region of the leg post ischemia when the animal is in an exercise challenged state. The specific compound accessed in this example is (4-{(S)-2-[(S)-2-(tert-Butoxycarbonylamino)-3-phenylpropanamido]-2-(4-ethylthiazol-2-yl)ethyl}phenylsulfamic acid.

Rat Hindlimb Model of Collateral Development

Animal Selection

In an effort to control for variables affecting execution of treadmill running, rats are familiarized with exercising on the treadmill (tmill) a week prior to surgery. This consisted of the rat running on the tmill for intermittent bouts totaling five minutes daily at speeds between 20-25 m/sec and an elevation of 7°. Previous experience demonstrated that animals that did not run well during the familiarization period performed just as poorly during subsequent blood flow determinations, possibly altering collateral blood flow measurements. Based on this experience, rats that did not perform well during the familiarization period are not included in this study.

Surgical Procedures

An initial surgery is done to create hindlimb ischemia and implant osmotic pumps essentially as previously described with minor alterations. Briefly, adult male Sprague-Dawley rats (wt 340-390 grams) are first placed in an induction chamber with an $O_2$ flow rate of 1 L/min and Isoflurane (ISO) at 2.5%, body temperature is maintained via a heating pad under the chamber. Following induction, animals are transferred to a surgical mat and anesthesia is continued via a non-rebreathing circuit. A warming lamp is positioned above the rat and a rectal probe is placed to monitor the animal's body temperature. The groin areas bilaterally are clipped and prepared with alternating Betadine and alcohol scrubs (3x) and a sterile drape is placed over the rat. The left femoral artery is exposed through a skin incision and subsequently ligated in two positions 1 cm apart; distal to the inguinal ligament and proximal to the femoral circumflex artery. The skin is closed using either skin staples or Vetbond. The same procedure is repeated on the right side. Animals in the Continuous infusion groups had an Alzet 2ML2 pump (already primed) inserted into the SubQ space on their backs which delivered either 15 mg/kg/d or 5 mg/kg/d of 4-{(S)-2-[(S)-2-(tert-Butoxycarbonyl)-3-phenylpropanamido]-2-(4-ethylthiazol-2-yl) ethyl}phenylsulfamic acid, or Vehicle depending upon the treatment groups. Animals in the VEGF treatment group underwent an additional procedure for placement of an osmotic pump (Alert™ model #2004) on their neck. Prior to implantation, osmotic pumps are filled with VEGF 165 solution at a dose of 15 µg/kg/day, and primed overnight inside sterile saline beakers in a water bath (37° C.). Stretched PE50 catheters coated with PPG (Poly propylene glycol Aldrich #20-235-5) are attached using sterile technique and in accordance with manufacture's instructions the afternoon prior to surgery. For pump placement, an incision is made to expose the right jugular vein, an area is tunneled SubQ from the right side of the neck to the back and the pump is placed in the resulting SubQ pocket. The vessel is ligated with 4-0 silk, a cut is made in the vessel just distal to the tie and the catheter from the osmotic pump is threaded down stream (approx 2 cm) and secured with a second tie. The skin is closed in the same manner as above.

Blood Flow Assessment

Catheter Placement

Two weeks after the ligation surgery the rat underwent a second acute surgery to place indwelling catheters for microsphere measurements. Rats are anesthetized as described above. The animal is clipped, prepped, and EMLA cream is applied to each entry site. First an incision is made longitudinally at the ventral base of the tail using a 10 blade. A tapered PE 50 catheter is inserted approximately 3 cm into the ventral tail artery and anchored into place. The end of the catheter is then wrapped around the tail and tunneled SubQ over the back, exiting between the shoulder blades. Following tail artery cannulation, a midline neck incision is made to expose the left carotid artery for occlusive cannulation. A tapered PE 50 catheter is placed 3 cm into the carotid and the distal end is tunneled SubQ, exiting between the shoulder blades. The neck is closed with either skin stables or Vetbond and EMLA cream is applied. The exit site is closed around the catheters with a purse string suture stitch. The ends of the catheters are cauterized shut and the rat is allowed to recover from anesthesia for at least 4 hours.

Treadmill Protocol and Microsphere Measurements

For blood flow measurements, rats are placed onto the treadmill and the catheters are connected to extension tubing via 22 gage male-male connectors. For microsphere withdrawals and blood pressure measurements, the tail artery catheter is connected to a syringe (coated with tween and heparin-), which is "T" Ed to a withdrawal pump and a pressure transducer. The carotid catheter is used for injecting the microspheres. The rat began running at speed 20 m/min and an elevation of 7°. One minute into the run the pump is turned on at a rate of 0.5 ml/min, ten seconds later 0.5 ml ($1 \times 10^6$ spheres/mL) of florescent microspheres are infused into the carotid line followed by a 0.5 ml flush over 30 seconds. The pump is set to stop at 90 seconds. The tmill is stopped, the extension lines are replaced and the animal's lines are flushed, and the animal allowed to rest. The syringe and lines are removed from the pump and the reference blood sample is place in a labeled tube for processing. The withdrawal syringe and extension lines are flushed 3 times with 2% tween, waste is flushed the reference blood tube. A new syringe and lines are place on the pump and the procedure is repeated with the animal running at a faster speed, (25 m/min) and a different microsphere color is injected. At the completion of the second run, the animal is euthanized with 0.3 ml of Buthaneasia.

Tissue Harvesting and Analysis

Following euthanasia, tissues are removed, trimmed, weighed, recorded, and placed in marked tubes for processing. The samples are as follows for both left and right side; Soleus, Plantaris, Gastroc, Red Quads, and Kidneys. Blood samples are digested with 0.75 ml of 16 N KOH overnight. Tissue is digested with 5 ml of 4 N KOH overnight. Samples then vacuum filtered using 8-micron polycarbonate filters, and the filter paper is placed in a labeled vial with 1 ml of 2-ethoxyethyl acetate (2EEA). Following overnight digestion, samples are read using a black popypropolene plate on a fluorometer set on wavelengths 495-506 and 534-552. Exactly 270 ml of sample is pipetted into each well. Any further need for dilutions is noted on the animal's data sheet and corrected for in the raw data fluorescence. Raw data is converted to blood flow in terms of ml/min/100 g of tissue by the equation ({(Tissue Fluorescence/Tissue Weight g)/ (Reference Blood Fluorescence/Blood withdraw rate mL/min)}*100 g). Flow values for left and right leg tissues are averaged together to create one value for each animal, as long as even distribution is exhibited between the kidneys.

In this study the VEGF treatment groups had the expected significant improvement in GPS blood flow over the Vehicle control groups. In terms of the hemodynamic data the only significant difference between any of the groups is observed in the blood pressures of the treatment groups. These pressures are actually lower than the VEGF and/or Vehicle groups, suggesting that perfusion pressures to the GPS would also be slightly low. This means that any changes measured in blood flow are real not just a calculation artifact. Blood flows from the SubQ Continuous Infusion, showed a significant improvement in Calf blood flow as compared to vehicle for both doses (5 mg/kg/d and 15 mg/kg/d) of the compound. The data also revealed that the lower dose (5 mg/kg/d) did not elicit a maximal VEGF response, suggesting a possible dose dependency with this compound.

The results of this experiment are summarized herein below.

TABLE IX

Blood Pressure and Heart Rate

| | | | Continuous SubQ Infusion | | |
|---|---|---|---|---|---|
| | VEGF 15 µg/kg/d | Vehicle | Low 5 mg/kg/d | High 15 mg/kg/d | ANOVA p Value |
| Blood Pressure | | | | | |
| Pre-Exercise | 146 ± 2.5 | 141 ± 3.1 | 132 ± 3.9† | 137 ± 4.5 | NS |
| Exercise | 156 ± 2.3 | 151 ± 4.6 | 142 ± 3.2† | 144 ± 4.6 | NS |
| Post-Exercise | 149 ± 2.8 | 148 ± 5.3 | 135 ± 3.1 | 133 ± 3.7*† | <0.05 |
| Heart Rate | | | | | |
| Pre-Exercise | 452 ± 29.5 | 463 ± 18.1 | 429 ± 19.8 | 428 ± 13.5 | NS |
| Exercise | 489 ± 10.0 | 577 ± 15.2 | 487 ± 10.1 | 456 ± 13.0 | NS |
| Post-Exercise | 476 ± 18.1 | 468 ± 15.9 | 465 ± 18.8 | 462 ± 14.8 | NS |
| N | 10 | 8 | 10 | 10 | |

Data expressed as mean ± SE.
ANOVA analysis using Tukey's test
*significantly different from Vehicle,
†significantly different $p < 0.05$ vs VEGF

TABLE X

Blood Flow and Body Weight

| | | | Continuous SubQ Infusion | | |
|---|---|---|---|---|---|
| | VEGF 15 µg/kg/d | Vehicle | Low 5 mg/kg/d | High 15 mg/kg/d | ANOVA p Value |
| Blood Flow During exercise | | | | | |
| Calf (GPS) | 76 ± 1.1* | 53 ± 1.4 | 69 ± 2.0*† | 75 ± 1.7* | <0.001 |
| Kidney Weights | 296 ± 32.3 | 248 ± 24.9 | 318 ± 30.1 | 319 ± 37.9 | NS |
| Initial Body Wt | 372 ± 3.6 | 369 ± 2.7 | 365 ± 4.8 | 364 ± 4.8 | NS |
| Ending Body Wt | 421 ± 5.5 | 411 ± 5.5 | 413 ± 5.6 | 409 ± 5.5 | NS |
| N | 10 | 8 | 9 | 8 | |

Data expressed as mean ± SE.
ANOVA analysis using Tukey's test
*significantly different from Vehicle,
†significantly different $p < 0.05$ vs VEGF While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A compound having the formula:

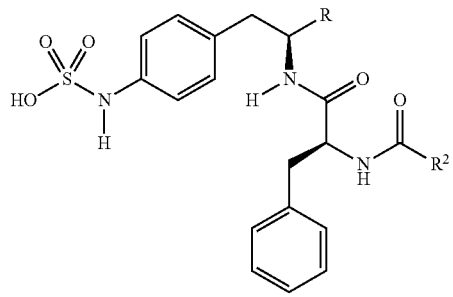

wherein R is a thiazolyl unit having the formula:

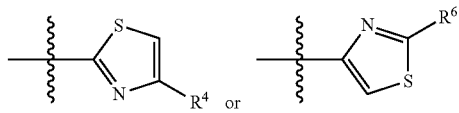

$R^4$ and $R^6$ are each chosen from:
i) substituted or unsubstituted $C_1$-$C_6$ linear, $C_3$-$C_6$ branched, or $C_3$-$C_6$ cyclic alkyl;
ii) substituted or unsubstituted phenyl; and
iii) substituted or unsubstituted thiophenyl; and
$R^2$ is $C_1$-$C_6$ linear or $C_3$-$C_6$ branched alkoxy; or
a pharmaceutically acceptable salt thereof.

2. The compound according to claim 1, wherein $R^4$ is $C_1$-$C_6$ linear, $C_3$-$C_6$ branched, or $C_3$-$C_6$ cyclic alkyl.

3. The compound according to claim 2, wherein $R^4$ is ethyl.

4. The compound according to claim 1, wherein $R^6$ is $C_1$-$C_6$ linear, $C_3$-$C_6$ branched, or $C_3$-$C_6$ cyclic alkyl.

5. The compound according to claim 4, wherein $R^6$ is ethyl.

6. The compound according to claim 1, wherein $R^4$ is thiophen-2-yl.

7. The compound according to claim 1, wherein $R^6$ is thiophen-2-yl.

8. The compound according to claim 1, wherein $R^2$ is $C_1$-$C_6$ linear alkoxy.

9. The compound according to claim 8, wherein $R^2$ is methoxy.

10. The compound according to claim 1, wherein the compound is the sodium salt.

* * * * *